US011254659B1

(12) United States Patent
Campbell et al.

(10) Patent No.: US 11,254,659 B1
(45) Date of Patent: Feb. 22, 2022

(54) CAPSAICINOID PRODRUG COMPOUNDS AND THEIR USE IN TREATING MEDICAL CONDITIONS

(71) Applicant: Centrexion Therapeutics Corporation, Boston, MA (US)

(72) Inventors: James N. Campbell, Baltimore, MD (US); Scott M. Duncan, Bedford, MA (US)

(73) Assignee: Centrexion Therapeutics Corporation, Boston, MA (US)

( * ) Notice: Subject to any disclaimer, the term of this patent is extended or adjusted under 35 U.S.C. 154(b) by 100 days.

(21) Appl. No.: 16/745,689

(22) Filed: Jan. 17, 2020

Related U.S. Application Data

(60) Provisional application No. 62/794,169, filed on Jan. 18, 2019.

(51) Int. Cl.
| | |
|---|---|
| *C07D 405/12* | (2006.01) |
| *C07D 405/14* | (2006.01) |
| *C07D 407/12* | (2006.01) |
| *C07D 413/14* | (2006.01) |
| *C07D 413/12* | (2006.01) |
| *C07F 9/22* | (2006.01) |
| *C07D 317/46* | (2006.01) |
| *A61K 45/06* | (2006.01) |

(52) U.S. Cl.
CPC ......... *C07D 405/12* (2013.01); *C07D 317/46* (2013.01); *C07D 405/14* (2013.01); *C07D 407/12* (2013.01); *C07D 413/12* (2013.01); *C07D 413/14* (2013.01); *C07F 9/222* (2013.01); *A61K 45/06* (2013.01)

(58) Field of Classification Search
CPC ..... C07F 9/222; C07D 405/12; C07D 413/14; C07D 407/12; C07D 413/12; C07D 317/46; C07D 405/14
USPC ......................................................... 514/89
See application file for complete search history.

(56) References Cited

U.S. PATENT DOCUMENTS

| | | |
|---|---|---|
| 5,962,532 A | 10/1999 | Campbell et al. |
| 6,248,788 B1 | 6/2001 | Robbins et al. |
| 7,632,519 B2 | 12/2009 | Jamieson et al. |
| 7,943,166 B2 | 5/2011 | Muhammad et al. |
| 7,943,666 B2 | 5/2011 | Singh et al. |
| 7,964,644 B2 | 6/2011 | Meyer |
| 8,158,682 B2 | 4/2012 | Sangameswaran et al. |
| 8,263,093 B2 | 9/2012 | Muhammad et al. |
| 8,273,390 B2 | 9/2012 | Muhammad et al. |
| 8,367,733 B2 | 2/2013 | Burch et al. |
| 8,420,600 B2 | 4/2013 | Burch et al. |
| 8,703,741 B2 | 4/2014 | Meyer |
| 8,734,770 B2 | 5/2014 | Muhammad et al. |
| 8,987,328 B2 | 3/2015 | Singh et al. |
| 9,044,452 B2 | 6/2015 | Meyer |
| 9,359,316 B1 | 6/2016 | Husfeld et al. |
| 9,422,233 B2 | 8/2016 | Laskin et al. |
| 9,492,409 B2 | 11/2016 | Kandula |
| 9,956,166 B2 | 5/2018 | Zucker et al. |
| 9,956,190 B2 | 5/2018 | Birbara et al. |
| 10,729,643 B2 | 8/2020 | Zucker et al. |
| 2010/0047181 A1 | 2/2010 | Meyer |
| 2015/0133561 A1 | 5/2015 | Birbara et al. |
| 2017/0239198 A1 | 8/2017 | Muzari |
| 2018/0169039 A1 | 6/2018 | Muhammad et al. |
| 2018/0311189 A1 | 11/2018 | Campbell et al. |
| 2019/0022036 A1 | 1/2019 | Campbell et al. |
| 2019/0038573 A1 | 2/2019 | Westphal et al. |
| 2020/0323771 A1 | 10/2020 | Zucker et al. |

FOREIGN PATENT DOCUMENTS

| | | |
|---|---|---|
| WO | WO-2004058286 A1 | 7/2004 |
| WO | WO-2009143297 A1 | 11/2009 |
| WO | WO-2014019095 A1 | 2/2014 |
| WO | WO-2016077749 A1 | 5/2016 |
| WO | WO-2016086063 A1 | 6/2016 |
| WO | WO-2017087803 A1 | 5/2017 |
| WO | WO-2017127628 A1 | 7/2017 |
| WO | WO-2017147146 A1 | 8/2017 |
| WO | WO-2017205534 A1 | 11/2017 |
| WO | WO-2018112725 A1 | 6/2018 |
| WO | WO-2018112728 A1 | 6/2018 |
| WO | WO-2018217937 A1 | 11/2018 |
| WO | WO-2019049112 A1 | 3/2019 |
| WO | WO-2020132553 A1 | 6/2020 |
| WO | WO-2020139797 A1 | 7/2020 |
| WO | WO-2020154261 A1 | 7/2020 |
| WO | WO-2020191506 A1 | 10/2020 |

OTHER PUBLICATIONS

Iadarola et al., "Long-term pain relief in canine osteoarthritis by a single intra-articular injection of resiniferatoxin, a potent TRPV1 agonist," Pain, (2018) vol. 159, pp. 2105-2114.
Resiniferatoxin to Treat Severe Pain Associated With Advanced Cancer, published Nov. 3, 2018 on clinicaltrials.gov, by Sorrento Therapeutics, Inc.
Study to Evaluate Safety and MTD of Epidural Resiniferatoxin Injection for Treatment of Intractable Cancer Pain, published Nov. 1, 2018 on clinicaltrials.gov, by Sorrento Therapeutics, Inc.
Study of Resiniferatoxin for Knee Pain in Moderate to Severe Osteoarthritis, published Oct. 24, 2018 on clinicaltrials.gov, by Sorrento Therapeutics, Inc.
U.S. Appl. No. 16/697,243, Methods and Compositions for Treating and Preventing Pain, filed Nov. 27, 2019.
U.S. Appl. No. 16/697,245, Methods and Compositions for Treating and Preventing Pain and Other Conditions, filed Nov. 27, 2019.
U.S. Appl. No. 16/745,636, Capsaicinoid Prodrug Compounds and Their Use in Treating Medical Conditions, filed Jan. 17, 2020.
U.S. Appl. No. 16/751,543, Methods and Compositions for Using Resiniferatoxin to Treat Pain, filed Jan. 24, 2020.

*Primary Examiner* — Kahsay Habte
(74) *Attorney, Agent, or Firm* — Dechert LLP

(57) ABSTRACT

The invention provides capsaicinoid prodrug compounds (e.g., prodrugs of resiniferatoxin, tinyatoxin, iodoresiniferatoxin, and related compounds), pharmaceutical compositions, and their use in the treatment of medical conditions, such as pain, and in agonizing TRPV1 activity.

20 Claims, No Drawings

CAPSAICINOID PRODRUG COMPOUNDS AND THEIR USE IN TREATING MEDICAL CONDITIONS

CROSS-REFERENCE TO RELATED APPLICATIONS

This application claims the benefit of and priority to U.S. Provisional Patent Application Ser. No. 62/794,169, filed Jan. 18, 2019, the contents of which are hereby incorporated by reference in their entirety.

FIELD OF THE INVENTION

The invention provides capsaicinoid prodrug compounds (e.g., prodrugs of resiniferatoxin, tinyatoxin, iodoresiniferatoxin, and related compounds), pharmaceutical compositions, and their use in the treatment of medical conditions, such as pain, and in agonizing TRPV1 activity.

BACKGROUND

Pain can function as a protective mechanism that allows healthy human beings and animals to avoid tissue damage and/or prevent further damage to injured tissue. However, there are many instances in which pain persists beyond its usefulness. Such unnecessary suffering from pain can impair a subject's physical mobility, mental performance, and even contribute to depression.

Substantial resources have been devoted over the years to researching the causes of various types of pain and to the development of medicine to attenuate pain experienced by a patient. Exemplary classes of common pain-relief medications include opioids, non-steroidal anti-inflammatory agents, corticosteroids, and centrally acting agents such as anti-depressants, anti-epileptics, pregabalin, and gabapentin. Resiniferatoxin and related compounds have been described for use in treating pain. See, for example, U.S. Pat. Nos. 5,290,816; 8,420,600; 8,367,733; and 8,158,682; and international patent application publications WO 2002/076444 and WO 2008/011532. Prodrug compounds that undergo degradation to release resiniferatoxin or a related compound have been described. Exemplary prodrugs of resiniferatoxin and related compounds include those described in U.S. Pat. Nos. 7,632,519, 9,359,316, and international patent application WO 2016/086063.

Due to the unmet need for additional treatment options to achieve relief from pain, particularly treatment options that do not suffer from the addiction problems associated with many opioid-based pain therapies, the need exists for compounds useful in treating pain, pharmaceutical compositions containing the same, and methods for treating pain. The present invention addresses this need and provides other related advantages.

SUMMARY

The invention provides capsaicinoid prodrug compounds (e.g., prodrugs of resiniferatoxin, tinyatoxin, iodoresiniferatoxin, and related compounds), pharmaceutical compositions, and their use in the treatment of medical conditions, such as pain, and in agonizing TRPV1 activity. The prodrug compounds are advantageous in part because they contain functionality permitting more specific control of the rate at which the prodrug releases resiniferatoxin or related compounds in an aqueous environment. The prodrug compounds are desirably formulated into a pharmaceutical composition for administration to a subject, which may be an aqueous solution for injection. The prodrug compounds and pharmaceutical compositions containing the same may be used in therapeutic methods described herein, including methods for treating pain, such as joint pain associated with osteoarthritis.

One aspect of the invention provides a collection of carbamate compounds, such as a compound represented by Formula I:

(I)

or a pharmaceutically acceptable salt thereof, where the variables are as defined in the detailed description. Further description of additional collections of prodrug compounds are described in the detailed description.

Another aspect of the invention provides a collection of carbamate compounds represented by Formula II:

(II)

or a pharmaceutically acceptable salt thereof, where the variables are as defined in the detailed description. Further description of additional collections of prodrug compounds are described in the detailed description.

Another aspect of the invention provides a collection of ester and carbonate compounds represented by Formula III:

(III)

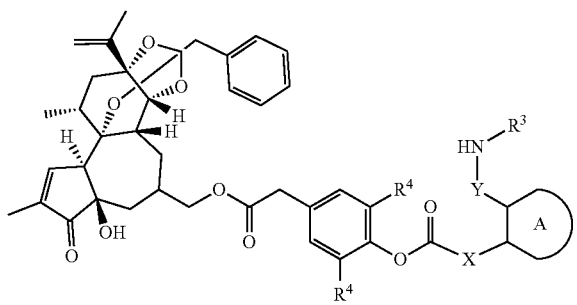

or a pharmaceutically acceptable salt thereof, where the variables are as defined in the detailed description. Further description of additional collections of prodrug compounds are described in the detailed description.

Another aspect of the invention provides a collection of amino oxoacetate compounds represented by Formula IV:

(IV)

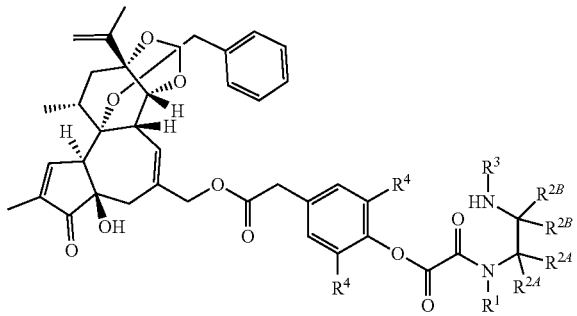

or a pharmaceutically acceptable salt thereof, where the variables are as defined in the detailed description. Further description of additional collections of prodrug compounds are described in the detailed description.

Another aspect of the invention provides a collection of phosphoramidate compounds represented by Formula V:

(V)

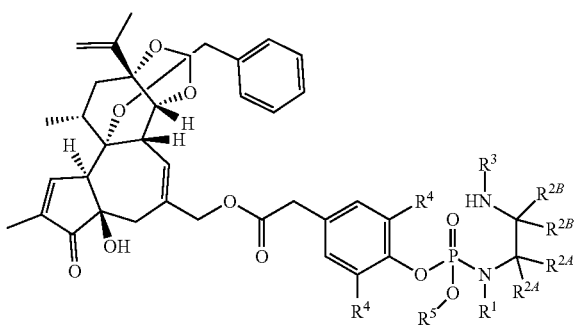

or a pharmaceutically acceptable salt thereof, where the variables are as defined in the detailed description. Further description of additional collections of prodrug compounds are described in the detailed description.

The prodrug compounds may be part of a pharmaceutical composition comprising a pharmaceutically acceptable carrier. In certain embodiments, the pharmaceutical composition is an aqueous solution formulated for injection.

Another aspect of the invention provides a method of treating or preventing pain in a subject. The method comprises administering a therapeutically effective amount of a compound described herein, such as a compound of Formula I, II, III, IV, or V, to a subject in need thereof to treat or prevent the pain. The compound may be used as monotherapy or as part of a combination therapy, to treat or prevent the pain. Exemplary types of pain that may be treated include, for example, nociceptive pain, neuropathic pain, pain due to nerve injury, pain from a neuralgia, pain from a neuroma, pain from a myalgia, pain due to cancer, pain due to bursitis, pain due to tendonitis, or pain associated with an orthopedic disorder. In certain embodiments, the pain is joint pain, such as osteoarthritic joint pain.

Another aspect of the invention provides a method of agonizing the activity of TRPV1. The method comprises exposing a TRPV1 to an effective amount of a compound described herein, such as a compound of Formula I, II, III, IV, or V, to agonize the activity of said TRPV1.

DETAILED DESCRIPTION

The invention provides capsaicinoid prodrug compounds (e.g., prodrugs of resiniferatoxin, tinyatoxin, iodoresiniferatoxin, and related compounds), pharmaceutical compositions, and their use in the treatment of medical conditions, such as pain, and in agonizing TRPV1 activity. The prodrug compounds are advantageous in part because they contain functionality permitting more specific control of the rate at which the prodrug releases resiniferatoxin or related compounds in an aqueous environment. The prodrug compounds are desirably formulated into a pharmaceutical composition for administration to a subject, which may be an aqueous solution for injection. The prodrug compounds and pharmaceutical compositions containing the same may be used in therapeutic methods described herein, including methods for treating pain, such as joint pain associated with osteoarthritis. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "—O-alkyl" etc.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. Exemplary alkylene groups include —$CH_2$—, —$CH_2CH_2$—, and —$CH_2C(H)(CH_3)CH_2$—. The term "—($C_0$ alkylene)-" refers to a bond. Accordingly, the term "—($C_{0-3}$ alkylene)-" encompasses a bond (i.e., $C_0$) and a —($C_{1-3}$ alkylene) group.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl. The term "halocycloalkyl" refers to a cycloalkyl group that is substituted with at least one halogen.

The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like.

The term "hydroxyalkyl" refers to an alkyl group that is substituted with at least one hydroxyl. Exemplary hydroxyalkyl groups include —$CH_2CH_2OH$, —$C(H)(OH)CH_3$, —$CH_2C(H)(OH)CH_2CH_2OH$, and the like.

The term "aralkyl" refers to an alkyl group substituted with an aryl group. Exemplary aralkyl groups include

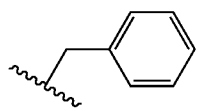 [SMILES: *Cc1ccccc1]

and

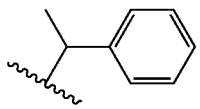

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "cycloalkenyl" refers to a monovalent unsaturated cyclic, bicyclic, or bridged (e.g., adamantyl) carbocyclic hydrocarbon containing at least one C—C double bond. In certain embodiments, the cycloalkenyl contains 5-10, 5-8, or 5-6 carbons, referred to herein, e.g., as "$C_5$-$C_6$ cycloalkenyl". Exemplary cycloalkenyl groups include cyclohexenyl and cyclopentenyl.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "heteroaryl" is art-recognized and refers to aromatic groups that include at least one ring heteroatom. In certain instances, a heteroaryl group contains 1, 2, 3, or 4 ring heteroatoms (e.g., O, N, and S). Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "heteroaryl" also includes polycyclic aromatic ring systems having two or more rings in which two or more ring atoms are common to two adjoining rings (the rings are "fused rings") wherein all of the fused rings are heteroaromatic, e.g., in a naphthyridinyl group. In certain embodiments, the heteroaryl is a 5-6 membered monocyclic ring or a 9-10 membered bicyclic ring.

The terms ortho, meta, and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. The nonaromatic heterocyclic rings may be, for example, monocyclic, bicyclic, or spirocyclic. Some non-limiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-8 membered ring that, unless specified otherwise, is substituted or unsubstituted. In certain embodiments, the heterocyclyl group is a 3-8 membered ring that contains 1, 2, or 3 ring heteroatoms selected from oxygen, sulfur, and nitrogen. The term "aza-heterocyclyl" refers to a heterocyclyl group having at least one nitrogen atom in the heterocyclyl ring.

The term "heterocycloalkyl" refers to a saturated heterocyclyl group having, for example, 3-7 ring atoms selected from carbon and heteroatoms (e.g., O, N, or S). The term "aza-heterocycloalkyl" refers to a saturated heterocyclyl group having at least one nitrogen atom in the heterocycloalkyl ring.

The terms "amine" and "amino" are art-recognized and refer to both unsubstituted and substituted amines, e.g., a moiety that may be represented by the general formulas:

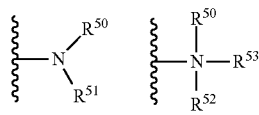

wherein $R^{50}$, $R^{51}$, $R^{52}$ and $R^{53}$ each independently represent a hydrogen, an alkyl, an alkenyl, —(CH$_2$)$_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O— alkenyl, —O-alkynyl, and —O—(CH$_2$)$_m$—$R^{61}$, where m and $R^{61}$ are described above.

The term "oxo" is art-recognized and refers to a "=O" substituent. For example, a cyclopentane substituted with an oxo group is cyclopentanone.

The symbol " ⌇ " indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound" or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$IC_{50}$" is art-recognized and refers to the concentration of a compound that is required to achieve 50% inhibition of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_3$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium (H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran. The abbreviation "DCM" is art-recognized and refers to dichloromethane. The abbreviation "DMF" is art-recognized and refers to dimethylformamide. The abbreviation "EDTA" is art-recognized and refers to ethylenediaminetetraacetic acid. The abbreviation "TFA" is art-recognized and refers to trifluoroacetic acid. The abbreviation "Ts" is art-recognized and refers to tosylate. The abbreviation "TBS" is art-recognized and refers to tert-butyldimethylsilyl. The abbreviation "DMSO" is art-recognized and refers to dimethylsulfoxide.

As a general matter, compositions specifying a percentage are by weight unless otherwise specified.

I. Prodrug Compounds

The invention provides prodrug compounds of resiniferatoxin, tinyatoxin, iodoresiniferatoxin, and related compounds. The prodrug compounds may be used in the pharmaceutical compositions and therapeutic methods described herein. Exemplary prodrug compounds are described in the following sections, along with exemplary procedures for making the compounds.

One aspect of the invention provides a compound represented by Formula I:

(I)

or a pharmaceutically acceptable salt thereof; wherein:

$R^1$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl; or two occurrences of $R^1$ are taken together with the carbon atom to which they are attached to form a 3-6 membered saturated carbocyclic or heterocyclic ring;

$R^2$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl; or two occurrences of $R^2$ attached to the same carbon atom are taken together to represent an oxo group; or two occurrences of $R^2$ attached to the same carbon atom are taken together with the carbon atom to which they are attached to form a 3-6 membered saturated carbocyclic or heterocyclic ring;

$R^3$ is hydrogen, $C_{1-6}$ alkyl, $C_{1-6}$ haloalkyl, $C_{3-7}$ cycloalkyl, 4-8 membered heterocycloalkyl, or $—C(=NH)—NH_2$; wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl; provided that if $R^3$ is hydrogen, methyl, or ethyl, then at least one of $R^1$ and $R^2$ is not hydrogen; and $R^4$ represents independently for each occurrence hydrogen, halogen, $C_{1-4}$ alkyl, $C_{1-4}$ haloalkyl, $C_{1-4}$ alkoxyl, or $C_{1-4}$ haloalkoxyl;

m is 0, 1, 2, or 3; and n is 0, 1, or 2.

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula I in the form of a pharmaceutically acceptable salt. In certain embodiments, the compound is a compound of Formula I.

In certain embodiments, at least one $R^1$ represents $C_{1-6}$ alkyl, $C_{1-6}$ haloalkyl, $C_{3-7}$ cycloalkyl, $C_6$ aryl, or 3-8 membered heterocycloalkyl; or two occurrences of $R^1$ are taken together with the carbon atom to which they are attached to form a 3-6 membered saturated carbocyclic or heterocyclic ring. In certain embodiments, at least one $R^1$ represents $C_{1-4}$ alkyl or $C_{1-4}$ haloalkyl; or two occurrences of $R^1$ are taken together with the carbon atom to which they are attached to form a 3-6 membered saturated carbocyclic ring. In certain embodiments, at least one $R^1$ represents $C_{1-4}$ alkyl or $C_{1-4}$ haloalkyl.

In certain embodiments, $R^1$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl. In certain embodiments, $R^1$ represents independently for each occurrence $C_{1-6}$ alkyl or $C_{3-7}$ cycloalkyl. In certain embodiments, $R^1$ is hydrogen.

In certain embodiments, two occurrences of $R^1$ are taken together with the carbon atom to which they are attached to form a 3-6 membered saturated carbocyclic or heterocyclic ring. In certain embodiments, $R^1$ represents independently for each occurrence hydrogen, $C_{1-4}$ alkyl, or $C_{1-4}$ haloalkyl; or two occurrences of $R^1$ are taken together with the carbon atom to which they are attached to form a 3-6 membered saturated carbocyclic ring.

In certain embodiments, at least one $R^2$ represents $C_{1-6}$ alkyl, $C_{1-6}$ haloalkyl, $C_{3-7}$ cycloalkyl, $C_6$ aryl, or 3-8 membered heterocycloalkyl; or two occurrences of $R^2$ attached to the same carbon atom are taken together to represent an oxo group; or two occurrences of $R^2$ attached to the same carbon atom are taken together with the carbon atom to which they are attached to form a 3-6 membered saturated carbocyclic or heterocyclic ring. In certain embodiments, at least one $R^2$ represents $C_{1-4}$ alkyl or $C_{1-4}$ haloalkyl; or two occurrences of $R^2$ attached to the same carbon atom are taken together to represent an oxo group; or two occurrences of $R^2$ attached to the same carbon atom are taken together with the carbon atom to which they are attached to form a 3-6 membered saturated carbocyclic ring. In certain embodiments, at least one $R^2$ represents $C_{1-4}$ alkyl or $C_{1-4}$ haloalkyl; or two occurrences of $R^2$ attached to the same carbon atom are taken together with the carbon atom to which they are attached to form a 3-6 membered saturated carbocyclic ring. In certain embodiments, at least one $R^2$ represents $C_{1-4}$ alkyl or $C_{1-4}$ haloalkyl.

In certain embodiments, $R^2$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl. In certain embodiments, $R^2$ represents independently for each occurrence $C_{1-6}$ alkyl or $C_{3-7}$ cycloalkyl. In certain embodiments, $R^2$ represents independently for each occurrence $C_{1-4}$ alkyl or $C_{1-4}$ haloalkyl. In certain embodiments, $R^2$ is $C_{1-6}$ alkyl. In certain embodiments, $R^2$ is hydrogen.

In certain embodiments, two occurrences of $R^2$ attached to the same carbon atom are taken together to represent an oxo group. In certain embodiments, two occurrences of $R^2$ attached to the same carbon atom are taken together with the carbon atom to which they are attached to form a 3-6 membered saturated carbocyclic or heterocyclic ring. In certain embodiments, two occurrences of $R^2$ attached to the same carbon atom are taken together with the carbon atom to which they are attached to form a 3-6 membered saturated carbocyclic ring. In certain embodiments, two occurrences of $R^2$ attached to the same carbon atom are taken together with the carbon atom to which they are attached to form a 3-membered saturated carbocyclic ring. In certain embodiments, two occurrences of $R^2$ attached to the same carbon atom are taken together with the carbon atom to which they are attached to form a 3-6 membered saturated heterocyclic ring. In certain embodiments, $R^2$ represents independently for each occurrence hydrogen, $C_{1-4}$ alkyl, or $C_{1-4}$ haloalkyl; or two occurrences of $R^2$ attached to the same carbon atom are taken together with the carbon atom to which they are attached to form a 3-6 membered saturated carbocyclic ring.

In certain embodiments, $R^3$ is hydrogen. In certain embodiments, $R^3$ is $C_{1-6}$ alkyl, $C_{1-6}$ haloalkyl, or $C_{3-7}$ cycloalkyl. In certain embodiments, $R^3$ is $C_{1-6}$ alkyl or $C_{1-6}$ haloalkyl. In certain embodiments, $R^3$ is $C_{1-6}$ alkyl. In certain embodiments, $R^3$ is $C_{1-6}$ haloalkyl. In certain embodiments, $R^3$ is $C_{3-7}$ cycloalkyl. In certain embodiments, $R^3$ is 4-8 membered heterocycloalkyl. In certain embodiments, $R^3$ is —C(=NH)—NH$_2$.

In certain embodiments, $R^3$ is $C_{3-7}$ cycloalkyl or 4-8 membered heterocycloalkyl, each of which is optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is $C_{3-7}$ cycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is 4-8 membered heterocycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl.

In certain embodiments, $R^4$ represents independently for each occurrence hydrogen, halogen, or $C_{1-4}$ alkoxyl. In certain embodiments, $R^4$ represents independently for each occurrence hydrogen, iodo, or methoxy. In certain embodiments, one occurrence of $R^4$ is methoxy, and the other occurrence of $R^4$ is hydrogen. In certain embodiments, $R^4$ is hydrogen. In certain embodiments, one occurrence of $R^4$ is methoxy, and the other occurrence of $R^4$ is iodo.

In certain embodiments, m is 0. In certain embodiments, m is 1. In certain embodiments, m is 2. In certain embodiments, m is 3.

In certain embodiments, n is 0. In certain embodiments, n is 1. In certain embodiments, n is 2.

The description above describes multiple embodiments relating to compounds of Formula I. The patent application specifically contemplates all combinations of the embodiments.

Another aspect of the invention provides a compound represented by Formula II:

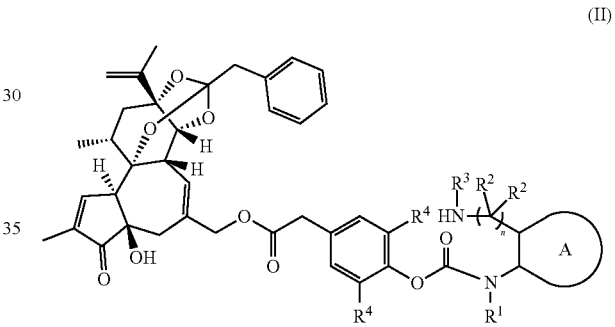

(II)

or a pharmaceutically acceptable salt thereof; wherein:

$R^1$ is hydrogen, $C_{1-6}$ alkyl, $C_{1-6}$ haloalkyl, $C_{3-7}$ cycloalkyl, $C_6$ aryl, or 4-8 membered heterocycloalkyl;

$R^2$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl; or two occurrences of $R^2$ are taken together to represent an oxo group; or two occurrences of $R^2$ are taken together with the carbon atom to which they are attached to form a 3-6 membered saturated carbocyclic or heterocyclic ring;

$R^3$ is hydrogen, $C_{1-6}$ alkyl, $C_{1-6}$ haloalkyl, $C_{3-7}$ cycloalkyl, 4-8 membered heterocycloalkyl, or —C(=NH)—NH$_2$; wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

$R^4$ represents independently for each occurrence hydrogen, halogen, $C_{1-4}$ alkyl, $C_{1-4}$ haloalkyl, $C_{1-4}$ alkoxyl, or $C_{1-4}$ haloalkoxyl;

Ring A is one of the following:
  a 3-8 membered heterocyclic ring or a $C_{3-8}$ saturated or partially unsaturated carbocyclic ring, each of which is optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl; or a 6-membered carbocyclic aromatic ring substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl; and n is 0 or 1.

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula II in the form of a pharmaceutically acceptable salt. In certain embodiments, the compound is a compound of Formula II.

In certain embodiments, $R^1$ is hydrogen or $C_{1-6}$ alkyl. In certain embodiments, $R^1$ is $C_{3-7}$ cycloalkyl, $C_6$ aryl, or 4-8 membered heterocycloalkyl. In certain embodiments, $R^1$ is $C_{1-4}$ alkyl, $C_{1-4}$ haloalkyl, or $C_{3-7}$ cycloalkyl.

In certain embodiments, at least one $R^2$ represents $C_{1-6}$ alkyl, $C_{1-6}$ haloalkyl, $C_{3-7}$ cycloalkyl, $C_6$ aryl, or 3-8 membered heterocycloalkyl; or two occurrences of $R^2$ are taken together to represent an oxo group; or two occurrences of $R^2$ are taken together with the carbon atom to which they are attached to form a 3-6 membered saturated carbocyclic or heterocyclic ring. In certain embodiments, at least one $R^2$ represents independently for each occurrence $C_{1-6}$ alkyl or $C_{3-7}$ cycloalkyl; or two occurrences of $R^2$ are taken together with the carbon atom to which they are attached to form a 3-6 membered saturated carbocyclic or heterocyclic ring. In certain embodiments, at least one $R^2$ represents $C_{1-4}$ alkyl or $C_{1-4}$ haloalkyl; or two occurrences of $R^2$ are taken together to represent an oxo group; or two occurrences of $R^2$ are taken together with the carbon atom to which they are attached to form a 3-6 membered saturated carbocyclic ring. In certain embodiments, at least one $R^2$ represents $C_{1-4}$ alkyl or $C_{1-4}$ haloalkyl; or two occurrences of $R^2$ are taken together with the carbon atom to which they are attached to form a 3-6 membered saturated carbocyclic ring. In certain embodiments, at least one $R^2$ represents $C_{1-4}$ alkyl or $C_{1-4}$ haloalkyl.

In certain embodiments, $R^2$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl. In certain embodiments, $R^2$ represents independently for each occurrence $C_{1-6}$ alkyl or $C_{3-7}$ cycloalkyl. In certain embodiments, $R^2$ represents independently for each occurrence $C_{1-4}$ alkyl or $C_{1-4}$ haloalkyl. In certain embodiments, $R^2$ is $C_{1-6}$ alkyl. In certain embodiments, $R^2$ is hydrogen.

In certain embodiments, two occurrences of $R^2$ are taken together to represent an oxo group. In certain embodiments, two occurrences of $R^2$ are taken together with the carbon atom to which they are attached to form a 3-6 membered saturated carbocyclic or heterocyclic ring. In certain embodiments, two occurrences of $R^2$ are taken together with the carbon atom to which they are attached to form a 3-6 membered saturated carbocyclic ring. In certain embodiments, two occurrences of $R^2$ are taken together with the carbon atom to which they are attached to form a 3-membered saturated carbocyclic ring. In certain embodiments, two occurrences of $R^2$ are taken together with the carbon atom to which they are attached to form a 3-6 membered saturated heterocyclic ring.

In certain embodiments, $R^2$ represents independently for each occurrence $C_{1-6}$ alkyl or $C_{3-7}$ cycloalkyl; or two occurrences of $R^2$ are taken together with the carbon atom to which they are attached to form a 3-6 membered saturated carbocyclic or heterocyclic ring. In certain embodiments, $R^2$ represents independently for each occurrence hydrogen, $C_{1-4}$ alkyl, or $C_{1-4}$ haloalkyl; or two occurrences of $R^2$ are taken together with the carbon atom to which they are attached to form a 3-6 membered saturated carbocyclic ring.

In certain embodiments, $R^3$ is hydrogen. In certain embodiments, $R^3$ is $C_{1-6}$ alkyl, $C_{1-6}$ haloalkyl, or $C_{3-7}$ cycloalkyl. In certain embodiments, $R^3$ is $C_{1-6}$ alkyl or $C_{1-6}$ haloalkyl. In certain embodiments, $R^3$ is $C_{1-6}$ alkyl. In certain embodiments, $R^3$ is $C_{1-6}$ haloalkyl. In certain embodiments, $R^3$ is $C_{3-7}$ cycloalkyl. In certain embodiments, $R^3$ is 4-8 membered heterocycloalkyl. In certain embodiments, $R^3$ is —C(=NH)—NH$_2$.

In certain embodiments, $R^3$ is $C_{3-7}$ cycloalkyl or 4-8 membered heterocycloalkyl, each of which is optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is $C_{3-7}$ cycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is 4-8 membered heterocycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl.

In certain embodiments, $R^4$ represents independently for each occurrence hydrogen, halogen, or $C_{1-4}$ alkoxyl. In certain embodiments, $R^4$ represents independently for each occurrence hydrogen, iodo, or methoxy. In certain embodiments, one occurrence of $R^4$ is methoxy, and the other occurrence of $R^4$ is hydrogen. In certain embodiments, $R^4$ is hydrogen. In certain embodiments, one occurrence of $R^4$ is methoxy, and the other occurrence of $R^4$ is iodo.

In certain embodiments, Ring A is a 3-8 membered heterocyclic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl. In certain embodiments, Ring A is a 5-6 membered heteroaromatic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl. In certain embodiments, Ring A is a 3-8 membered saturated heterocyclic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl. In certain embodiments, Ring A is a 5-6 membered saturated heterocyclic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl.

In certain embodiments, Ring A is a 3-8 membered heterocyclic ring. In certain embodiments, Ring A is a 5-6 membered heteroaromatic ring. In certain embodiments, Ring A is a 3-8 membered saturated heterocyclic ring. In certain embodiments, Ring A is a 5-6 membered saturated heterocyclic ring.

In certain embodiments, Ring A is a $C_{3-8}$ saturated or partially unsaturated carbocyclic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl. In certain embodiments, Ring A is a $C_{3-8}$ saturated carbocyclic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl. In certain embodiments, Ring A is a $C_{5-6}$ saturated carbocyclic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl.

In certain embodiments, Ring A is a $C_{3-8}$ saturated or partially unsaturated carbocyclic ring. In certain embodiments, Ring A is a $C_{3-8}$ saturated carbocyclic ring. In certain embodiments, Ring A is a $C_{5-6}$ saturated carbocyclic ring.

In certain embodiments, Ring A is a 6-membered carbocyclic aromatic ring substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl.

In certain embodiments, n is 0. In certain embodiments, n is 1.

The description above describes multiple embodiments relating to compounds of Formula II. The patent application specifically contemplates all combinations of the embodiments.

Another aspect of the invention provides a compound represented by Formula III:

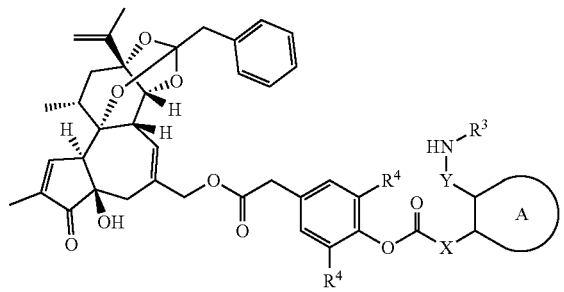

(III)

or a pharmaceutically acceptable salt thereof; wherein:
X is —C(R$^1$)$_2$—, a bond, or —O—;
Y is —C(R$^2$)$_2$— or a bond; provided X and Y are not both a bond;
R$^1$ represents independently for each occurrence hydrogen, halogen, $C_{1-6}$ alkyl, $C_{1-6}$ haloalkyl, $C_{3-7}$ cycloalkyl, $C_6$ aryl, or 3-8 membered heterocycloalkyl; or two occurrences of R$^1$ are taken together with the carbon atom to which they are attached to form a 3-6 membered saturated carbocyclic or heterocyclic ring;
R$^2$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl; or two occurrences of R$^2$ are taken together to represent an oxo group; or two occurrences of R$^2$ are taken together with the carbon atom to which they are attached to form a 3-6 membered saturated carbocyclic or heterocyclic ring;
R$^3$ is hydrogen, $C_{1-6}$ alkyl, $C_{1-6}$ haloalkyl, $C_{3-7}$ cycloalkyl, 4-8 membered heterocycloalkyl, or —C(=NH)—NH$_2$; wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

R$^4$ represents independently for each occurrence hydrogen, halogen, $C_{1-4}$ alkyl, $C_{1-4}$ haloalkyl, $C_{1-4}$ alkoxyl, or $C_{1-4}$ haloalkoxyl; and Ring A is one of the following:
a 6-membered carbocyclic aromatic ring or a 5-6 membered heteroaromatic ring, each of which is optionally substituted with 1, 2, or 3 substitutents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl; or
a $C_{3-8}$ saturated or partially unsaturated carbocyclic ring or a 3-8 membered saturated or partially unsaturated heterocylic ring, each of which is optionally substituted with 1, 2, or 3 substitutents independently selected from the group consisting of halogen, hydroxyl, oxo, $C_{1-6}$ alkyl, $C_{1-6}$ haloalkyl, $C_{3-7}$ cycloalkyl, $C_{1-4}$ alkoxyl, and $C_{1-4}$ haloalkoxyl.

The definitions of variables in Formula III above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula III in the form of a pharmaceutically acceptable salt. In certain embodiments, the compound is a compound of Formula III.

In certain embodiments, X is —C(R$^1$)$_2$—. In certain embodiments, X is —C(R$^1$)$_2$—, and Y is —C(R$^2$)$_2$—. In certain embodiments, X is —C(R')$_2$—, and Y is a bond. In certain embodiments, X is a bond, and Y is —C(R$^2$)$_2$—. In certain embodiments, X is —O—. In certain embodiments, X is —O—, and Y is —C(R$^2$)$_2$—. In certain embodiments, X is —O—, and Y is a bond.

In certain embodiments, R$^1$ is hydrogen. In certain embodiments, R$^1$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl. In certain embodiments, two occurrences of R$^1$ are taken together with the carbon atom to which they are attached to form a 3-6 membered saturated carbocyclic or heterocyclic ring. In certain embodiments, R$^1$ represents independently for each occurrence $C_{1-6}$ alkyl or $C_{3-7}$ cycloalkyl, or two occurrences of R$^1$ are taken together with the carbon atom to which they are attached to form a 3-6 membered saturated carbocyclic or heterocyclic ring.

In certain embodiments, at least one R$^2$ represents $C_{1-6}$ alkyl, $C_{1-6}$ haloalkyl, $C_{3-7}$ cycloalkyl, $C_6$ aryl, or 3-8 membered heterocycloalkyl; or two occurrences of R$^2$ are taken together to represent an oxo group; or two occurrences of R$^2$ are taken together with the carbon atom to which they are attached to form a 3-6 membered saturated carbocyclic or heterocyclic ring. In certain embodiments, at least one R$^2$ represents independently for each occurrence $C_{1-6}$ alkyl or $C_{3-7}$ cycloalkyl; or two occurrences of R$^2$ are taken together with the carbon atom to which they are attached to form a 3-6 membered saturated carbocyclic or heterocyclic ring. In certain embodiments, at least one R$^2$ represents $C_{1-4}$ alkyl or $C_{1-4}$ haloalkyl; or two occurrences of R$^2$ are taken together to represent an oxo group; or two occurrences of R$^2$ are taken together with the carbon atom to which they are attached to form a 3-6 membered saturated carbocyclic ring. In certain embodiments, at least one $R^2$ represents $C_{1-4}$ alkyl or $C_{1-4}$ haloalkyl; or two occurrences of $R^2$ are taken together with the carbon atom to which they are attached to form a 3-6 membered saturated carbocyclic ring. In certain embodiments, at least one $R^2$ represents $C_{1-4}$ alkyl or $C_{1-4}$ haloalkyl.

In certain embodiments, $R^2$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl. In certain embodiments, $R^2$ represents independently for each occurrence $C_{1-6}$ alkyl or $C_{3-7}$ cycloalkyl. In certain embodiments, $R^2$ represents independently for each occurrence $C_{1-4}$ alkyl or $C_{1-4}$ haloalkyl. In certain embodiments, $R^2$ is $C_{1-6}$ alkyl. In certain embodiments, $R^2$ is hydrogen.

In certain embodiments, two occurrences of $R^2$ are taken together to represent an oxo group. In certain embodiments, two occurrences of $R^2$ are taken together with the carbon atom to which they are attached to form a 3-6 membered saturated carbocyclic or heterocyclic ring. In certain embodiments, two occurrences of $R^2$ are taken together with the carbon atom to which they are attached to form a 3-6 membered saturated carbocyclic ring. In certain embodiments, two occurrences of $R^2$ are taken together with the carbon atom to which they are attached to form a 3-membered saturated carbocyclic ring. In certain embodiments, two occurrences of $R^2$ are taken together with the carbon atom to which they are attached to form a 3-6 membered saturated heterocyclic ring.

In certain embodiments, $R^2$ represents independently for each occurrence $C_{1-6}$ alkyl or $C_{3-7}$ cycloalkyl; or two occurrences of $R^2$ are taken together with the carbon atom to which they are attached to form a 3-6 membered saturated carbocyclic or heterocyclic ring. In certain embodiments, $R^2$ represents independently for each occurrence hydrogen, $C_{1-4}$ alkyl, or $C_{1-4}$ haloalkyl; or two occurrences of $R^2$ are taken together with the carbon atom to which they are attached to form a 3-6 membered saturated carbocyclic ring.

In certain embodiments, $R^3$ is hydrogen. In certain embodiments, $R^3$ is $C_{1-6}$ alkyl, $C_{1-6}$ haloalkyl, or $C_{3-7}$ cycloalkyl. In certain embodiments, $R^3$ is $C_{1-6}$ alkyl or $C_{1-6}$ haloalkyl. In certain embodiments, $R^3$ is $C_{1-6}$ alkyl. In certain embodiments, $R^3$ is $C_{1-6}$ haloalkyl. In certain embodiments, $R^3$ is $C_{3-7}$ cycloalkyl. In certain embodiments, $R^3$ is 4-8 membered heterocycloalkyl. In certain embodiments, $R^3$ is —C(=NH)—NH$_2$.

In certain embodiments, $R^3$ is $C_{3-7}$ cycloalkyl or 4-8 membered heterocycloalkyl, each of which is optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is $C_{3-7}$ cycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is 4-8 membered heterocycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl.

In certain embodiments, $R^4$ represents independently for each occurrence hydrogen, halogen, or $C_{1-4}$ alkoxyl. In certain embodiments, $R^4$ represents independently for each occurrence hydrogen, iodo, or methoxy. In certain embodiments, one occurrence of $R^4$ is methoxy, and the other occurrence of $R^4$ is hydrogen. In certain embodiments, $R^4$ is hydrogen. In certain embodiments, one occurrence of $R^4$ is methoxy, and the other occurrence of $R^4$ is iodo.

In certain embodiments, Ring A is a 6-membered carbocyclic aromatic ring or a 5-6 membered heteroaromatic ring, each of which is optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl. In certain embodiments, Ring A is a 6-membered carbocyclic aromatic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl. In certain embodiments, Ring A is a 5-6 membered heteroaromatic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl.

In certain embodiments, Ring A is a 6-membered carbocyclic aromatic ring or a 5-6 membered heteroaromatic ring. In certain embodiments, Ring A is a 6-membered carbocyclic aromatic ring. In certain embodiments, Ring A is a 5-6 membered heteroaromatic ring.

In certain embodiments, Ring A is a $C_{3-8}$ saturated or partially unsaturated carbocyclic ring optionally substituted with 1, 2, or 3 substituents independently selected from the group consisting of halogen, hydroxyl, oxo, $C_{1-6}$ alkyl, $C_{1-6}$ haloalkyl, $C_{3-7}$ cycloalkyl, $C_{1-4}$ alkoxyl, and $C_{1-4}$ haloalkoxyl. In certain embodiments, Ring A is a $C_{5-6}$ saturated carbocyclic ring optionally substituted with 1, 2, or 3 substituents independently selected from the group consisting of halogen, hydroxyl, oxo, $C_{1-6}$ alkyl, $C_{1-6}$ haloalkyl, $C_{3-7}$ cycloalkyl, $C_{1-4}$ alkoxyl, and $C_{1-4}$ haloalkoxyl. In certain embodiments, Ring A is a $C_{3-8}$ saturated or partially unsaturated carbocyclic ring. In certain embodiments, Ring A is a $C_{5-6}$ saturated carbocyclic ring.

In certain embodiments, Ring A is a 3-8 membered saturated or partially unsaturated heterocyclic ring optionally substituted with 1, 2, or 3 substituents independently selected from the group consisting of halogen, hydroxyl, oxo, $C_{1-6}$ alkyl, $C_{1-6}$ haloalkyl, $C_{3-7}$ cycloalkyl, $C_{1-4}$ alkoxyl, and $C_{1-4}$ haloalkoxyl. In certain embodiments, Ring A is a 5-6 membered saturated heterocyclic ring optionally substituted with 1, 2, or 3 substituents independently selected from the group consisting of halogen, hydroxyl, oxo, $C_{1-6}$ alkyl, $C_{1-6}$ haloalkyl, $C_{3-7}$ cycloalkyl, $C_{1-4}$ alkoxyl, and $C_{1-4}$ haloalkoxyl. In certain embodiments, Ring A is a 3-8 membered saturated or partially unsaturated heterocyclic ring. In certain embodiments, Ring A is a 5-6 membered saturated heterocyclic ring.

In certain embodiments, Ring A is

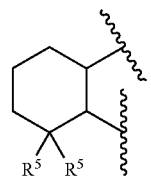

wherein $R^5$ represents independently for each occurrence hydrogen, $C_{1-6}$ alkyl, $C_{1-6}$ haloalkyl, or $C_{3-7}$ cycloalkyl. In certain embodiments, Ring A is

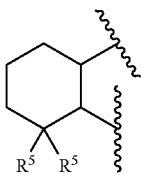

wherein R⁵ represents independently for each occurrence $C_{1-6}$ alkyl or $C_{3-7}$ cycloalkyl. In certain embodiments, Ring A is

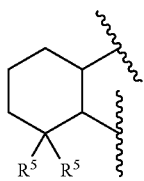

wherein R⁵ is $C_{1-6}$ alkyl.

The description above describes multiple embodiments relating to compounds of Formula III. The patent application specifically contemplates all combinations of the embodiments.

Another aspect of the invention provides a compound represented by Formula IV:

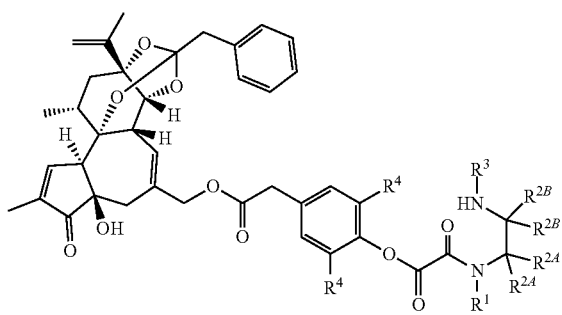

(IV)

or a pharmaceutically acceptable salt thereof; wherein:

R¹ is hydrogen, $C_{1-6}$ alkyl, $C_{1-6}$ haloalkyl, $C_{3-7}$ cycloalkyl, $C_6$ aryl, or 4-8 membered heterocycloalkyl; or R¹ and an occurrence of $R^{2A}$ are taken together with the atoms to which they are attached to form a 3-8 membered saturated heterocyclic ring optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

$R^{2A}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl; or two occurrences of $R^{2A}$ are taken together to represent an oxo group; or two occurrences of $R^{2A}$ are taken together with the carbon atom to which they are attached to form a 3-6 membered saturated carbocyclic or heterocyclic ring; or an occurrence of $R^{2A}$ and an occurrence of $R^{2B}$ are taken together with the carbon atoms to which they are attached to form a 3-6 membered saturated carbocyclic or heterocyclic ring;

$R^{2B}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl; or two occurrences of $R^{2B}$ are taken together to represent an oxo group; or two occurrences of $R^{2B}$ are taken together with the carbon atom to which they are attached to form a 3-6 membered saturated carbocyclic or heterocyclic ring;

R³ is hydrogen, $C_{1-6}$ alkyl, $C_{1-6}$ haloalkyl, $C_{3-7}$ cycloalkyl, 4-8 membered heterocycloalkyl, or —C(=NH)—NH₂; wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl; and R⁴ represents independently for each occurrence hydrogen, halogen, $C_{1-4}$ alkyl, $C_{1-4}$ haloalkyl, $C_{1-4}$ alkoxyl, or $C_{1-4}$ haloalkoxyl.

The definitions of variables in Formula IV above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula IV in the form of a pharmaceutically acceptable salt. In certain embodiments, the compound is a compound of Formula IV.

In certain embodiments, R¹ is hydrogen, $C_{1-6}$ alkyl, $C_{1-6}$ haloalkyl, $C_{3-7}$ cycloalkyl, $C_6$ aryl, or 3-8 membered heterocycloalkyl. In certain embodiments, R¹ is $C_{1-4}$ alkyl or $C_{1-4}$ haloalkyl.

In certain embodiments, R¹ and an occurrence of $R^{2A}$ are taken together with the atoms to which they are attached to form a 3-8 membered saturated heterocyclic ring optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, R¹ and an occurrence of $R^{2A}$ are taken together with the atoms to which they are attached to form a 3-8 membered saturated heterocyclic ring optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, R¹ and an occurrence of $R^{2A}$ are taken together with the atoms to which they are attached to form a 3-8 membered saturated heterocyclic ring. In certain embodiments, R¹ and an occurrence of $R^{2A}$ are taken together to represent —(CH₂)₂—C(R⁶)₂—ψ, wherein ψ is a bond to the nitrogen atom; and R⁶ represents independently for each occurrence hydrogen or methyl; or both occurrences of R⁶ are taken together with the carbon atom to which they are attached to form a 3-membered saturated carbocyclic ring. In certain embodiments, R¹ and an occurrence of $R^{2A}$ are taken together with the atoms to which they are attached to form a 3-8 membered saturated heterocyclic ring.

In certain embodiments, $R^{2A}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl. In certain embodiments, $R^{2A}$ represents independently for each occurrence hydrogen, $C_{1-4}$ alkyl, or $C_{1-4}$ haloalkyl. In certain embodiments, $R^{2A}$ represents independently for each occurrence hydrogen, $C_{1-4}$ alkyl, or $C_{1-4}$ haloalkyl; or two occurrences of $R^{2A}$ are taken together with the carbon atom to which they are attached to form a 3-membered saturated carbocyclic ring. In certain embodiments, two occurrences of $R^{2A}$ are taken together to represent an oxo group.

In certain embodiments, two occurrences of $R^{2A}$ are taken together with the carbon atom to which they are attached to form a 3-6 membered saturated carbocyclic or heterocyclic ring. In certain embodiments, two occurrences of $R^{2A}$ are taken together with the carbon atom to which they are attached to form a 3-6 membered saturated carbocyclic ring. In certain embodiments, two occurrences of $R^{2A}$ are taken together with the carbon atom to which they are attached to form a 3-membered saturated carbocyclic ring. In certain embodiments, two occurrences of $R^{2A}$ are taken together with the carbon atom to which they are attached to form a 3-6 membered saturated heterocyclic ring.

In certain embodiments, an occurrence of $R^{2A}$ and an occurrence of $R^{2B}$ are taken together with the carbon atoms to which they are attached to form a 3-6 membered saturated carbocyclic or heterocyclic ring. In certain embodiments, an occurrence of $R^{2A}$ and an occurrence of $R^{2B}$ are taken together with the carbon atoms to which they are attached to form a 5-6 membered saturated carbocyclic ring. In certain embodiments, an occurrence of $R^{2A}$ and an occurrence of $R^{2B}$ are taken together with the carbon atoms to which they are attached to form a 5-6 membered saturated heterocyclic ring.

In certain embodiments, $R^{2B}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl. In certain embodiments, $R^{2B}$ represents independently for each occurrence hydrogen, $C_{1-4}$ alkyl, or $C_{1-4}$ haloalkyl. In certain embodiments, $R^{2B}$ represents independently for each occurrence hydrogen, $C_{1-4}$ alkyl, or $C_{1-4}$ haloalkyl; or two occurrences of $R^{2B}$ are taken together with the carbon atom to which they are attached to form a 3-membered saturated carbocyclic ring. In certain embodiments, two occurrences of $R^{2B}$ are taken together to represent an oxo group.

In certain embodiments, two occurrences of $R^{2B}$ are taken together with the carbon atom to which they are attached to form a 3-6 membered saturated carbocyclic or heterocyclic ring. In certain embodiments, two occurrences of $R^{2B}$ are taken together with the carbon atom to which they are attached to form a 3-6 membered saturated carbocyclic ring. In certain embodiments, two occurrences of $R^{2B}$ are taken together with the carbon atom to which they are attached to form a 3-membered saturated carbocyclic ring. In certain embodiments, two occurrences of $R^{2B}$ are taken together with the carbon atom to which they are attached to form a 3-6 membered saturated heterocyclic ring.

In certain embodiments, $R^3$ is hydrogen. In certain embodiments, $R^3$ is $C_{1-6}$ alkyl, $C_{1-6}$ haloalkyl, or $C_{3-7}$ cycloalkyl. In certain embodiments, $R^3$ is $C_{1-6}$ alkyl or $C_{1-6}$ haloalkyl. In certain embodiments, $R^3$ is $C_{1-6}$ alkyl. In certain embodiments, $R^3$ is $C_{1-6}$ haloalkyl. In certain embodiments, $R^3$ is $C_{3-7}$ cycloalkyl. In certain embodiments, $R^3$ is 4-8 membered heterocycloalkyl. In certain embodiments, $R^3$ is —C(=NH)—NH$_2$.

In certain embodiments, $R^3$ is $C_{3-7}$ cycloalkyl or 4-8 membered heterocycloalkyl, each of which is optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is $C_{3-7}$ cycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is 4-8 membered heterocycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl.

In certain embodiments, $R^4$ represents independently for each occurrence hydrogen, halogen, or $C_{1-4}$ alkoxyl. In certain embodiments, $R^4$ represents independently for each occurrence hydrogen, iodo, or methoxy. In certain embodiments, one occurrence of $R^4$ is methoxy, and the other occurrence of $R^4$ is hydrogen. In certain embodiments, $R^4$ is hydrogen. In certain embodiments, one occurrence of $R^4$ is methoxy, and the other occurrence of $R^4$ is iodo.

The description above describes multiple embodiments relating to compounds of Formula IV. The patent application specifically contemplates all combinations of the embodiments.

Another aspect of the invention provides a compound represented by Formula V:

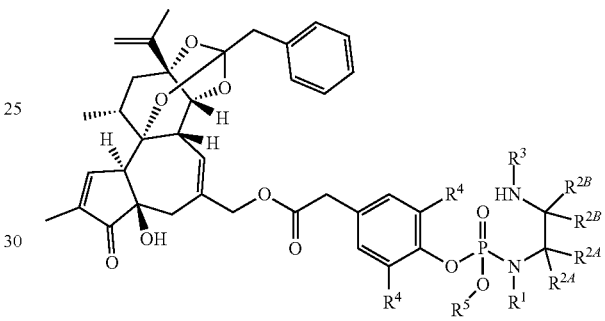

(V)

or a pharmaceutically acceptable salt thereof; wherein:

$R^1$ is hydrogen, $C_{1-6}$ alkyl, $C_{1-6}$ haloalkyl, $C_{3-7}$ cycloalkyl, $C_6$ aryl, or 4-8 membered heterocycloalkyl; or $R^1$ and an occurrence of $R^{2A}$ are taken together with the atoms to which they are attached to form a 3-8 membered saturated heterocyclic ring optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

$R^{2A}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl; or two occurrences of $R^{2A}$ are taken together to represent an oxo group; or two occurrences of $R^{2A}$ are taken together with the carbon atom to which they are attached to form a 3-6 membered saturated carbocyclic or heterocyclic ring; or an occurrence of $R^{2A}$ and an occurrence of $R^{2B}$ are taken together with the carbon atoms to which they are attached to form a 3-6 membered saturated carbocyclic or heterocyclic ring;

$R^{2B}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl; or two occurrences of $R^{2B}$ are taken together to represent an oxo group; or two occurrences of $R^{2B}$ are taken together with the carbon atom to which they are attached to form a 3-6 membered saturated carbocyclic or heterocyclic ring;

$R^3$ is hydrogen, $C_{1-6}$ alkyl, $C_{1-6}$ haloalkyl, $C_{3-7}$ cycloalkyl, 4-8 membered heterocycloalkyl, or —C(=NH)—NH$_2$; wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

$R^4$ represents independently for each occurrence hydrogen, halogen, $C_{1-4}$ alkyl, $C_{1-4}$ haloalkyl, $C_{1-4}$ alkoxyl, or $C_{1-4}$ haloalkoxyl; and $R^5$ is hydrogen, $C_{1-6}$ alkyl, $C_{1-6}$ haloalkyl, $C_{3-7}$ cycloalkyl, $C_6$ aryl, or 3-8 membered heterocyclyl.

The definitions of variables in Formula V above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula V in the form of a pharmaceutically acceptable salt. In certain embodiments, the compound is a compound of Formula V.

In certain embodiments, $R^1$ is hydrogen, $C_{1-6}$ alkyl, $C_{1-6}$ haloalkyl, $C_{3-7}$ cycloalkyl, $C_6$ aryl, or 3-8 membered heterocycloalkyl. In certain embodiments, $R^1$ is $C_{1-4}$ alkyl or $C_{1-4}$ haloalkyl.

In certain embodiments, $R^1$ and an occurrence of $R^{2A}$ are taken together with the atoms to which they are attached to form a 3-8 membered saturated heterocyclic ring optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^1$ and an occurrence of $R^{2A}$ are taken together with the atoms to which they are attached to form a 3-8 membered saturated heterocyclic ring optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^1$ and an occurrence of $R^{2A}$ are taken together with the atoms to which they are attached to form a 3-8 membered saturated heterocyclic ring. In certain embodiments, $R^1$ and an occurrence of $R^{2A}$ are taken together to represent —$(CH_2)_2$—$C(R^6)_2$—ψ, wherein ψ is a bond to the nitrogen atom; and $R^6$ represents independently for each occurrence hydrogen or methyl; or both occurrences of $R^6$ are taken together with the carbon atom to which they are attached to form a 3-membered saturated carbocyclic ring. In certain embodiments, $R^1$ and an occurrence of $R^{2A}$ are taken together with the atoms to which they are attached to form a 3-8 membered saturated heterocyclic ring.

In certain embodiments, $R^{2A}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl. In certain embodiments, $R^{2A}$ represents independently for each occurrence hydrogen, $C_{1-4}$ alkyl, or $C_{1-4}$ haloalkyl. In certain embodiments, $R^{2A}$ represents independently for each occurrence hydrogen, $C_{1-4}$ alkyl, or $C_{1-4}$ haloalkyl; or two occurrences of $R^{2A}$ are taken together with the carbon atom to which they are attached to form a 3-membered saturated carbocyclic ring. In certain embodiments, two occurrences of $R^{2A}$ are taken together to represent an oxo group.

In certain embodiments, two occurrences of $R^{2A}$ are taken together with the carbon atom to which they are attached to form a 3-6 membered saturated carbocyclic or heterocyclic ring. In certain embodiments, two occurrences of $R^{2A}$ are taken together with the carbon atom to which they are attached to form a 3-6 membered saturated carbocyclic ring. In certain embodiments, two occurrences of $R^{2A}$ are taken together with the carbon atom to which they are attached to form a 3-membered saturated carbocyclic ring. In certain embodiments, two occurrences of $R^{2A}$ are taken together with the carbon atom to which they are attached to form a 3-6 membered saturated heterocyclic ring.

In certain embodiments, an occurrence of $R^{2A}$ and an occurrence of $R^{2B}$ are taken together with the carbon atoms to which they are attached to form a 3-6 membered saturated carbocyclic or heterocyclic ring. In certain embodiments, an occurrence of $R^{2A}$ and an occurrence of $R^{2B}$ are taken together with the carbon atoms to which they are attached to form a 5-6 membered saturated carbocyclic ring. In certain embodiments, an occurrence of $R^{2A}$ and an occurrence of $R^{2B}$ are taken together with the carbon atoms to which they are attached to form a 5-6 membered saturated heterocyclic ring.

In certain embodiments, $R^{2B}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl. In certain embodiments, $R^{2B}$ represents independently for each occurrence hydrogen, $C_{1-4}$ alkyl, or $C_{1-4}$ haloalkyl. In certain embodiments, $R^{2B}$ represents independently for each occurrence hydrogen, $C_{1-4}$ alkyl, or $C_{1-4}$ haloalkyl; or two occurrences of $R^{2B}$ are taken together with the carbon atom to which they are attached to form a 3-membered saturated carbocyclic ring. In certain embodiments, two occurrences of $R^{2B}$ are taken together to represent an oxo group.

In certain embodiments, two occurrences of $R^{2B}$ are taken together with the carbon atom to which they are attached to form a 3-6 membered saturated carbocyclic or heterocyclic ring. In certain embodiments, two occurrences of $R^{2B}$ are taken together with the carbon atom to which they are attached to form a 3-6 membered saturated carbocyclic ring. In certain embodiments, two occurrences of $R^{2B}$ are taken together with the carbon atom to which they are attached to form a 3-membered saturated carbocyclic ring. In certain embodiments, two occurrences of $R^{2B}$ are taken together with the carbon atom to which they are attached to form a 3-6 membered saturated heterocyclic ring.

In certain embodiments, $R^3$ is hydrogen. In certain embodiments, $R^3$ is $C_{1-6}$ alkyl, $C_{1-6}$ haloalkyl, or $C_{3-7}$ cycloalkyl. In certain embodiments, $R^3$ is $C_{1-6}$ alkyl or $C_{1-6}$ haloalkyl. In certain embodiments, $R^3$ is $C_{1-6}$ alkyl. In certain embodiments, $R^3$ is $C_{1-6}$ haloalkyl. In certain embodiments, $R^3$ is $C_{3-7}$ cycloalkyl. In certain embodiments, $R^3$ is 4-8 membered heterocycloalkyl. In certain embodiments, $R^3$ is —C(=NH)—$NH_2$.

In certain embodiments, $R^3$ is $C_{3-7}$ cycloalkyl or 4-8 membered heterocycloalkyl, each of which is optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is $C_{3-7}$ cycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl. In certain embodiments, $R^3$ is 4-8 membered heterocycloalkyl optionally substituted with 1 or 2 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl.

In certain embodiments, $R^4$ represents independently for each occurrence hydrogen, halogen, or $C_{1-4}$ alkoxyl. In certain embodiments, $R^4$ represents independently for each occurrence hydrogen, iodo, or methoxy. In certain embodiments, one occurrence of $R^4$ is methoxy, and the other occurrence of $R^4$ is hydrogen. In certain embodiments, $R^4$ is hydrogen. In certain embodiments, one occurrence of $R^4$ is methoxy, and the other occurrence of $R^4$ is iodo.

In certain embodiments, $R^5$ is hydrogen. In certain embodiments, $R^5$ is $C_{1-6}$ alkyl, $C_{1-6}$ haloalkyl, or $C_{3-7}$ cycloalkyl.

The description above describes multiple embodiments relating to compounds of Formula V. The patent application specifically contemplates all combinations of the embodiments.

In certain other embodiments, the compound is one of the compounds listed in Tables 1-5A below, or a pharmaceutically acceptable salt thereof. In certain embodiments, the compound is one of the compounds listed in Tables 1-5A below.

TABLE 1

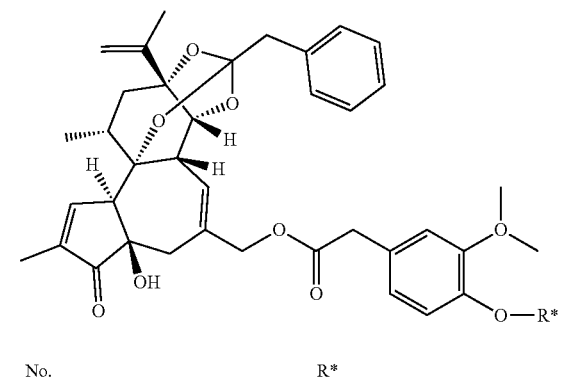

| No. | R* |
|---|---|
| I-1 | |
| I-2 | |
| I-3 | |
| I-4 | |

TABLE 1-continued

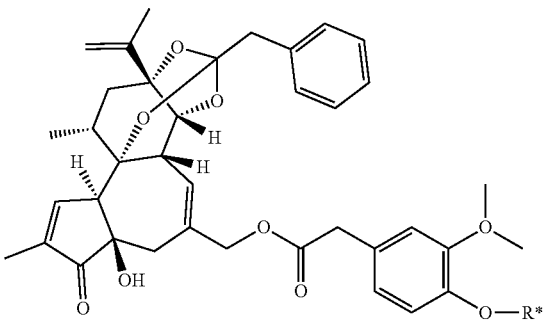

| No. | R* |
|---|---|
| I-5 | |
| I-6 | |
| I-7 | |
| I-8 | |
| I-9 | |
| I-10 | |

TABLE 1-continued
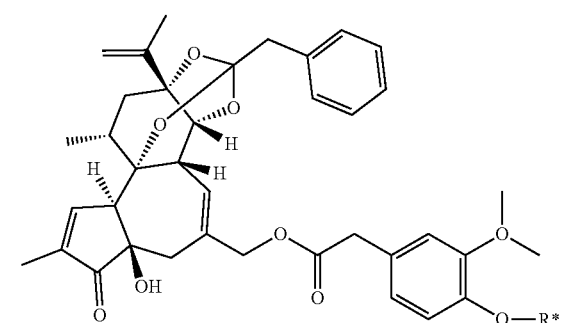
| No. | R* |
|---|---|
| I-11 | 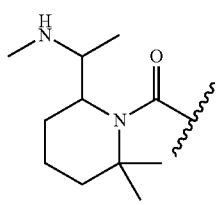 [SMILES: *C(=O)N1C(C(C)NC)CCCC1(C)C] |
| I-12 | 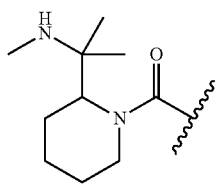 [SMILES: *C(=O)N1CCCCC1C(C)(C)NC] |
| I-13 | 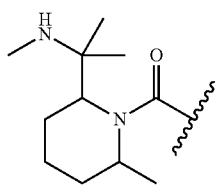 [SMILES: *C(=O)N1C(C)CCCC1C(C)(C)NC] |
| I-14 | 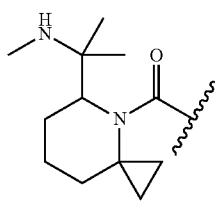 [SMILES: *C(=O)N1C(C(C)(C)NC)CCCC12CC2] |
| I-15 | 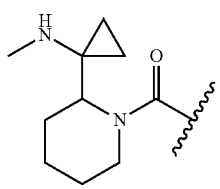 [SMILES: *C(=O)N1CCCCC1C1(NC)CC1] |
| I-16 | 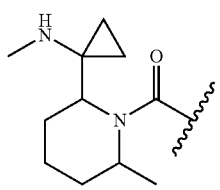 [SMILES: *C(=O)N1C(C)CCCC1C1(NC)CC1] |
TABLE 1-continued
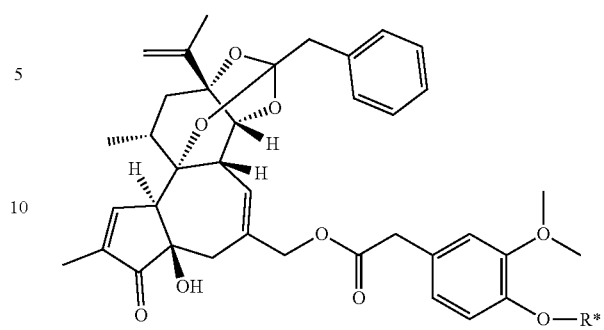
| No. | R* |
|---|---|
| I-17 | 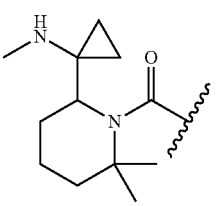 [SMILES: *C(=O)N1C(C2(NC)CC2)CCCC1(C)C] |
| I-18 | 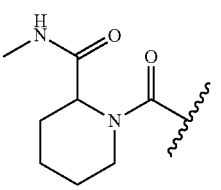 [SMILES: *C(=O)N1CCCCC1C(=O)NC] |
| I-19 | 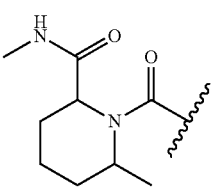 [SMILES: *C(=O)N1C(C)CCCC1C(=O)NC] |
| I-20 | 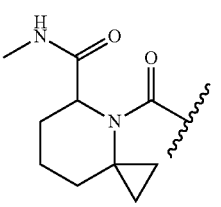 [SMILES: *C(=O)N1C(C(=O)NC)CCCC12CC2] |
| I-21 | 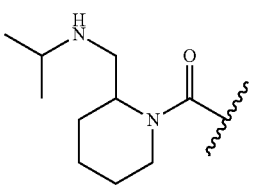 [SMILES: *C(=O)N1CCCCC1CNC(C)C] |
| I-22 | 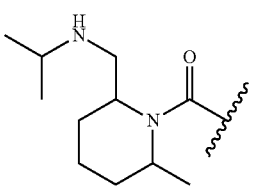 [SMILES: *C(=O)N1C(C)CCCC1CNC(C)C] |

TABLE 1-continued
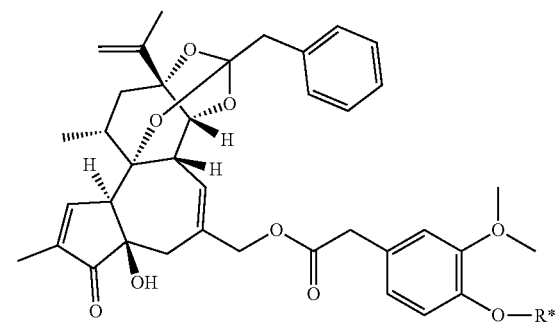
| No. | R* |
|---|---|
| I-23 | 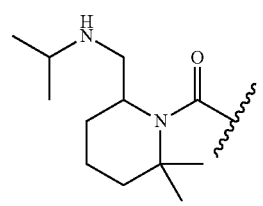 [SMILES: *C(=O)N1C(CNC(C)C)CCCC1(C)C] |
| I-24 | 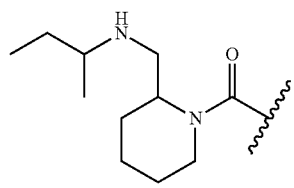 [SMILES: *C(=O)N1CCCCC1CNC(C)CC] |
| I-25 | 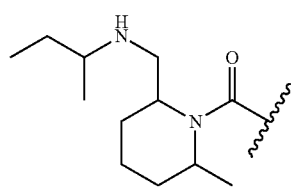 [SMILES: *C(=O)N1C(C)CCCC1CNC(C)CC] |
| I-26 | 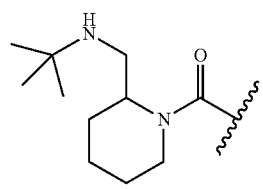 [SMILES: *C(=O)N1CCCCC1CNC(C)(C)C] |
| I-27 | 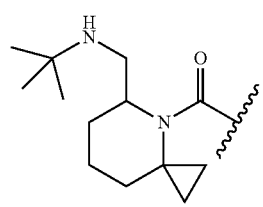 [SMILES: *C(=O)N1C(CNC(C)(C)C)CCCC12CC2] |
| I-28 | 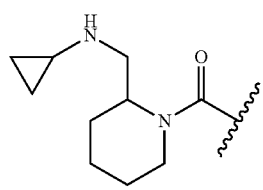 [SMILES: *C(=O)N1CCCCC1CNC1CC1] |
TABLE 1-continued
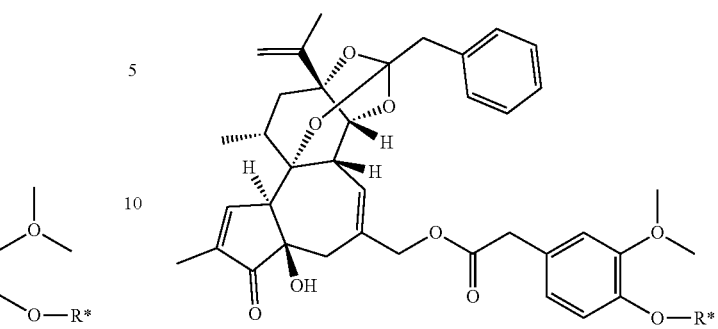
| No. | R* |
|---|---|
| I-29 | 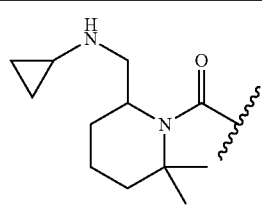 |
| I-30 | 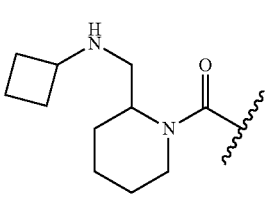 [SMILES: *C(=O)N1CCCCC1CNC1CCC1] |
| I-31 | 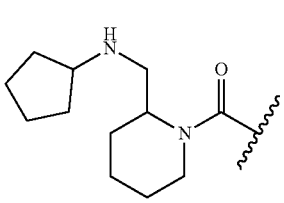 [SMILES: *C(=O)N1CCCCC1CNC1CCCC1] |
| I-32 | 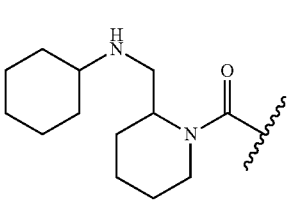 [SMILES: *C(=O)N1CCCCC1CNC1CCCCC1] |
| I-33 | 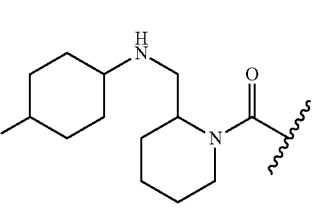 |
| I-34 | 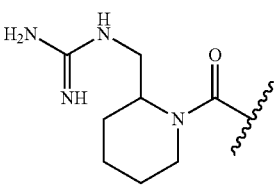 [SMILES: *C(=O)N1CCCCC1CNC(=N)N] |

TABLE 1-continued
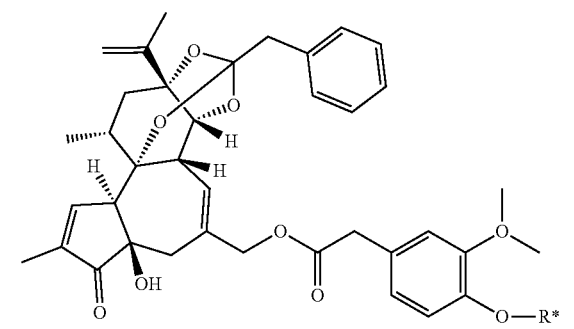
| No. | R* |
|---|---|
| I-35 | 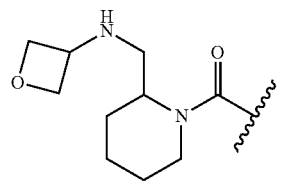 [SMILES: *C(=O)N1CCCCC1CNC1COC1] |
| I-36 | 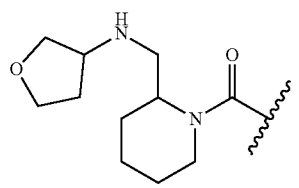 [SMILES: *C(=O)N1CCCCC1CNC1CCOC1] |
| I-37 | 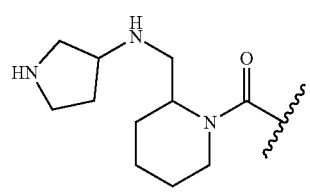 [SMILES: *C(=O)N1CCCCC1CNC1CCNC1] |
| I-38 | 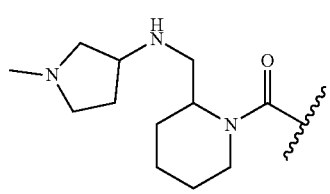 [SMILES: *C(=O)N1CCCCC1CNC1CCN(C)C1] |
| I-39 | 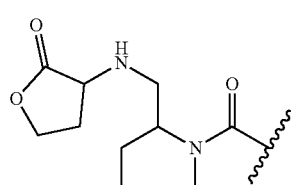 |
| I-40 | 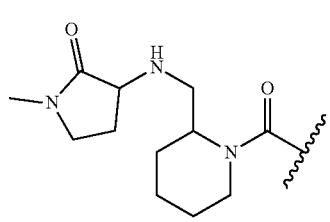 [SMILES: *C(=O)N1CCCCC1CNC1CCN(C)C1=O] |
TABLE 1-continued
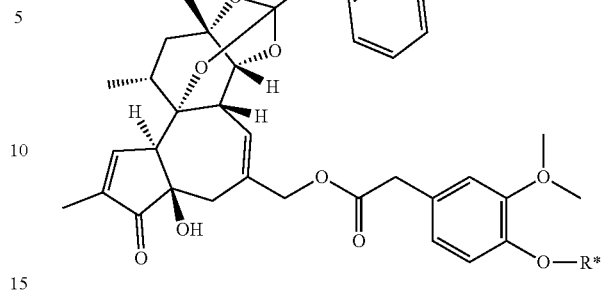
| No. | R* |
|---|---|
| I-41 | 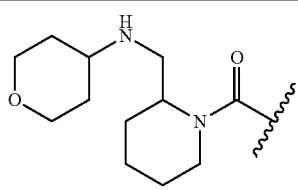 |
| I-42 | 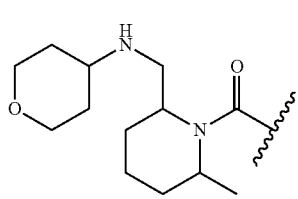 [SMILES: *C(=O)N1C(C)CCCC1CNC1CCOCC1] |
| I-43 | 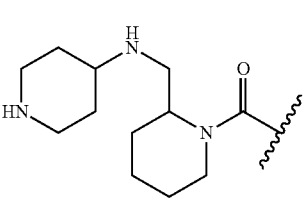 [SMILES: *C(=O)N1CCCCC1CNC1CCNCC1] |
| I-44 | 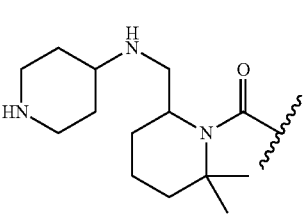 [SMILES: *C(=O)N1C(CNC2CCNCC2)CCCC1(C)C] |
| I-45 | 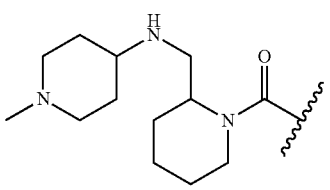 [SMILES: *C(=O)N1CCCCC1CNC1CCN(C)CC1] |
| I-46 | 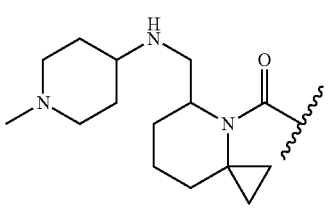 |

TABLE 1-continued
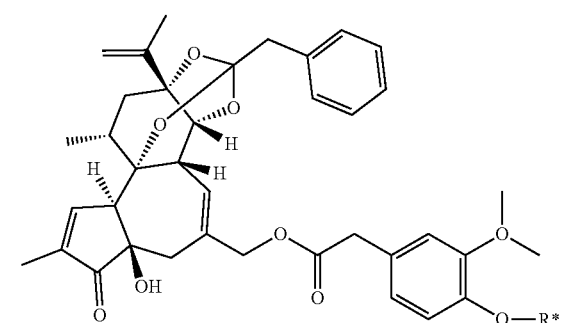
| No. | R* |
|---|---|
| I-47 | 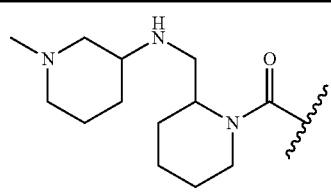 |
| I-48 | 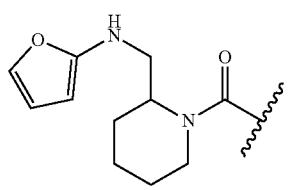 [SMILES: *C(=O)N1CCCCC1CNc1ccco1] |
| I-49 | 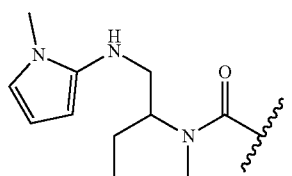 |
| I-50 | 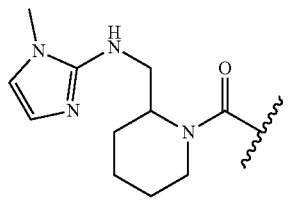 [SMILES: *C(=O)N1CCCCC1CNc1cccn1C] |
| I-51 | 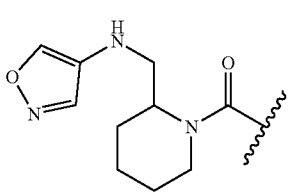 [SMILES: *C(=O)N1CCCCC1CNc1cnoc1] |
| I-52 | 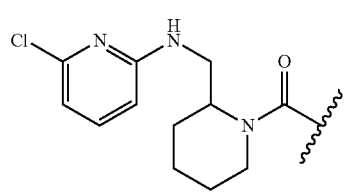 [SMILES: *C(=O)N1CCCCC1CNc1cccc(Cl)n1] |
TABLE 1-continued
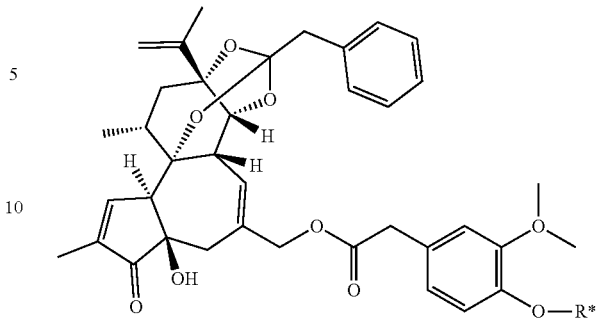
| No. | R* |
|---|---|
| I-53 | 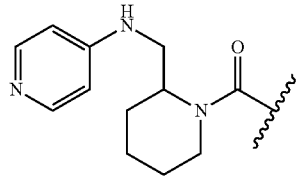 [SMILES: *C(=O)N1CCCCC1CNc1ccncc1] |
| I-54 | 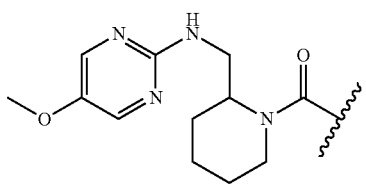 [SMILES: *C(=O)N1CCCCC1CNc1ncc(OC)cn1] |
| I-55 | 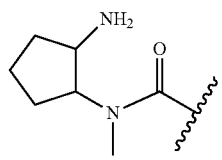 [SMILES: *C(=O)N(C)C1CCCC1N] |
| I-56 | 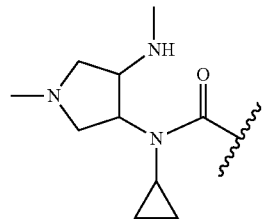 [SMILES: *C(=O)N(C1CC1)C1CN(C)CC1NC] |
| I-57 | 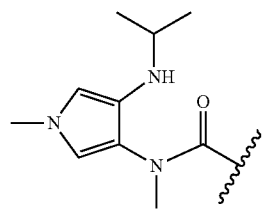 [SMILES: *C(=O)N(C)c1cn(C)cc1NC(C)C] |
| I-58 | 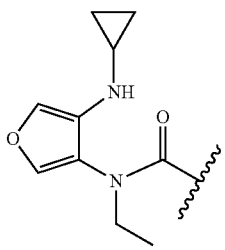 [SMILES: *C(=O)N(CC)c1cocc1NC1CC1] |

TABLE 1-continued
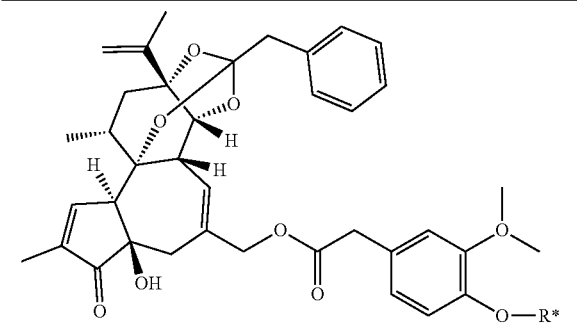
| No. | R* |
|---|---|
| I-59 | 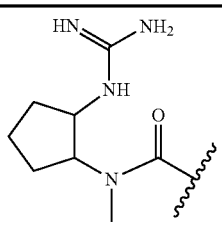 |
| I-60 | 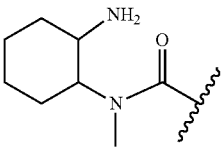 [SMILES: *C(=O)N(C)C1CCCCC1N] |
| I-61 | 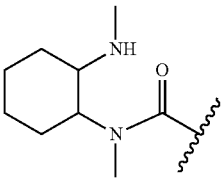 [SMILES: *C(=O)N(C)C1CCCCC1NC] |
| I-62 | 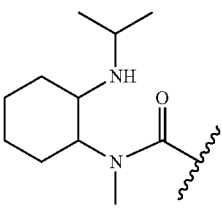 [SMILES: *C(=O)N(C)C1CCCCC1NC(C)C] |
| I-63 | 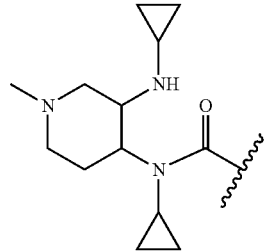 [SMILES: *C(=O)N(C1CC1)C1CCN(C)CC1NC1CC1] |
| I-64 | 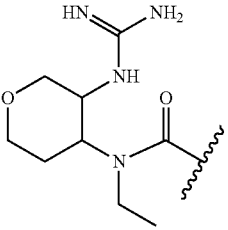 [SMILES: *C(=O)N(CC)C1CCOCC1NC(=N)N] |
TABLE 1-continued
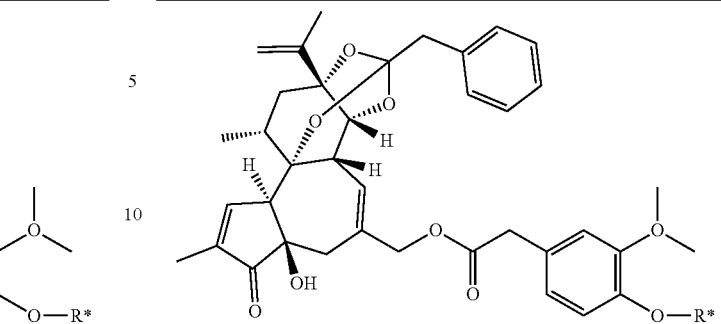
| No. | R* |
|---|---|
| I-65 | 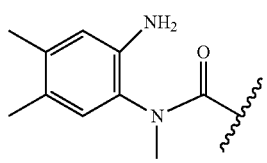 [SMILES: *C(=O)N(C)c1cc(C)c(C)cc1N] |
| I-66 | 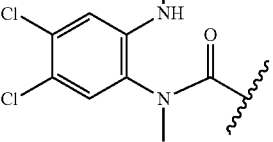 |
| I-67 | 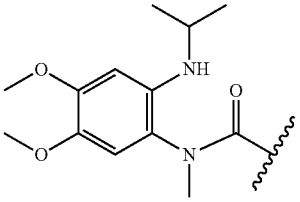 [SMILES: *C(=O)N(C)c1cc(OC)c(OC)cc1NC(C)C] |
| I-68 | 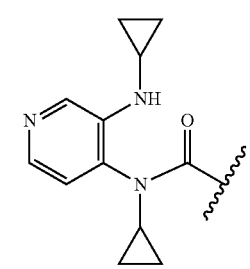 [SMILES: *C(=O)N(c1ccncc1NC1CC1)C1CC1] |
| I-69 | 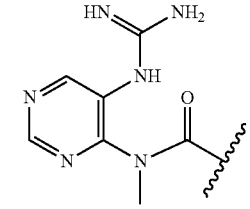 [SMILES: *C(=O)N(C)c1ncncc1NC(=N)N] |
| I-70 | 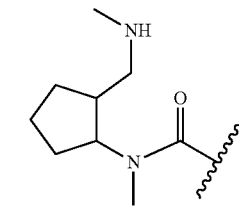 [SMILES: *C(=O)N(C)C1CCCC1CNC] |

TABLE 1-continued
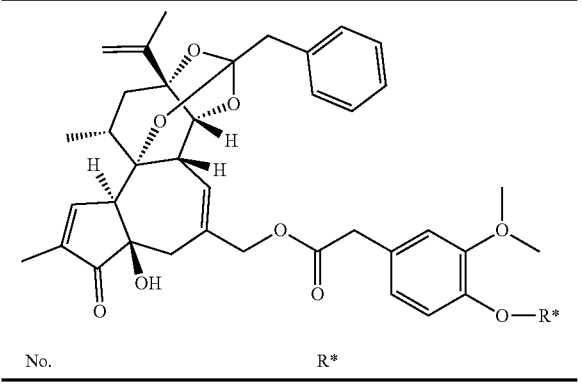
| No. | R* |
|---|---|
| I-71 | 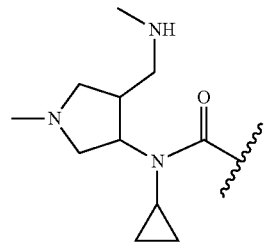 [SMILES: *C(=O)N(C1CC1)C1CN(C)CC1CNC] |
| I-72 | 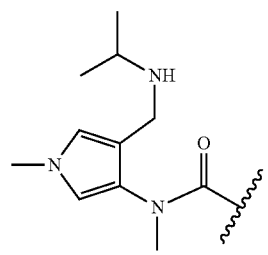 [SMILES: *C(=O)N(C)c1cn(C)cc1CNC(C)C] |
| I-73 | 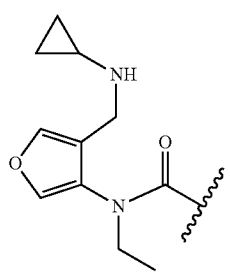 [SMILES: *C(=O)N(CC)c1cocc1CNC1CC1] |
| I-74 | 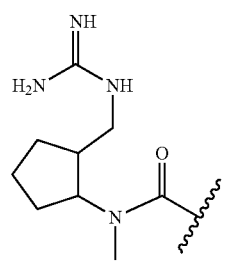 [SMILES: *C(=O)N(C)C1CCCC1CNC(=N)N] |
| I-75 | 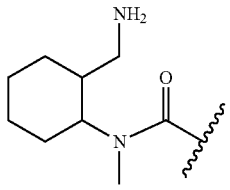 [SMILES: *C(=O)N(C)C1CCCCC1CN] |
TABLE 1-continued
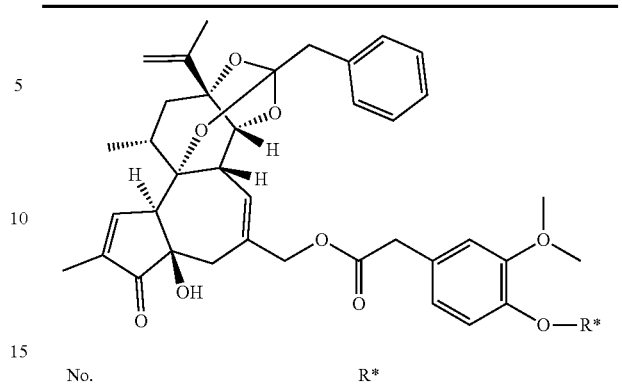
| No. | R* |
|---|---|
| I-76 | 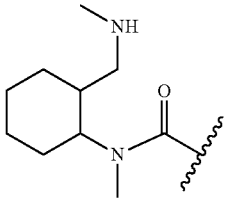 [SMILES: *C(=O)N(C)C1CCCCC1CNC] |
| I-77 | 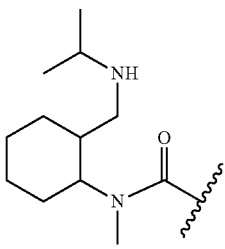 [SMILES: *C(=O)N(C)C1CCCCC1CNC(C)C] |
| I-78 | 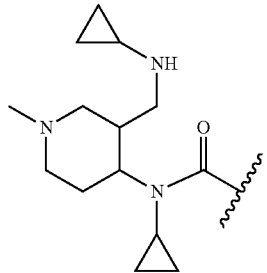 [SMILES: *C(=O)N(C1CC1)C1CCN(C)CC1CNC1CC1] |
| I-79 | 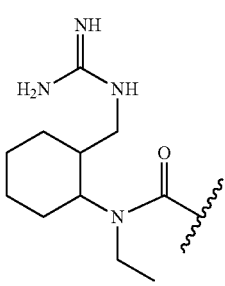 [SMILES: *C(=O)N(CC)C1CCCCC1CNC(=N)N] |
| I-80 | 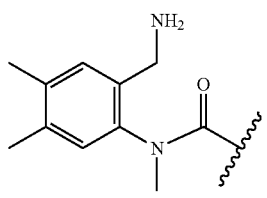 [SMILES: *C(=O)N(C)c1cc(C)c(C)cc1CN] |

TABLE 1-continued
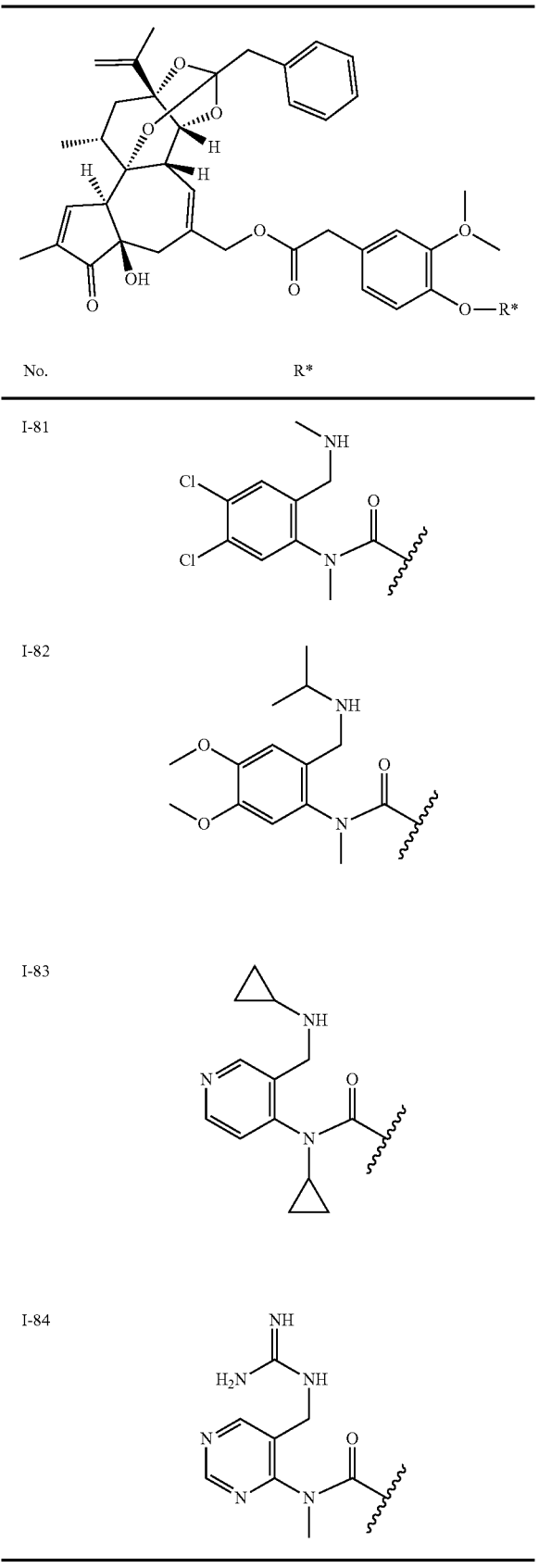
| No. | R* |
|---|---|
| I-81 | |
| I-82 | |
| I-83 | |
| I-84 | |
TABLE 1A
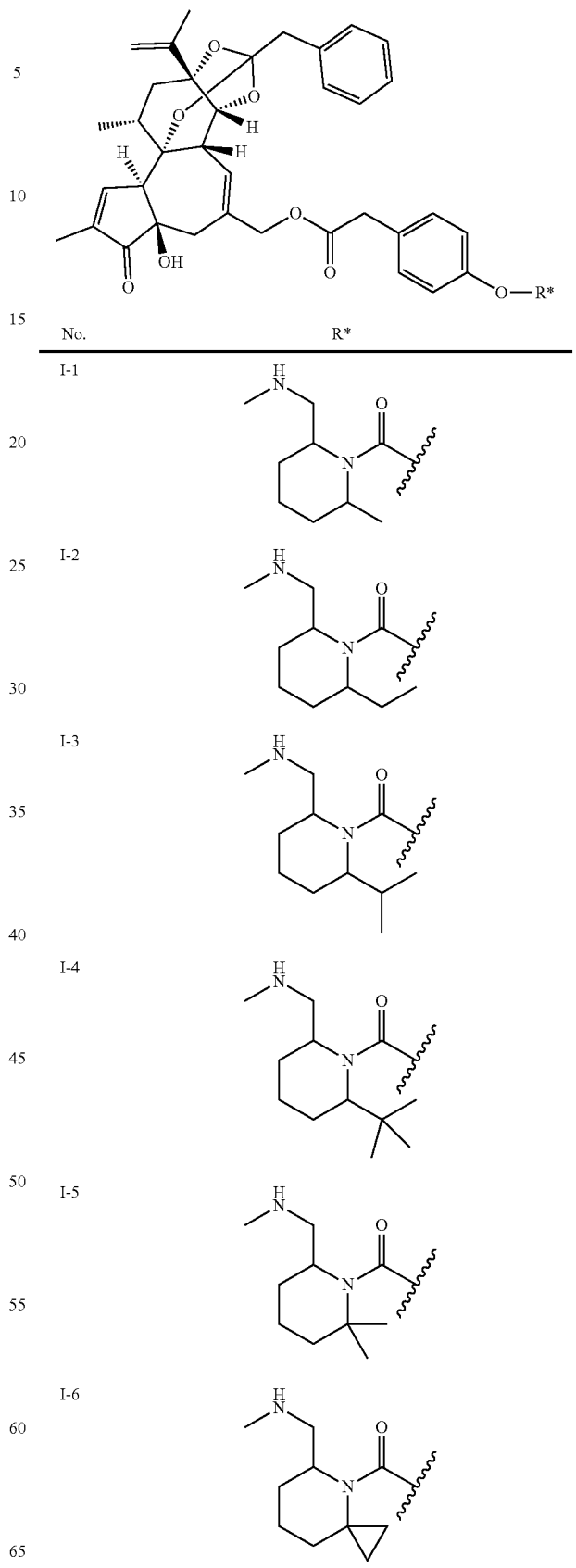
| No. | R* |
|---|---|
| I-1 | |
| I-2 | |
| I-3 | |
| I-4 | |
| I-5 | |
| I-6 | |

TABLE 1A-continued
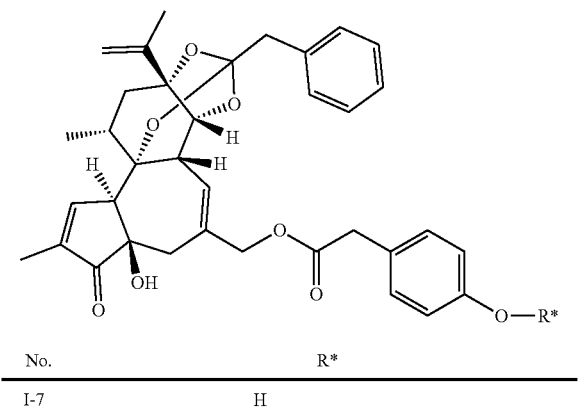
| No. | R* |
|---|---|
| I-7 | 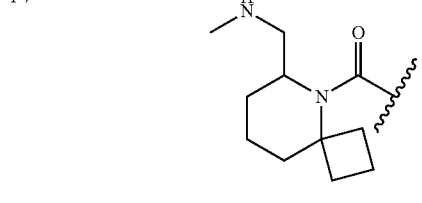 |
| I-8 | 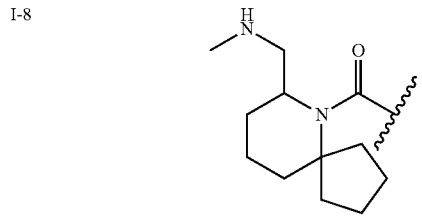 |
| I-9 | 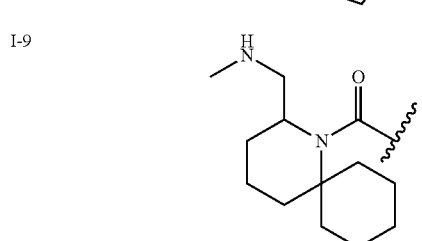 |
| I-10 | 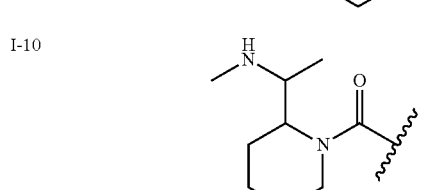 |
| I-11 | 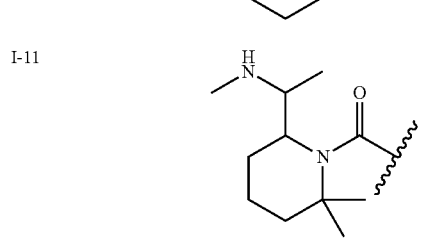 |
TABLE 1A-continued
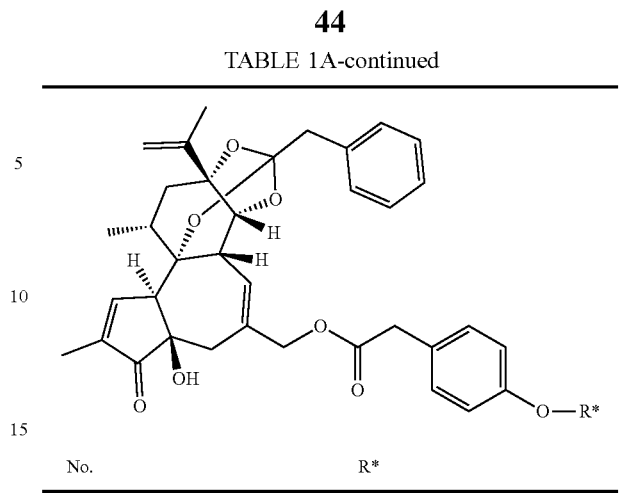
| No. | R* |
|---|---|
| I-13 | 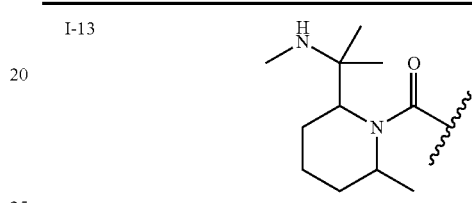 |
| I-14 | 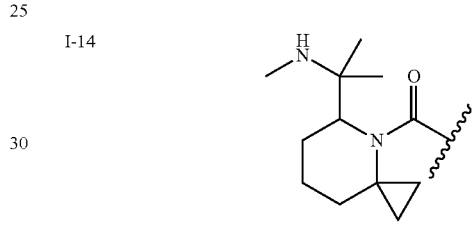 |
| I-15 | 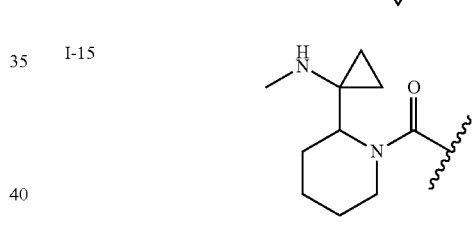 |
| I-16 | 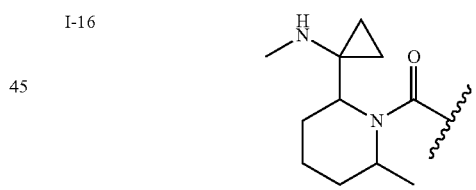 |
| I-17 | 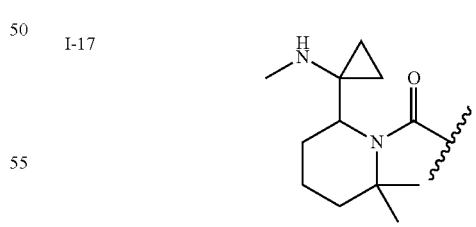 |
| I-18 | |

TABLE 1A-continued
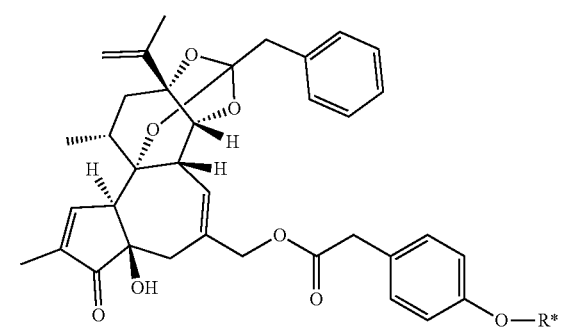
| No. | R* |
|---|---|
| I-19 | 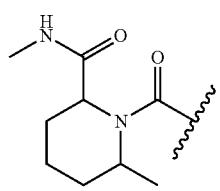 [SMILES: *C(=O)N1C(C)CCCC1C(=O)NC] |
| I-20 | 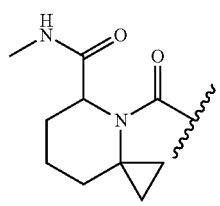 [SMILES: *C(=O)N1C(C(=O)NC)CCCC12CC2] |
| I-21 | 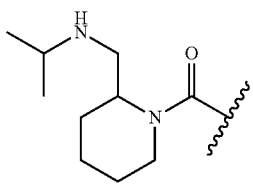 [SMILES: *C(=O)N1CCCCC1CNC(C)C] |
| I-22 | 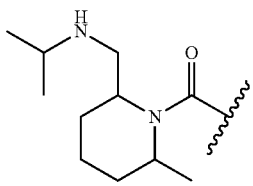 [SMILES: *C(=O)N1C(C)CCCC1CNC(C)C] |
| I-23 | 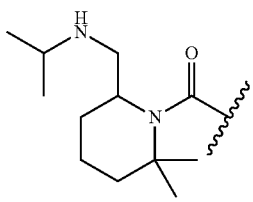 [SMILES: *C(=O)N1C(CNC(C)C)CCCC1(C)C] |
| I-24 | 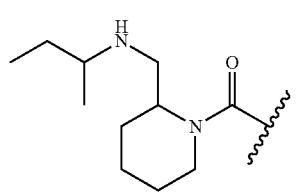 [SMILES: *C(=O)N1CCCCC1CNC(C)CC] |
TABLE 1A-continued
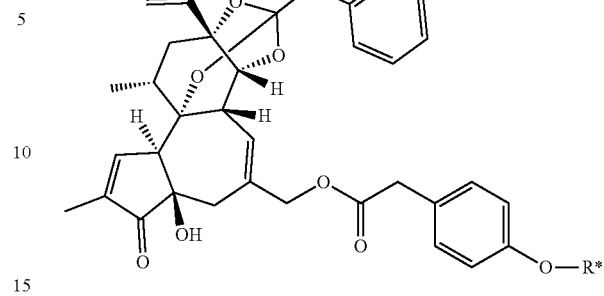
| No. | R* |
|---|---|
| I-25 | 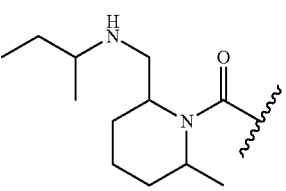 [SMILES: *C(=O)N1C(C)CCCC1CNC(C)CC] |
| I-26 | 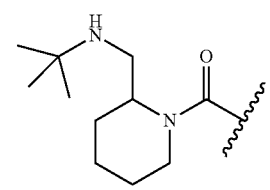 [SMILES: *C(=O)N1CCCCC1CNC(C)(C)C] |
| I-27 | 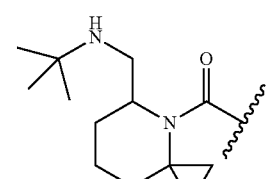 |
| I-28 | 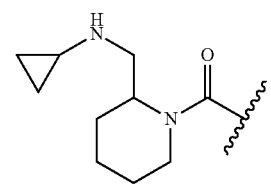 [SMILES: *C(=O)N1CCCCC1CNC1CC1] |
| I-29 | 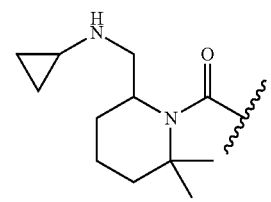 [SMILES: *C(=O)N1C(CNC2CC2)CCCC1(C)C] |
| I-30 | 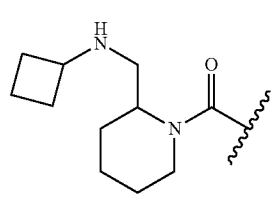 [SMILES: *C(=O)N1CCCCC1CNC1CCC1] |

TABLE 1A-continued
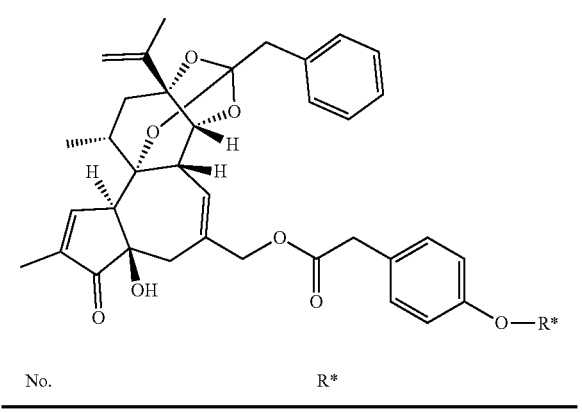
| No. | R* |
|---|---|
| I-31 | 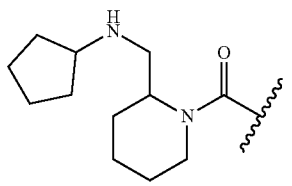 [SMILES: *C(=O)N1CCCCC1CNC1CCCC1] |
| I-32 | 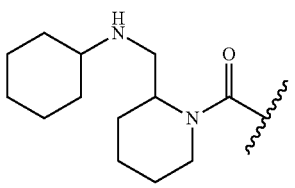 [SMILES: *C(=O)N1CCCCC1CNC1CCCCC1] |
| I-33 | 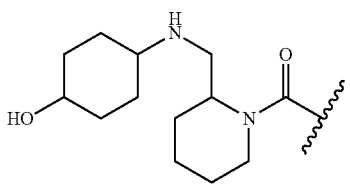 [SMILES: *C(=O)N1CCCCC1CNC1CCC(O)CC1] |
| I-34 | 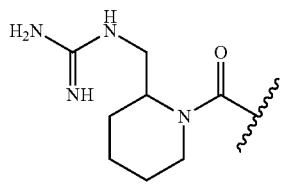 |
| I-35 | 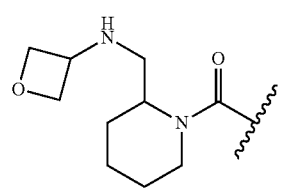 [SMILES: *C(=O)N1CCCCC1CNC1COC1] |
| I-36 | 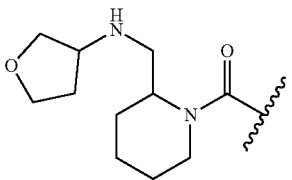 [SMILES: *C(=O)N1CCCCC1CNC1CCOC1] |
TABLE 1A-continued
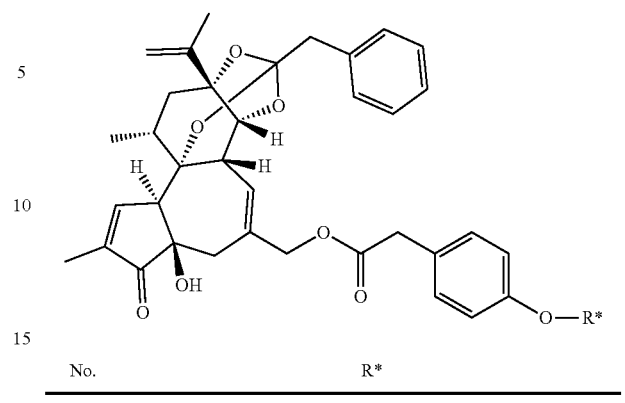
| No. | R* |
|---|---|
| I-37 | 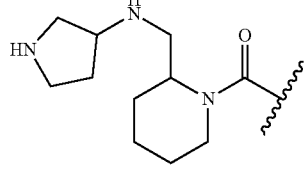 |
| I-38 | 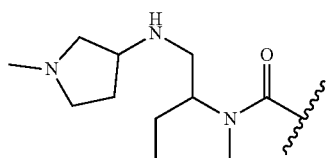 |
| I-39 | 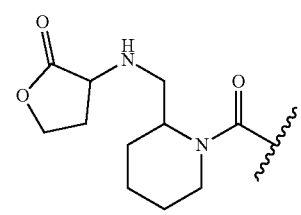 [SMILES: *C(=O)N1CCCCC1CNC1CCOC1=O] |
| I-40 | 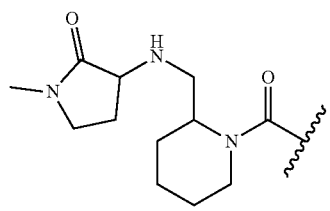 [SMILES: *C(=O)N1CCCCC1CNC1CCN(C)C1=O] |
| I-41 | 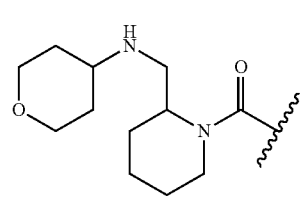 [SMILES: *C(=O)N1CCCCC1CNC1CCOCC1] |
| I-42 | 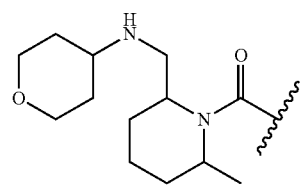 [SMILES: *C(=O)N1C(C)CCCC1CNC1CCOCC1] |

TABLE 1A-continued
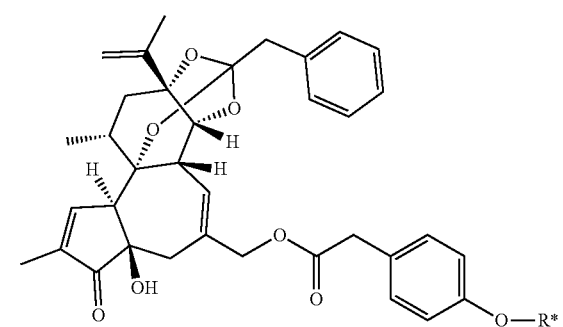
| No. | R* |
|---|---|
| I-43 | 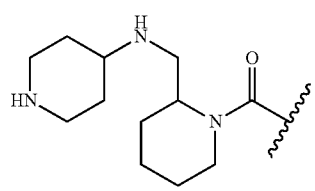 [SMILES: *C(=O)N1CCCCC1CNC1CCNCC1] |
| I-44 | 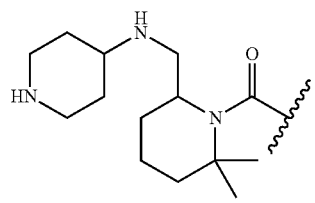 [SMILES: *C(=O)N1C(CNC2CCNCC2)CCCC1(C)C] |
| I-45 | 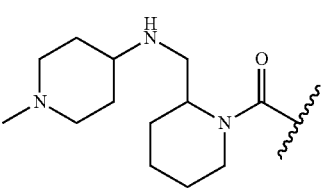 [SMILES: *C(=O)N1CCCCC1CNC1CCN(C)CC1] |
| I-46 | 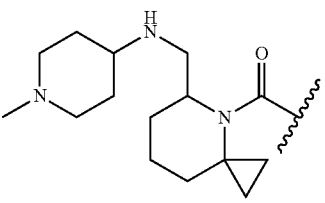 [SMILES: *C(=O)N1C(CNC2CCN(C)CC2)CCCC12CC2] |
| I-47 | 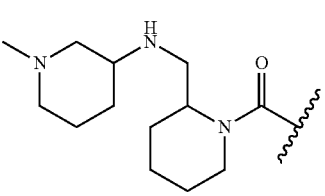 [SMILES: *C(=O)N1CCCCC1CNC1CCCN(C)C1] |
| I-48 | 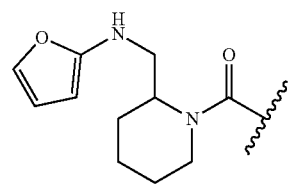 [SMILES: *C(=O)N1CCCCC1CNc1ccco1] |
TABLE 1A-continued
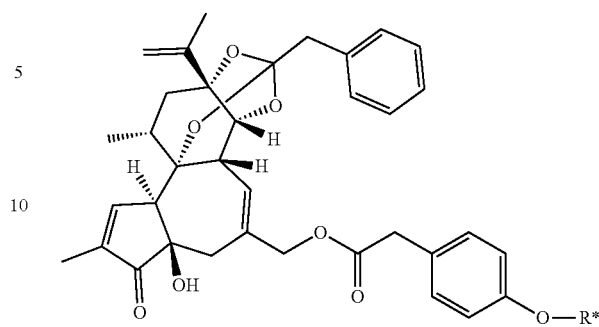
| No. | R* |
|---|---|
| I-49 | 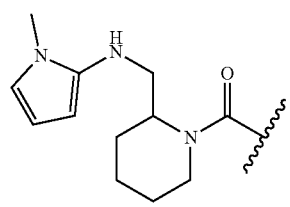 [SMILES: *C(=O)N1CCCCC1CNc1cccn1C] |
| I-50 | 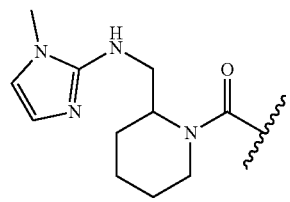 |
| I-51 | 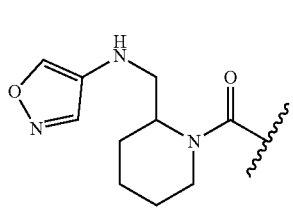 [SMILES: *C(=O)N1CCCCC1CNc1cnoc1] |
| I-52 | 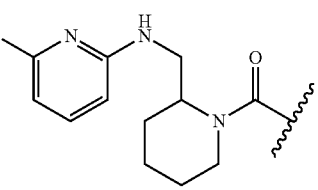 |
| I-53 | 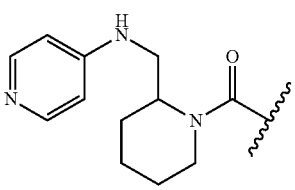 [SMILES: *C(=O)N1CCCCC1CNc1ccncc1] |
| I-54 | 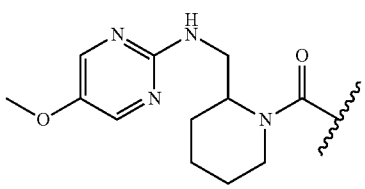 [SMILES: *C(=O)N1CCCCC1CNc1ncc(OC)cn1] |

TABLE 1A-continued

| No. | R* |
|---|---|
| I-55 | (2-aminocyclopentyl)-N-methyl |
| I-56 | (4-methylamino-1-methylpyrrolidin-3-yl)-N-cyclopropyl |
| I-57 | (4-isopropylamino-1-methylpyrrol-3-yl)-N-methyl |
| I-58 | (4-cyclopropylamino-furan-3-yl)-N-ethyl |
| I-59 | (2-guanidinocyclopentyl)-N-methyl |
| I-60 | (2-aminocyclohexyl)-N-methyl |
| I-61 | (2-methylaminocyclohexyl)-N-methyl |
| I-62 | (2-isopropylaminocyclohexyl)-N-methyl |
| I-63 | (3-cyclopropylamino-1-methylpiperidin-4-yl)-N-cyclopropyl |
| I-64 | (3-guanidino-tetrahydropyran-4-yl)-N-ethyl |
| I-65 | (2-amino-4,5-dimethylphenyl)-N-methyl |
| I-66 | (4,5-dichloro-2-methylaminophenyl)-N-methyl |

TABLE 1A-continued
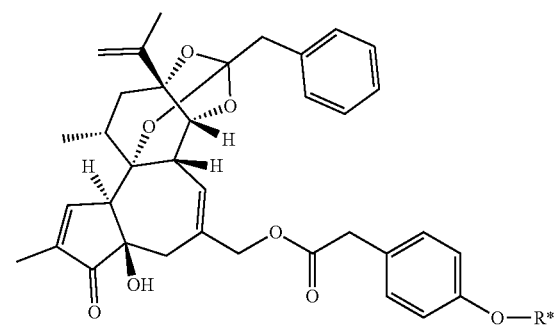
| No. | R* |
|---|---|
| I-67 | 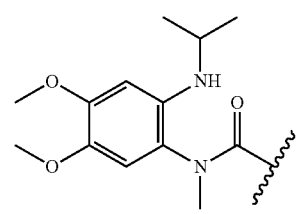 [SMILES: *C(=O)N(C)c1cc(OC)c(OC)cc1NC(C)C] |
| I-68 | 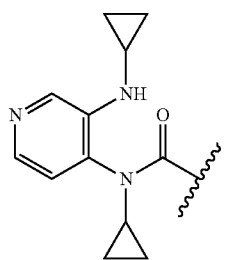 [SMILES: *C(=O)N(c1ccncc1NC1CC1)C1CC1] |
| I-69 | 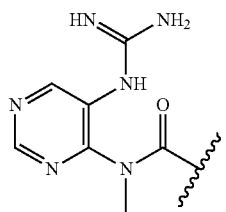 [SMILES: *C(=O)N(C)c1ncncc1NC(=N)N] |
| I-70 | 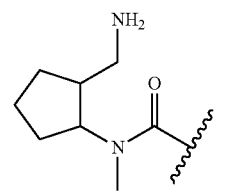 [SMILES: *C(=O)N(C)C1CCCC1CN] |
| I-71 | 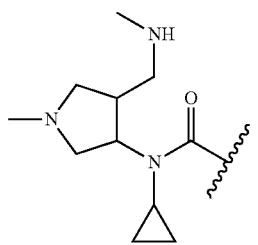 [SMILES: *C(=O)N(C1CC1)C1CN(C)CC1CNC] |
TABLE 1A-continued
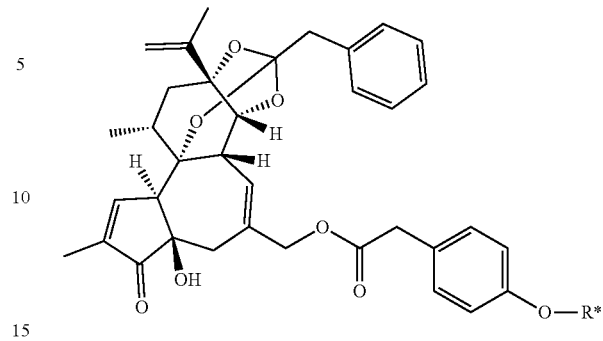
| No. | R* |
|---|---|
| I-72 | 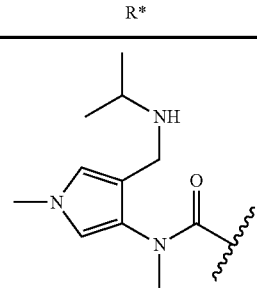 |
| I-73 | 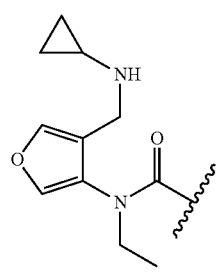 [SMILES: *C(=O)N(CC)c1cocc1CNC1CC1] |
| I-74 | 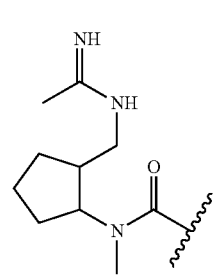 [SMILES: *C(=O)N(C)C1CCCC1CNC(C)=N] |
| I-75 | 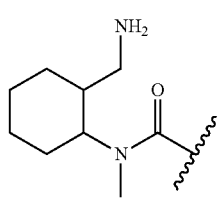 [SMILES: *C(=O)N(C)C1CCCCC1CN] |
| I-76 | 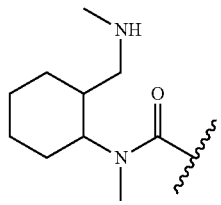 [SMILES: *C(=O)N(C)C1CCCCC1CNC] |

TABLE 1A-continued
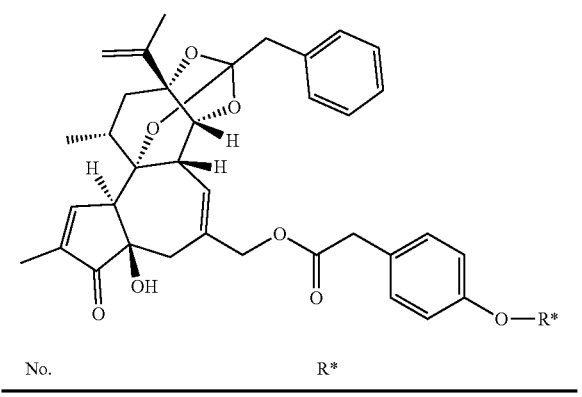
| No. | R* |
|---|---|
| I-77 | 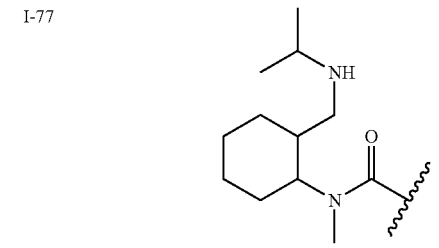 |
| I-78 | 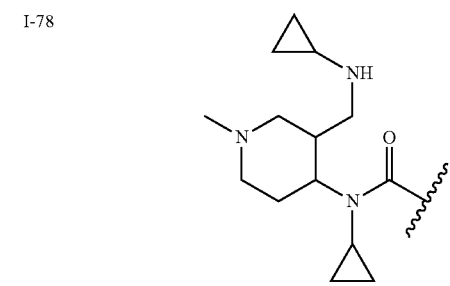 |
| I-79 | 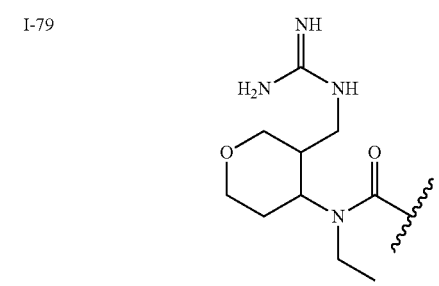 |
| I-80 | 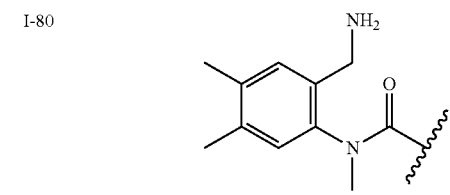 |
| I-81 | 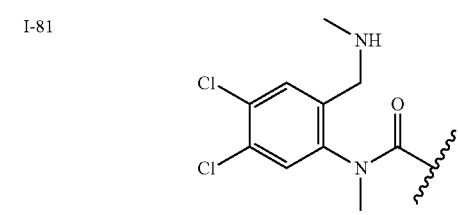 |
TABLE 1A-continued
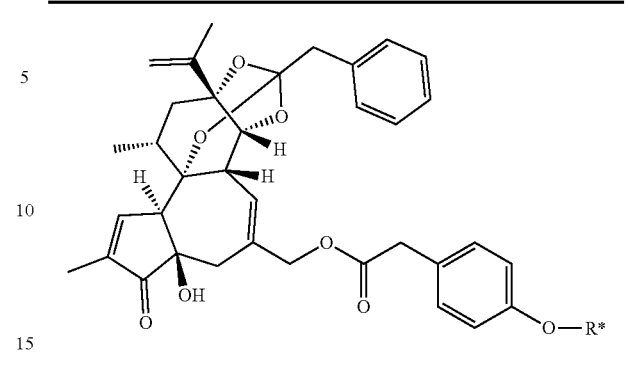
| No. | R* |
|---|---|
| I-82 | 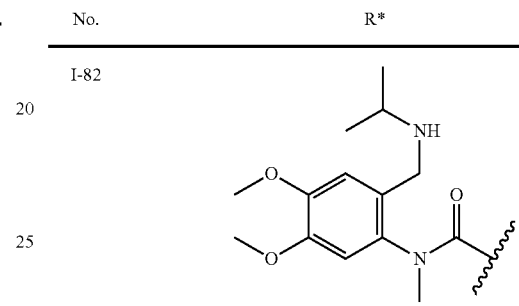 |
| I-83 | 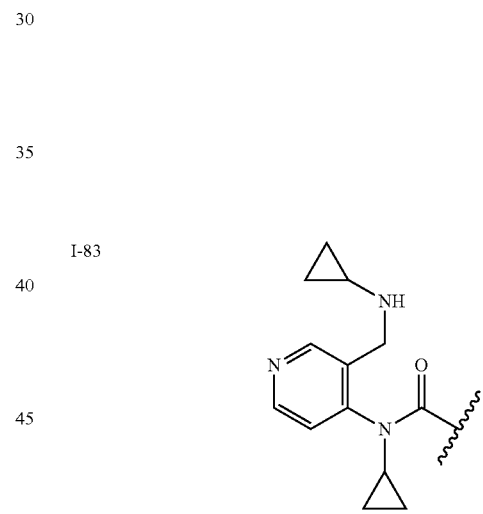 |
| I-84 | 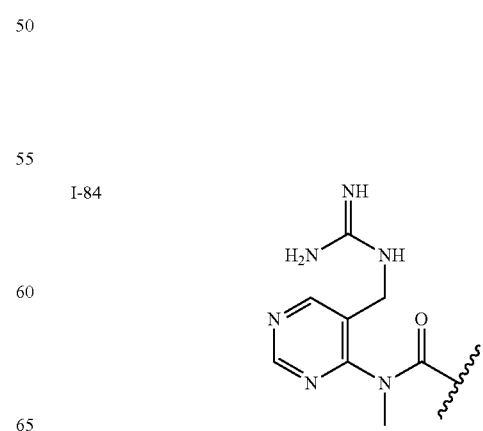 |

TABLE 2
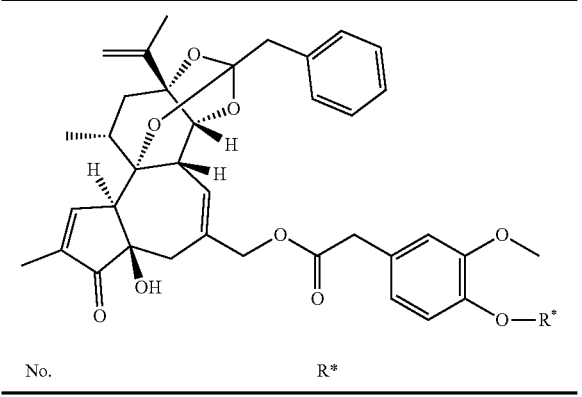
| No. | R* |
|---|---|
| II-1 | 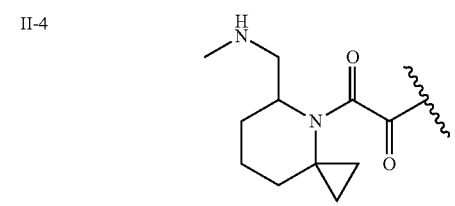 |
| II-2 | 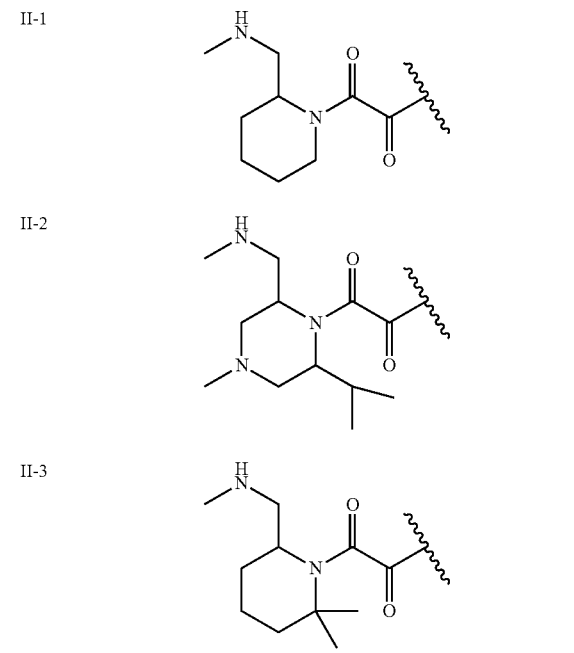 |
| II-3 | |
| II-4 | |
| II-5 | |
| II-6 | 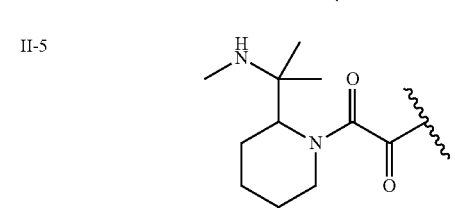 |
TABLE 2-continued
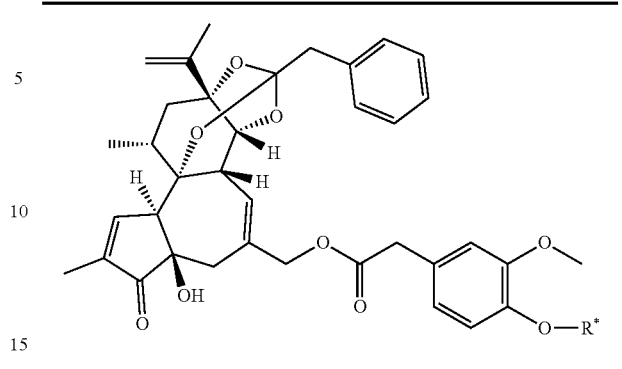
| No. | R* |
|---|---|
| II-7 | 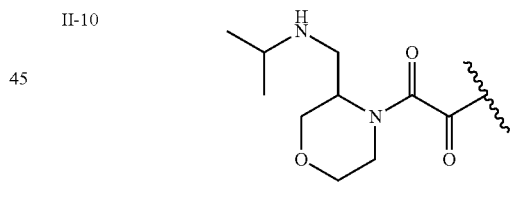 |
| II-8 | 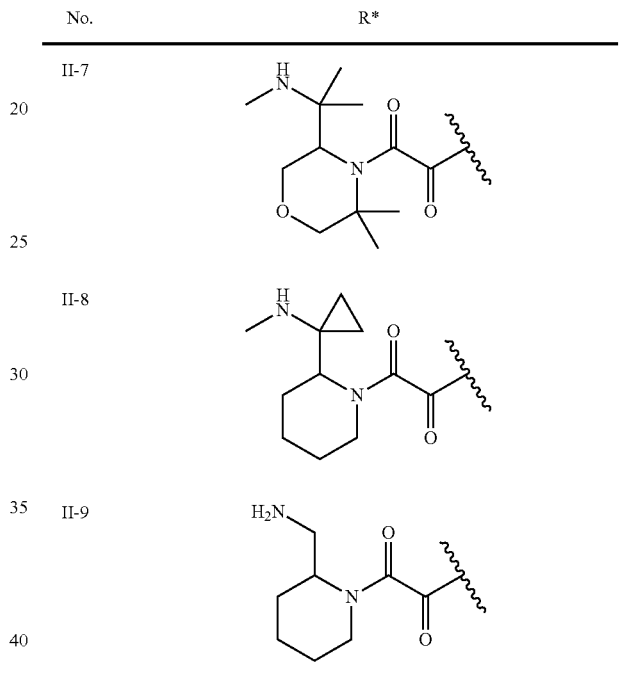 |
| II-9 | |
| II-10 | |
| II-11 | |
| II-12 | 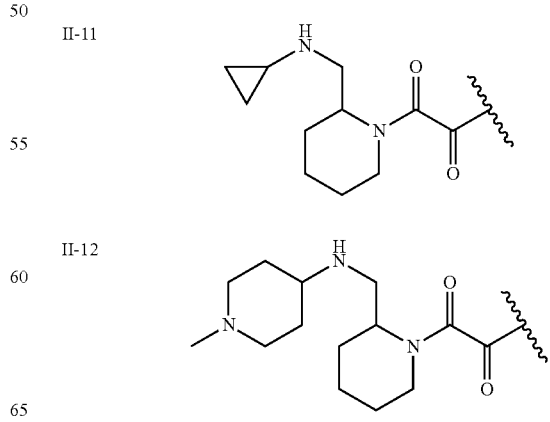 |

TABLE 2-continued
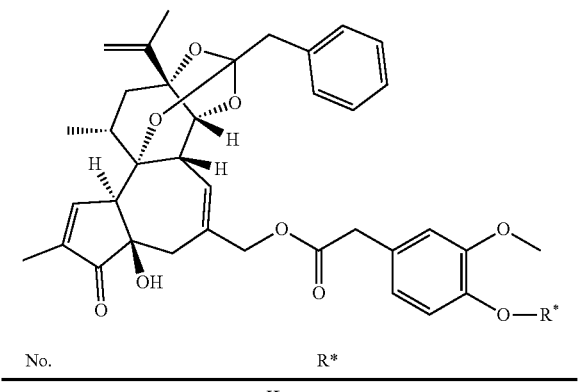
| No. | R* |
|---|---|
| II-13 | 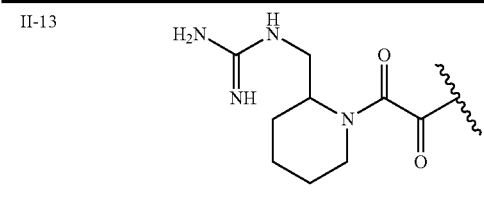 |
| II-14 | 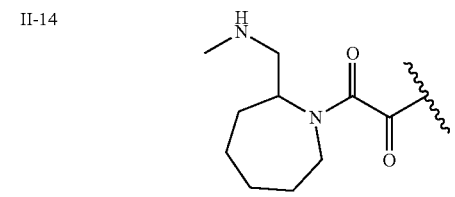 |
| II-15 | 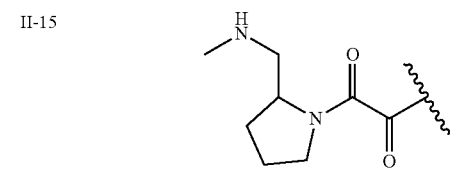 |
| II-16 | 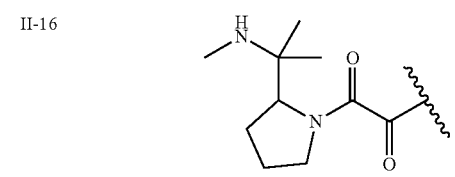 |
| II-17 | 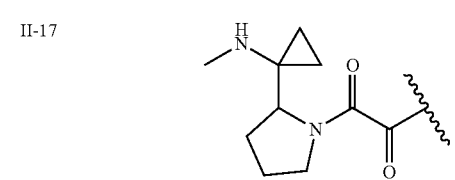 |
| II-18 | 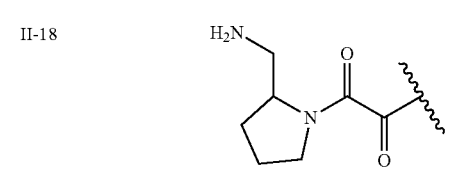 |
| II-19 | |
TABLE 2-continued
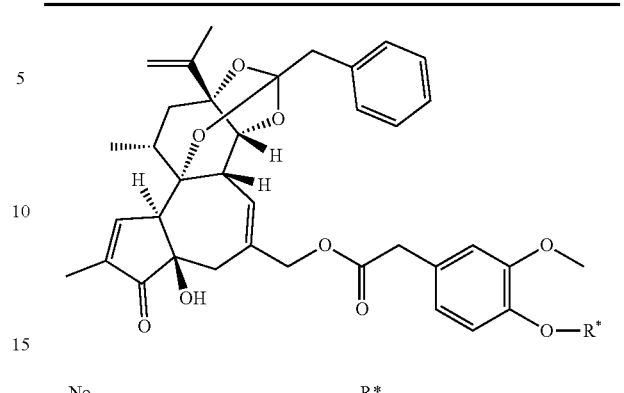
| No. | R* |
|---|---|
| II-20 | 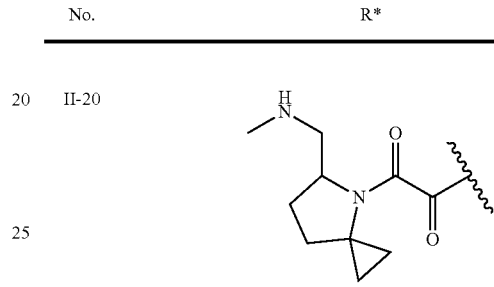 |
| II-21 | |
| II-22 | 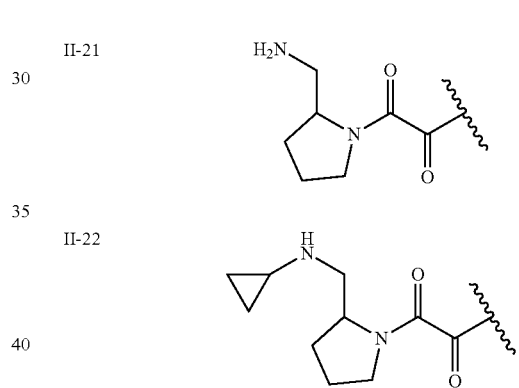 |
| II-23 | 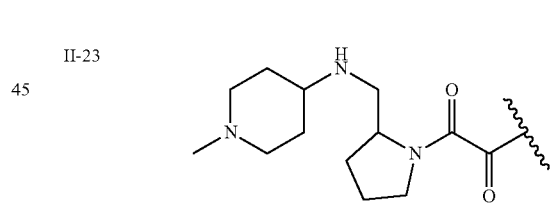 |
| II-24 | 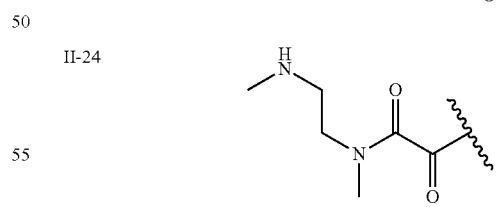 |
| II-25 | 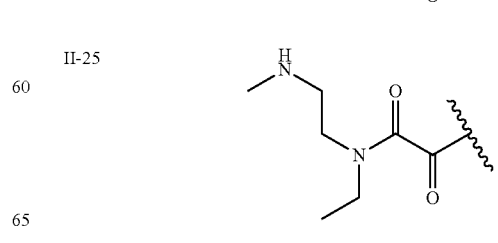 |

TABLE 2-continued
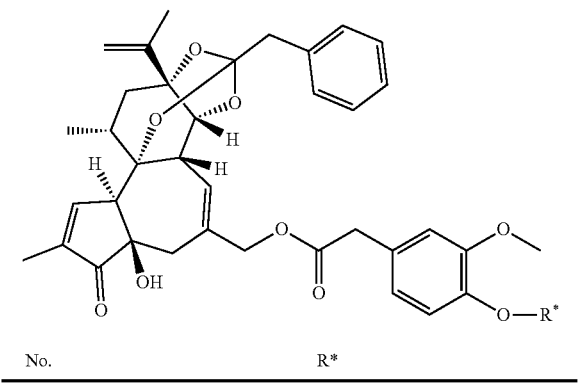
| No. | R* |
|---|---|
| II-26 | 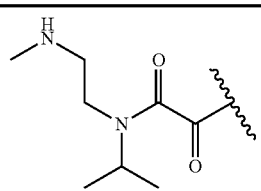 |
| II-27 | 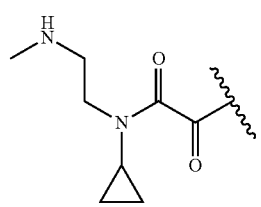 [SMILES: *C(=O)C(=O)N(CCNC)C1CC1] |
| II-28 | 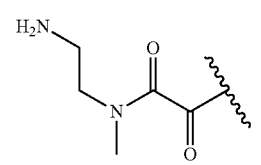 [SMILES: *C(=O)C(=O)N(C)CCN] |
| II-29 | 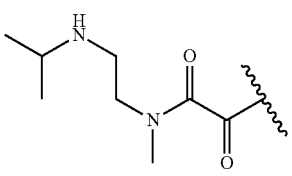 [SMILES: *C(=O)C(=O)N(C)CCNC(C)C] |
| II-30 | 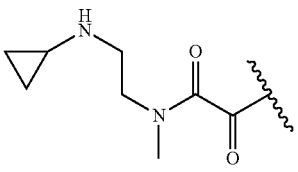 [SMILES: *C(=O)C(=O)N(C)CCNC1CC1] |
| II-31 | 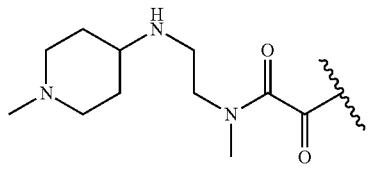 [SMILES: *C(=O)C(=O)N(C)CCNC1CCN(C)CC1] |
| II-32 | 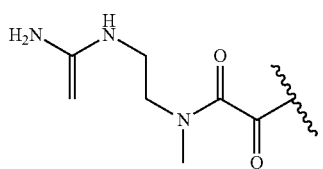 [SMILES: *C(=O)C(=O)N(C)CCNC(=C)N] |
TABLE 2-continued
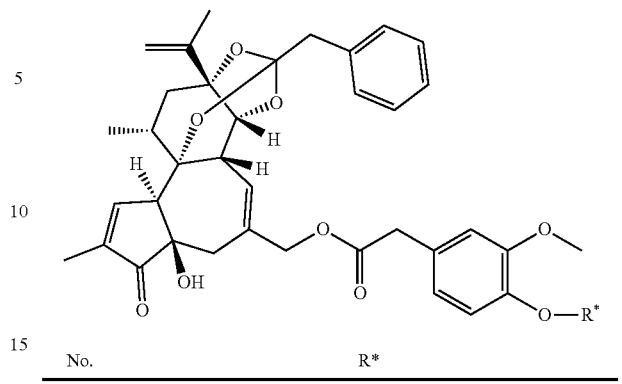
| No. | R* |
|---|---|
| II-33 | 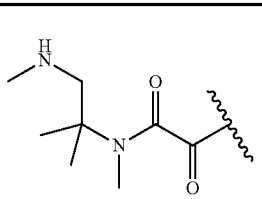 |
| II-34 | 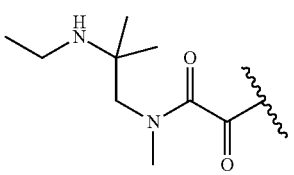 [SMILES: *C(=O)C(=O)N(C)CC(C)(C)NCC] |
| II-35 | 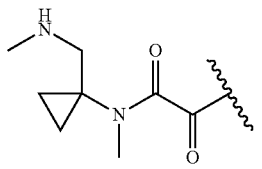 [SMILES: *C(=O)C(=O)N(C)C1(CNC)CC1] |
| II-36 | 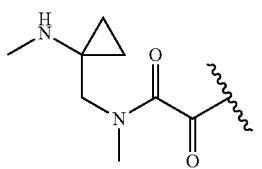 [SMILES: *C(=O)C(=O)N(C)CC1(NC)CC1] |
| II-37 | 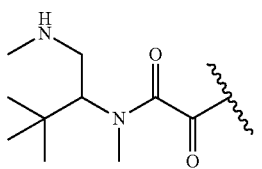 [SMILES: *C(=O)C(=O)N(C)C(CNC)C(C)(C)C] |
| II-38 | 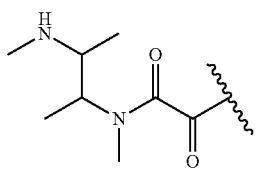 [SMILES: *C(=O)C(=O)N(C)C(C)C(C)NC] |
| II-39 | 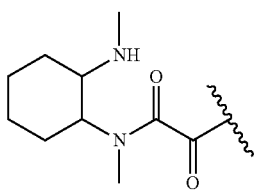 [SMILES: *C(=O)C(=O)N(C)C1CCCCC1NC] |

TABLE 2-continued
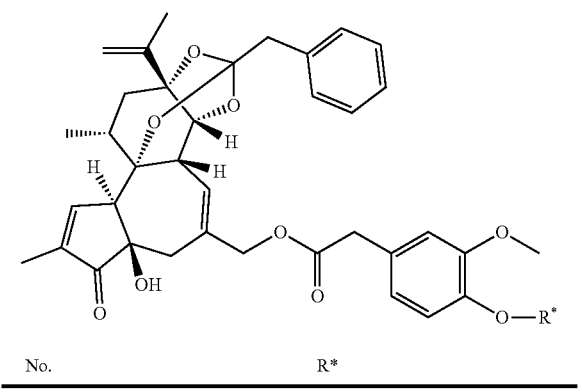
| No. | R* |
|---|---|
| II-40 | 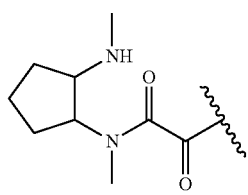 [SMILES: *C(=O)C(=O)N(C)C1CCCC1NC] |
| II-41 | 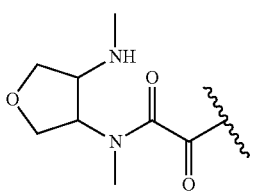 [SMILES: *C(=O)C(=O)N(C)C1COCC1NC] |
| II-42 | 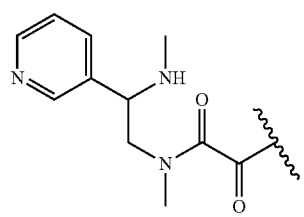 [SMILES: *C(=O)C(=O)N(C)CC(NC)c1cccnc1] |
TABLE 2A
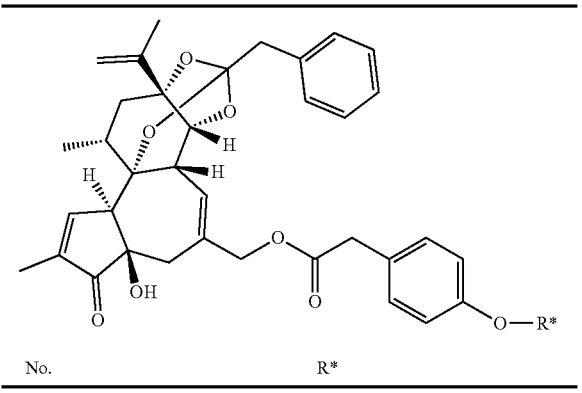
| No. | R* |
|---|---|
| II-1 | 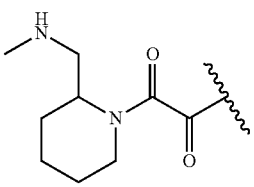 [SMILES: *C(=O)C(=O)N1CCCCC1CNC] |
TABLE 2A-continued
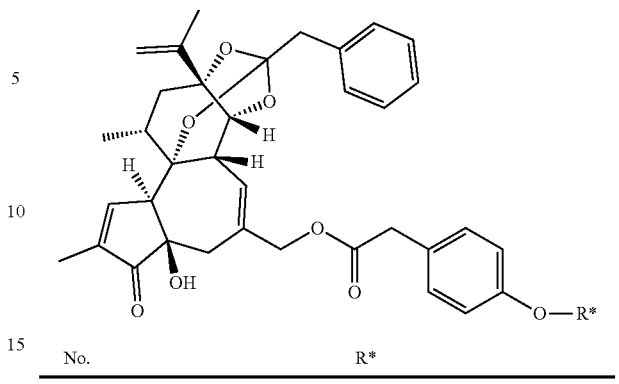
| No. | R* |
|---|---|
| II-2 | 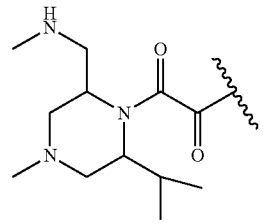 [SMILES: *C(=O)C(=O)N1C(CNC)CN(C)CC1C(C)C] |
| II-3 | 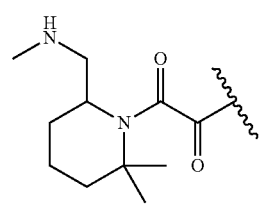 [SMILES: *C(=O)C(=O)N1C(CNC)CCCC1(C)C] |
| II-4 | 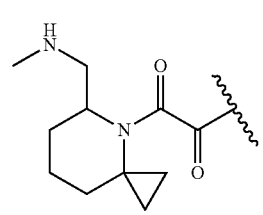 [SMILES: *C(=O)C(=O)N1C(CNC)CCCC12CC2] |
| II-5 | 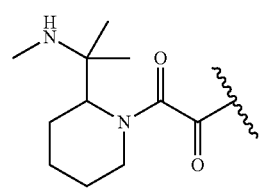 [SMILES: *C(=O)C(=O)N1CCCCC1C(C)(C)NC] |
| II-6 | 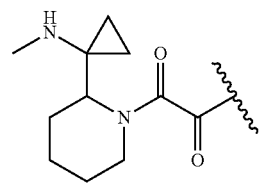 [SMILES: *C(=O)C(=O)N1CCCCC1C1(NC)CC1] |
| II-7 | 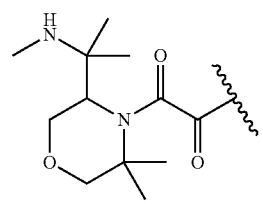 [SMILES: *C(=O)C(=O)N1C(C(C)(C)NC)COCC1(C)C] |

TABLE 2A-continued
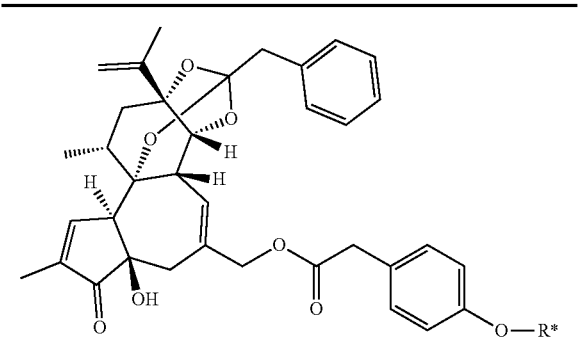
| No. | R* |
|---|---|
| II-8 | 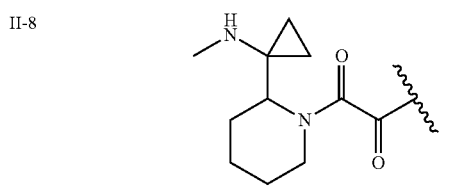 |
| II-9 | 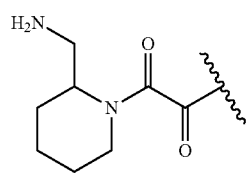 [SMILES: *C(=O)C(=O)N1CCCCC1CN] |
| II-10 | 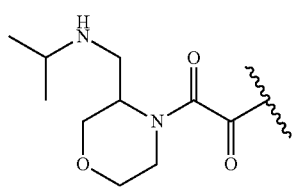 [SMILES: *C(=O)C(=O)N1CCOCC1CNC(C)C] |
| II-11 | 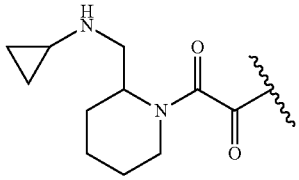 [SMILES: *C(=O)C(=O)N1CCCCC1CNC1CC1] |
| II-12 | 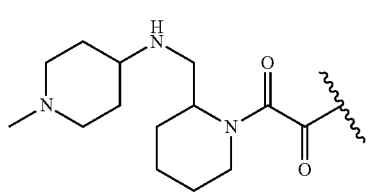 [SMILES: *C(=O)C(=O)N1CCCCC1CNC1CCN(C)CC1] |
| II-13 | 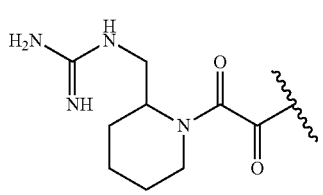 [SMILES: *C(=O)C(=O)N1CCCCC1CNC(=N)N] |
TABLE 2A-continued
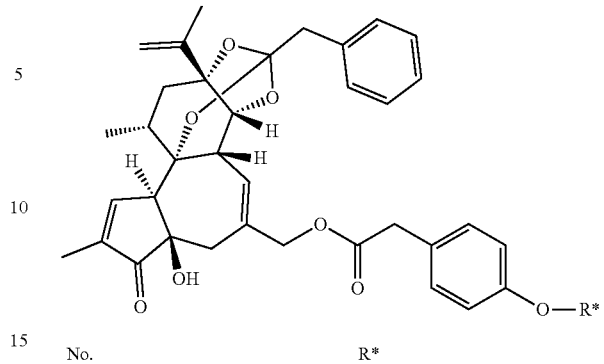
| No. | R* |
|---|---|
| II-14 | 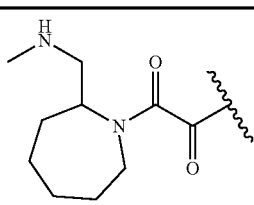 |
| II-15 | 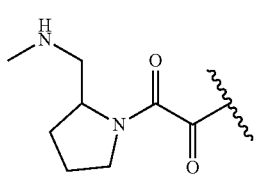 [SMILES: *C(=O)C(=O)N1CCCC1CNC] |
| II-16 | 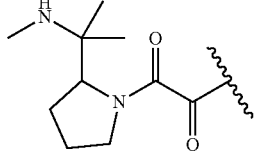 |
| II-17 | 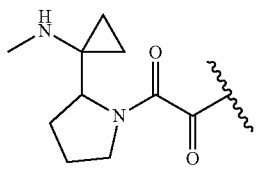 [SMILES: *C(=O)C(=O)N1CCCC1C1(NC)CC1] |
| II-18 | 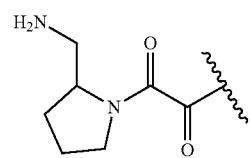 [SMILES: *C(=O)C(=O)N1CCCC1CN] |
| II-19 | 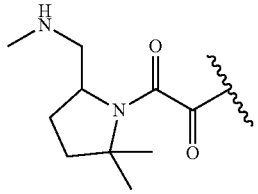 [SMILES: *C(=O)C(=O)N1C(CNC)CCC1(C)C] |
| II-20 | 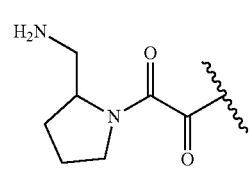 [SMILES: *C(=O)C(=O)N1CCCC1CN] |

TABLE 2A-continued
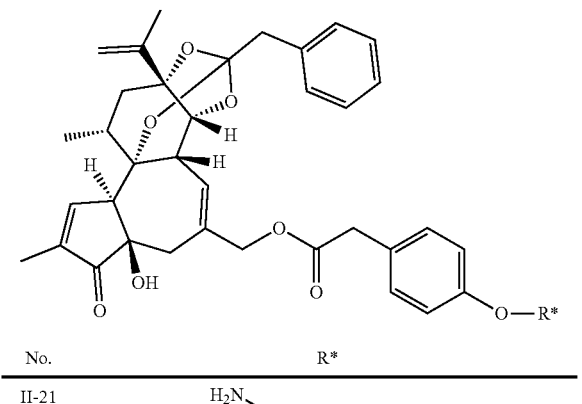
| No. | R* |
|---|---|
| II-21 | 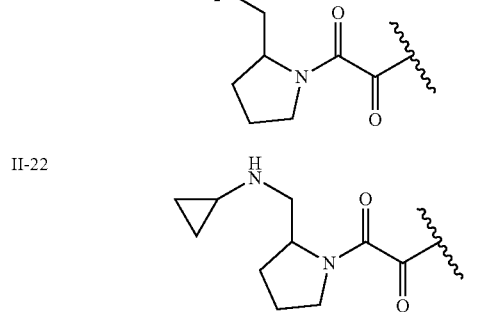 |
| II-22 | 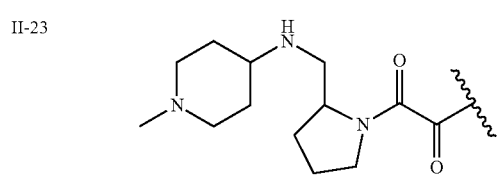 |
| II-23 | 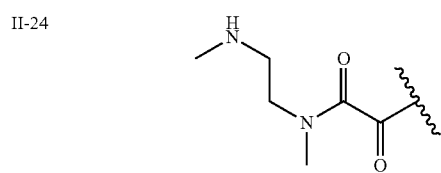 |
| II-24 | 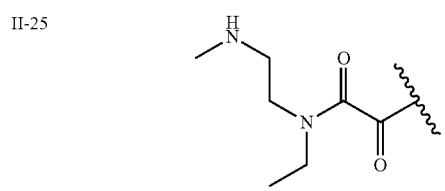 |
| II-25 | 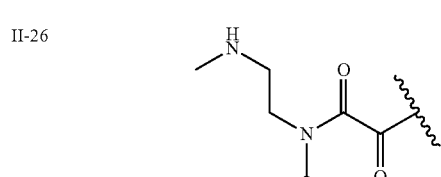 |
| II-26 | 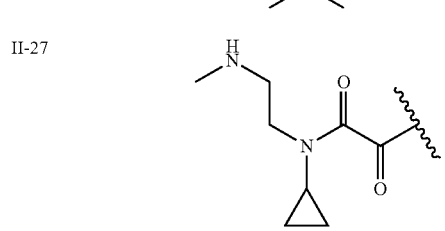 |
| II-27 | |
TABLE 2A-continued
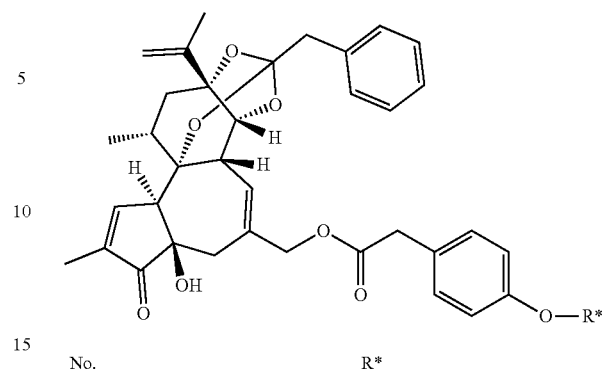
| No. | R* |
|---|---|
| II-28 | 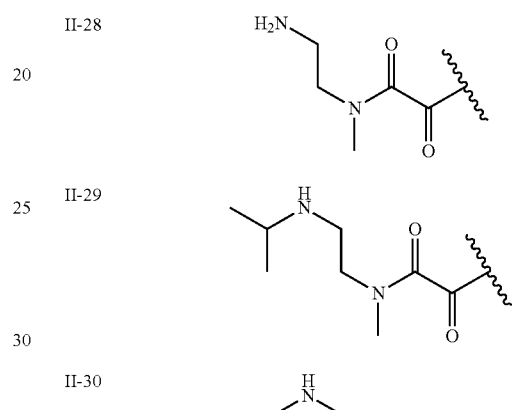 |
| II-29 | |
| II-30 | 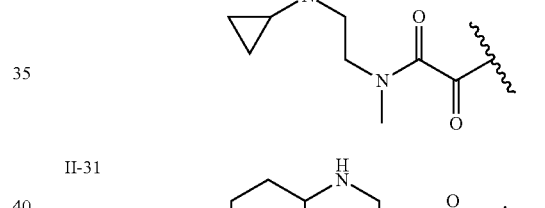 |
| II-31 | 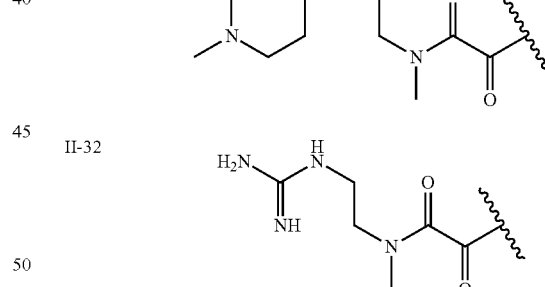 |
| II-32 | 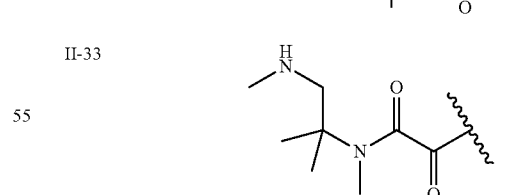 |
| II-33 | 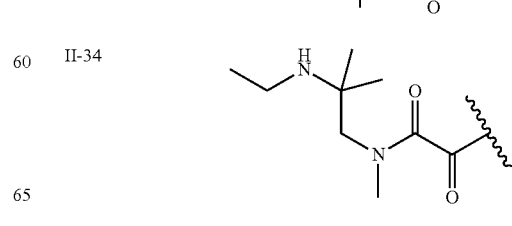 |
| II-34 | |

TABLE 2A-continued
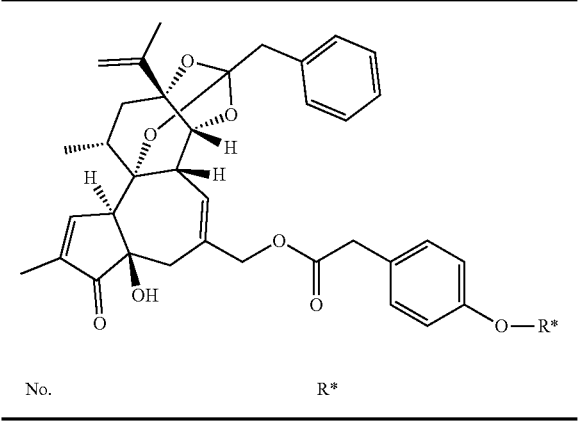
| No. | R* |
|---|---|
| II-35 | 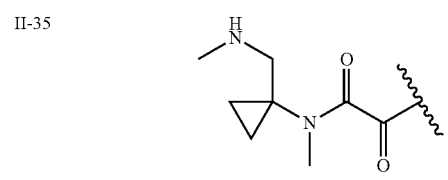 |
| II-36 | 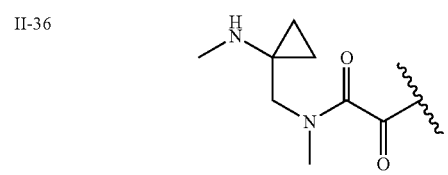 |
| II-37 | 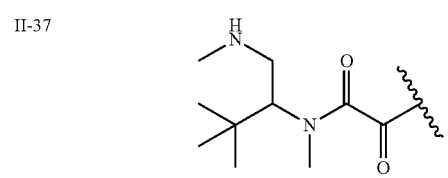 |
| II-38 | 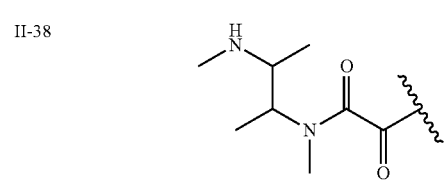 |
| II-39 | 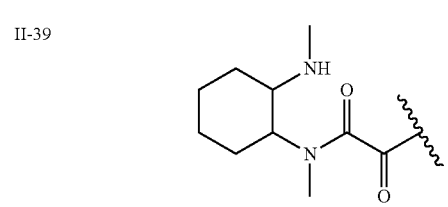 |
| II-40 | 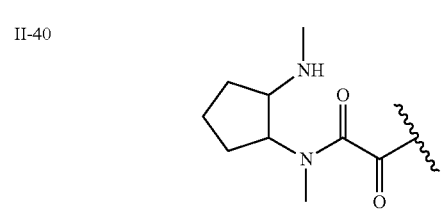 |
TABLE 2A-continued
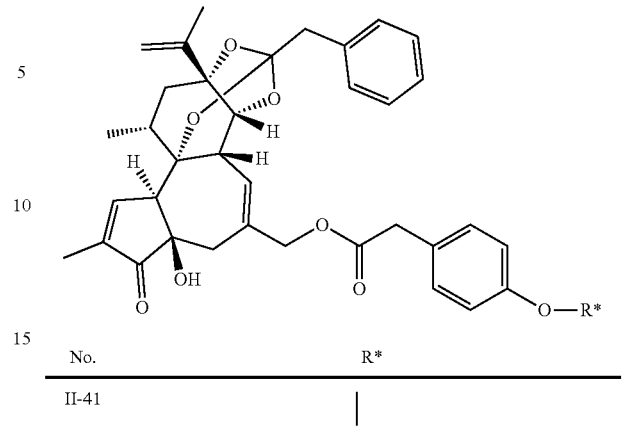
| No. | R* |
|---|---|
| II-41 | 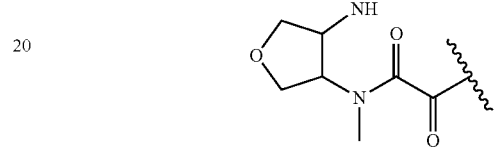 |
| II-42 | 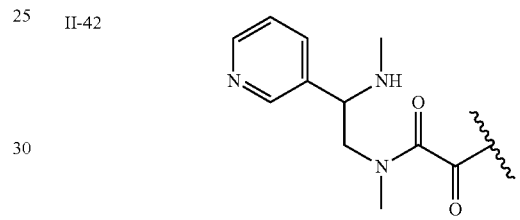 |
TABLE 3
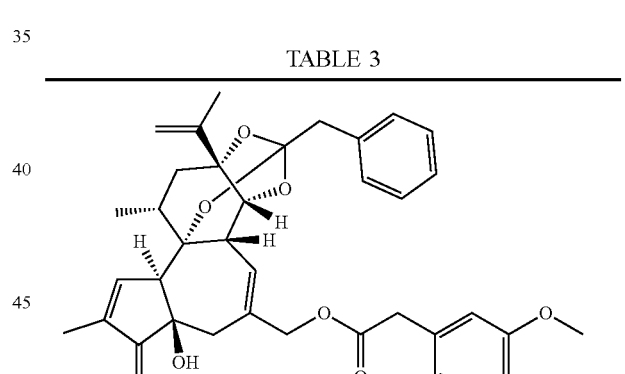
| No. | R* |
|---|---|
| III-1 | 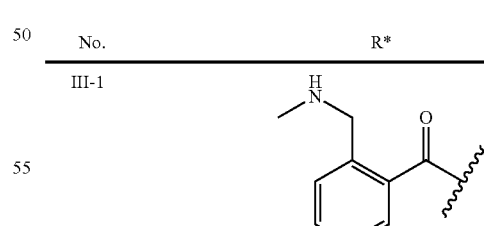 |
| III-2 | 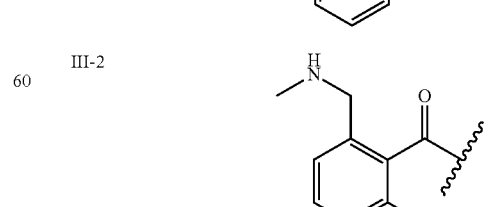 |

TABLE 3-continued
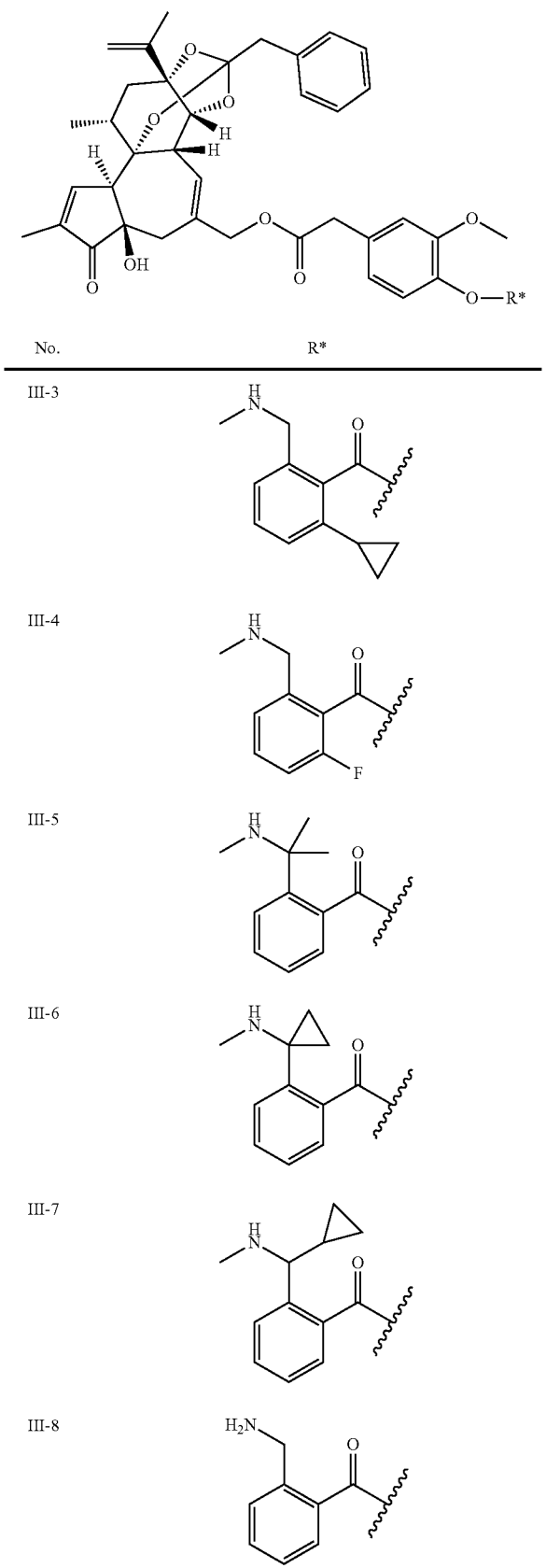
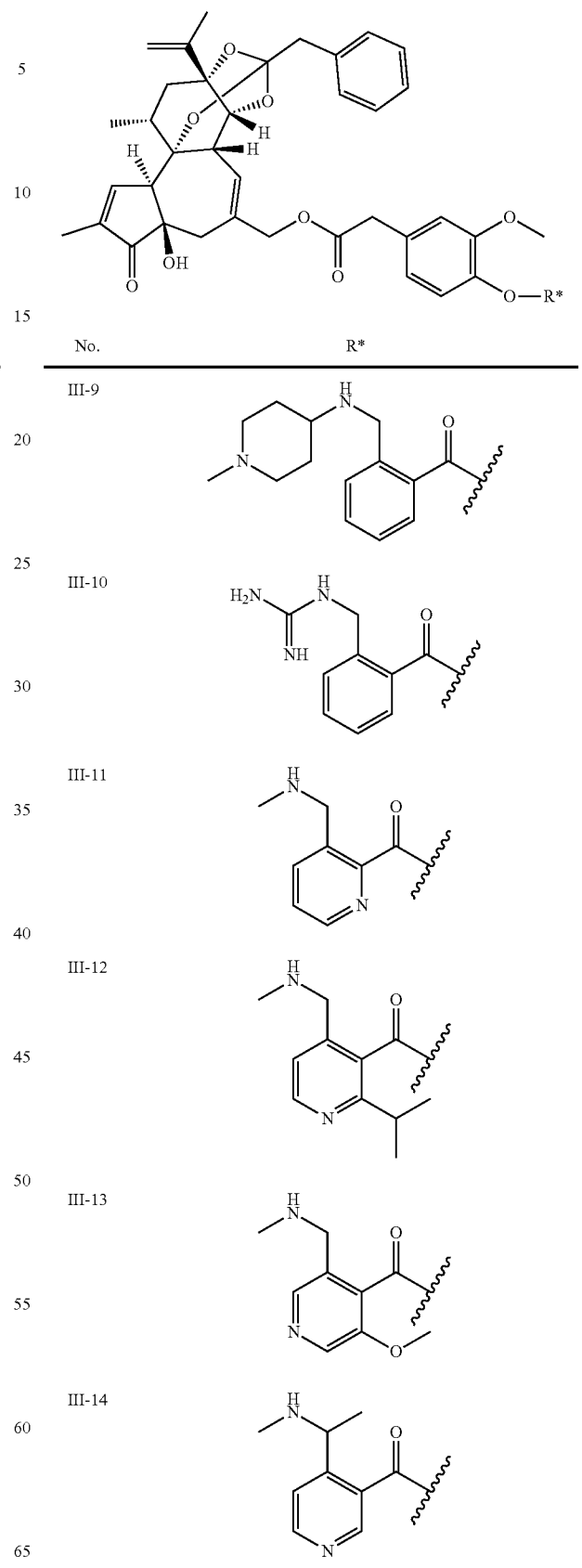

TABLE 3-continued
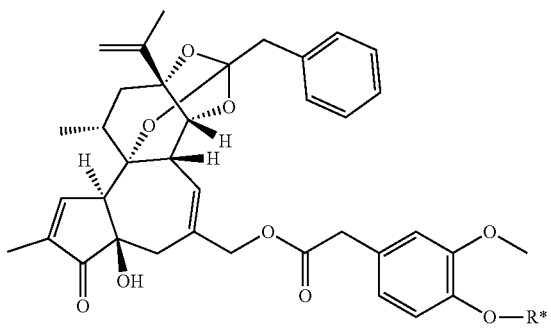
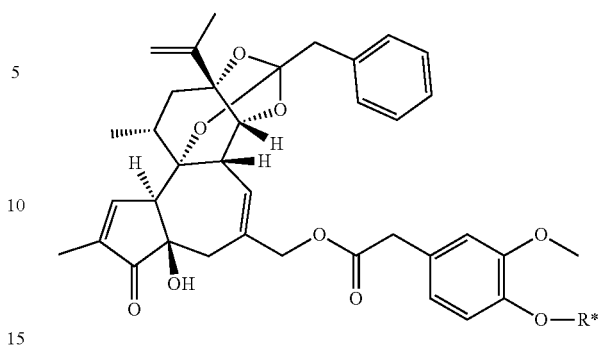

TABLE 3-continued
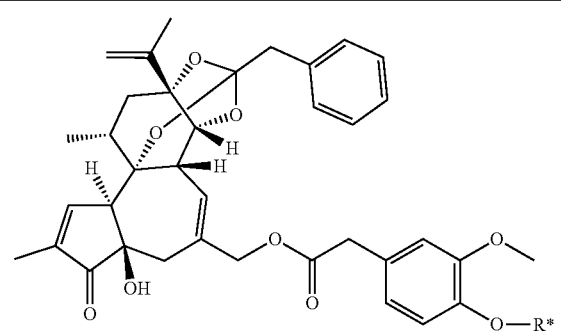
| No. | R* |
|---|---|
| III-27 | 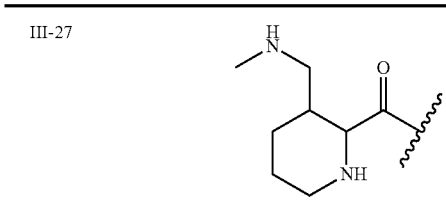 |
| III-28 | 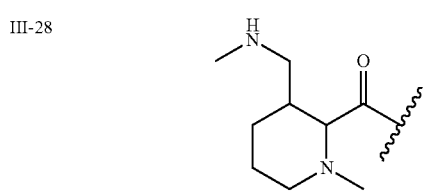 |
| III-29 | 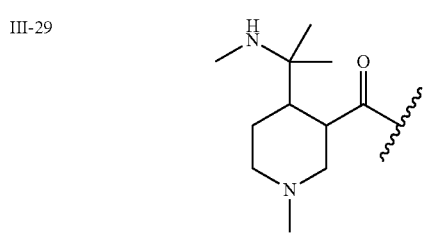 |
| III-30 | 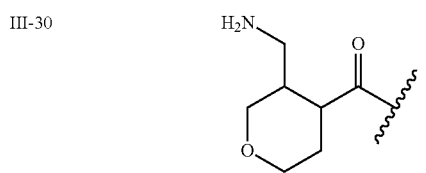 |
| III-31 | 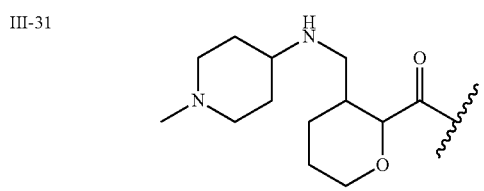 |
| III-32 | 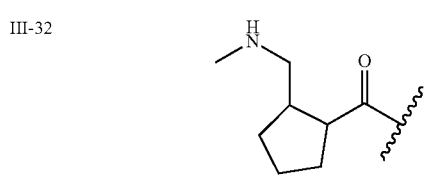 |
TABLE 3-continued
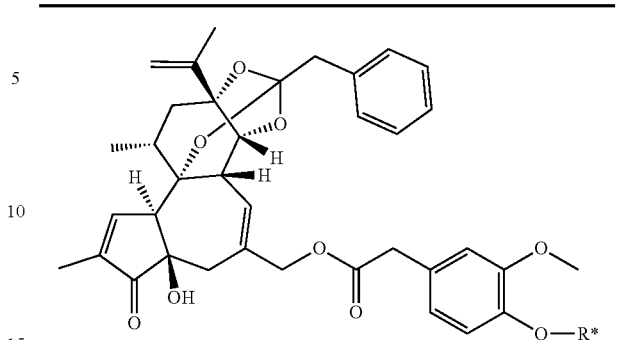
| No. | R* |
|---|---|
| III-33 | 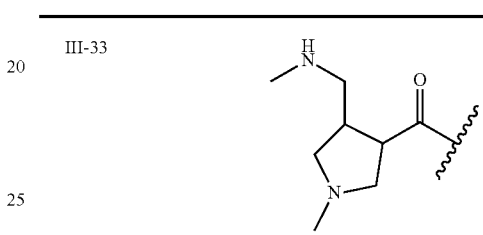 |
| III-34 | 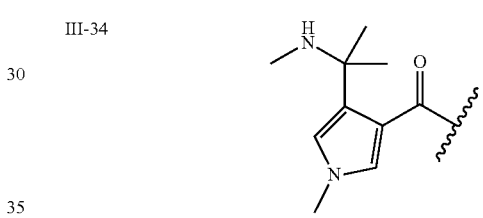 |
| III-35 | 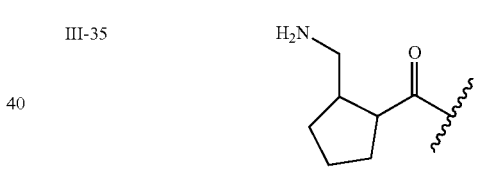 |
| III-36 | 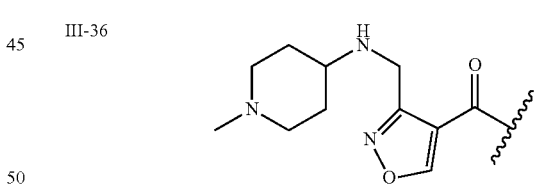 |
| III-37 | 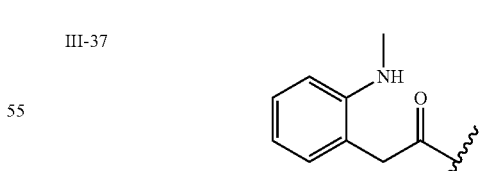 |
| III-38 | 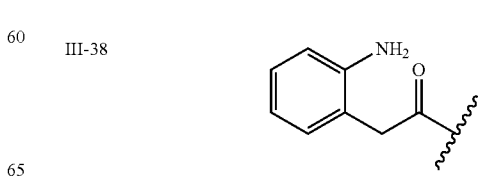 |

TABLE 3-continued
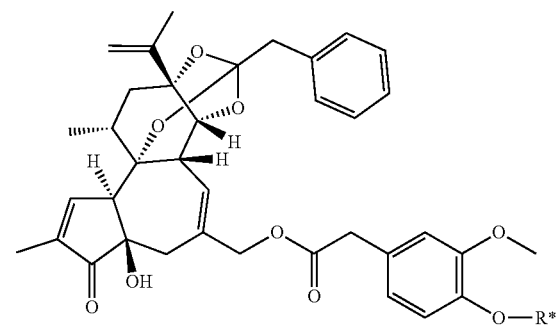
| No. | R* |
|---|---|
| III-39 | 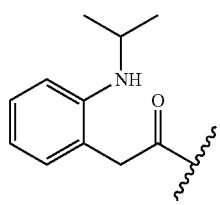 [SMILES: *C(=O)Cc1ccccc1NC(C)C] |
| III-40 | 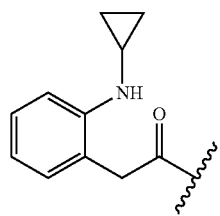 [SMILES: *C(=O)Cc1ccccc1NC1CC1] |
| III-41 | 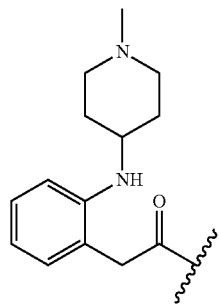 [SMILES: *C(=O)Cc1ccccc1NC1CCN(C)CC1] |
| III-42 | 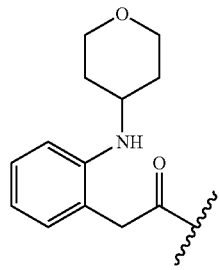 [SMILES: *C(=O)Cc1ccccc1NC1CCOCC1] |
| III-43 | 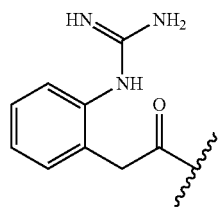 [SMILES: *C(=O)Cc1ccccc1NC(=N)N] |
TABLE 3-continued
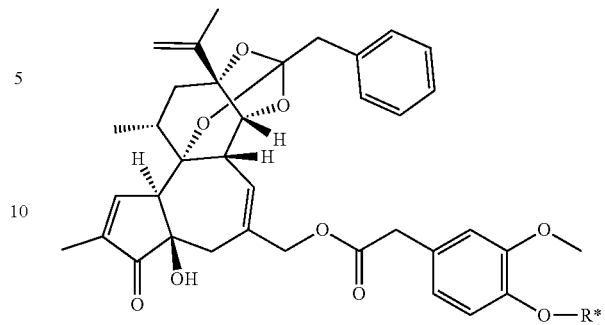
| No. | R* |
|---|---|
| III-44 | 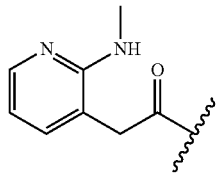 [SMILES: *C(=O)Cc1cccnc1NC] |
| III-45 | 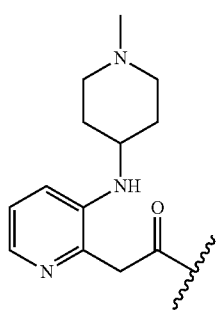 |
| III-46 | 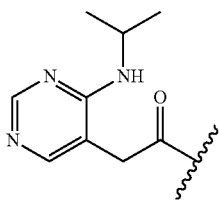 [SMILES: *C(=O)Cc1cncnc1NC(C)C] |
| III-47 | 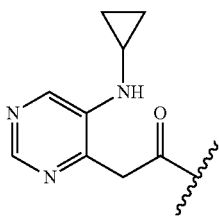 [SMILES: *C(=O)Cc1ncncc1NC1CC1] |
| III-48 | 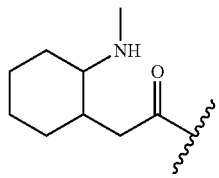 [SMILES: *C(=O)CC1CCCCC1NC] |
| III-49 | 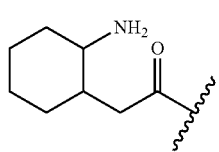 [SMILES: *C(=O)CC1CCCCC1N] |

TABLE 3-continued
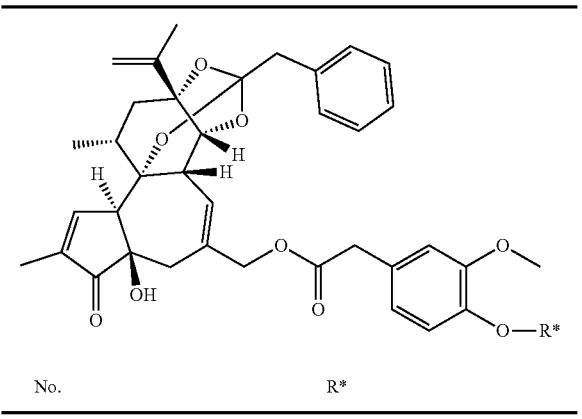
| No. | R* |
|---|---|
| III-50 | 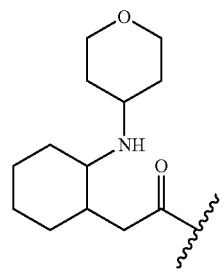 [SMILES: *C(=O)CC1CCCCC1NC1CCOCC1] |
| III-51 | 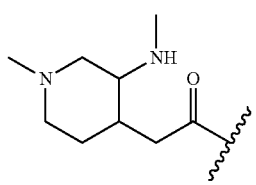 [SMILES: *C(=O)CC1CCN(C)CC1NC] |
| III-52 | 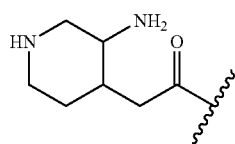 [SMILES: *C(=O)CC1CCNCC1N] |
| III-53 | 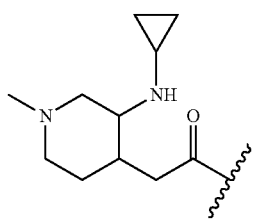 [SMILES: *C(=O)CC1CCN(C)CC1NC1CC1] |
| III-54 | 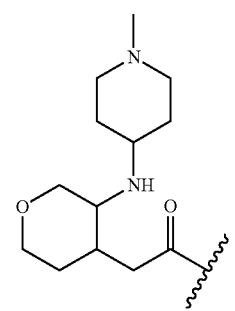 [SMILES: *C(=O)CC1CCOCC1NC1CCN(C)CC1] |
TABLE 3-continued
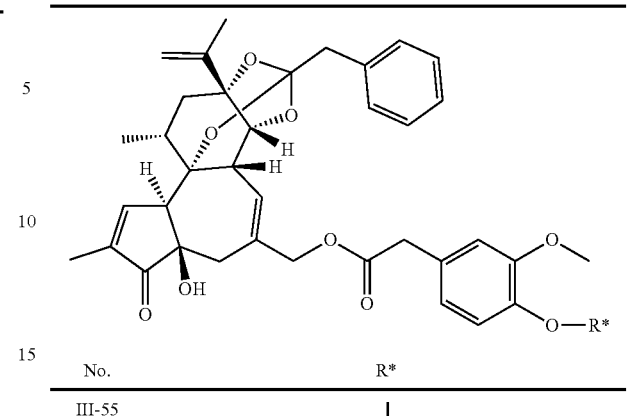
| No. | R* |
|---|---|
| III-55 | 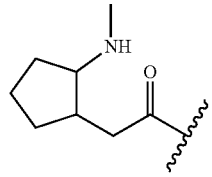 [SMILES: *C(=O)CC1CCCC1NC] |
| III-56 | 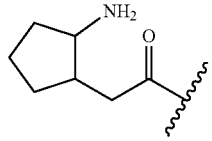 [SMILES: *C(=O)CC1CCCC1N] |
| III-57 | 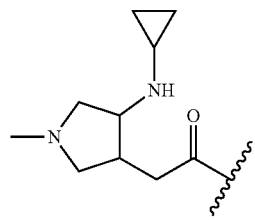 [SMILES: *C(=O)CC1CN(C)CC1NC1CC1] |
| III-58 | 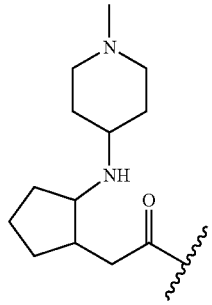 [SMILES: *C(=O)CC1CCCC1NC1CCN(C)CC1] |
| III-59 | 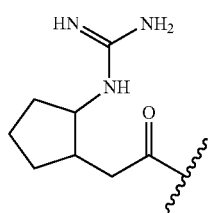 [SMILES: *C(=O)CC1CCCC1NC(=N)N] |
| III-60 | 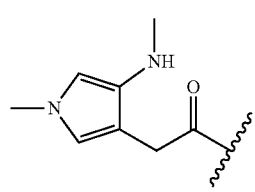 [SMILES: *C(=O)Cc1cn(C)cc1NC] |

TABLE 3-continued
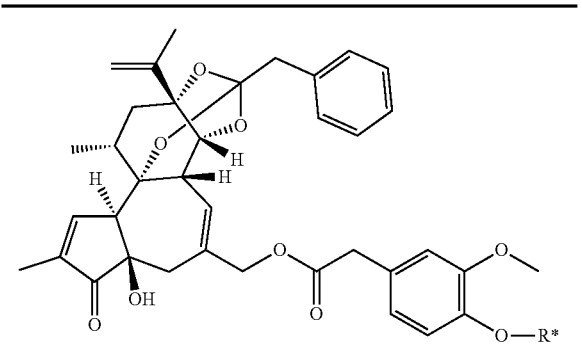
| No. | R* |
|---|---|
| III-61 | 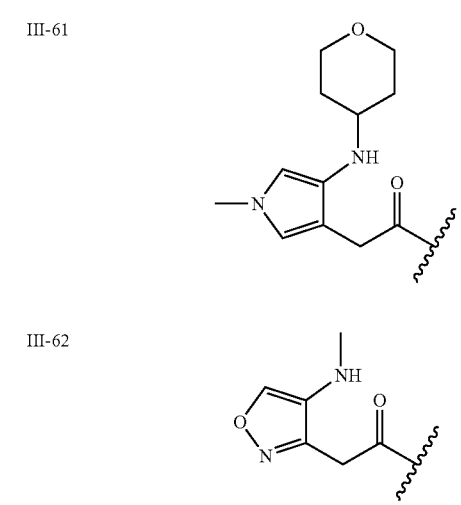 |
| III-62 | (structure shown in image 2) |
TABLE 3A
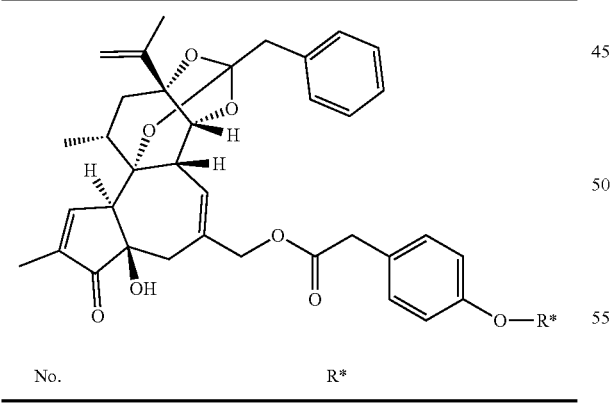
| No. | R* |
|---|---|
| III-1 | 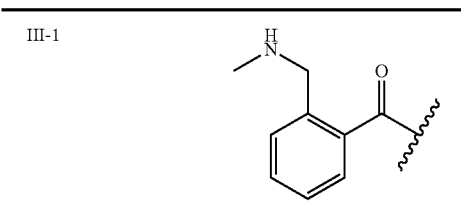 |
TABLE 3A-continued
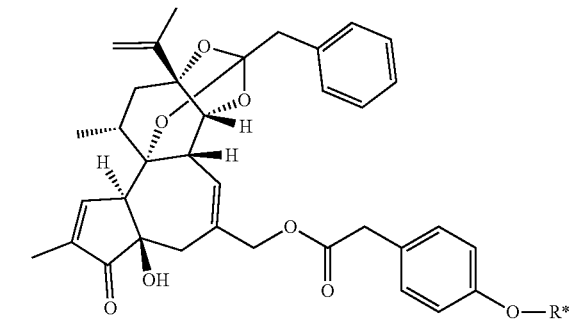
| No. | R* |
|---|---|
| III-2 | 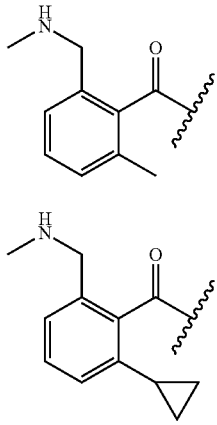 |
| III-3 | (structure in image 4) |
| III-4 | (structure in image 4) |
| III-5 | 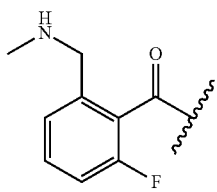 [SMILES: *C(=O)c1c(F)cccc1CNC] |
| III-6 | 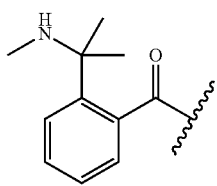 [SMILES: *C(=O)c1ccccc1C(C)(C)NC] |
| III-7 | 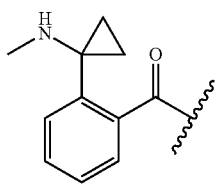 [SMILES: *C(=O)c1ccccc1C1(NC)CC1] |

TABLE 3A-continued
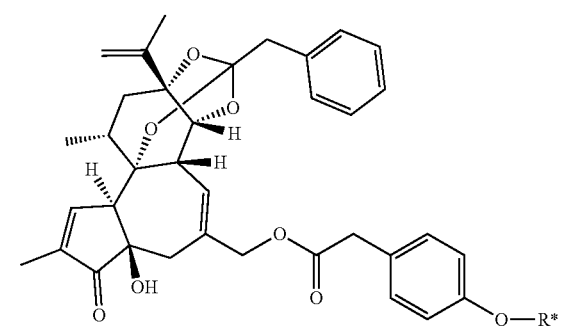
| No. | R* |
|---|---|
| III-8 | 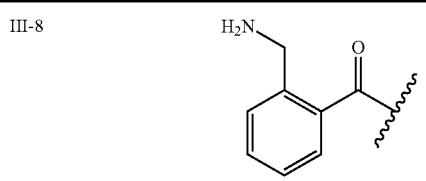 |
| III-9 | 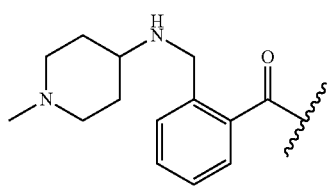 [SMILES: *C(=O)c1ccccc1CNC1CCN(C)CC1] |
| III-10 | 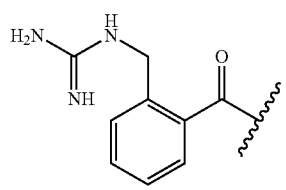 [SMILES: *C(=O)c1ccccc1CNC(=N)N] |
| III-11 | 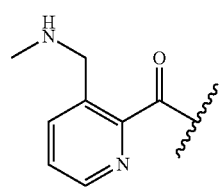 [SMILES: *C(=O)c1ncccc1CNC] |
| III-12 | 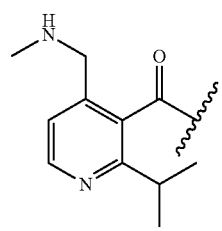 [SMILES: *C(=O)c1c(CNC)ccnc1C(C)C] |
| III-13 | 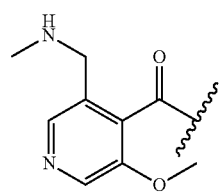 |
TABLE 3A-continued
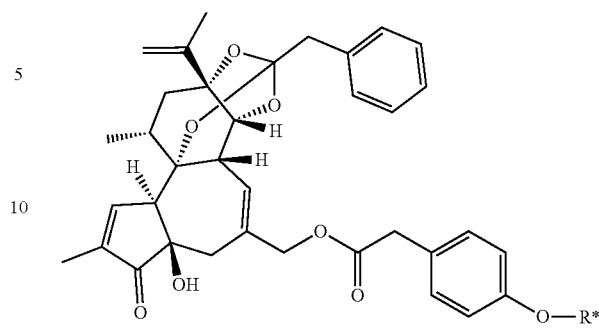
| No. | R* |
|---|---|
| III-14 | 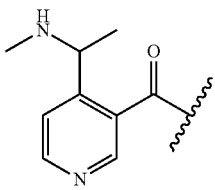 [SMILES: *C(=O)c1cnccc1C(C)NC] |
| III-15 | 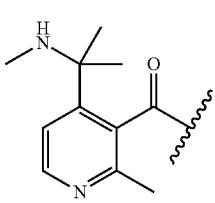 [SMILES: *C(=O)c1c(C(C)(C)NC)ccnc1C] |
| III-16 | 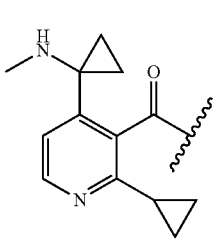 [SMILES: *C(=O)c1c(C2(NC)CC2)ccnc1C1CC1] |
| III-17 | 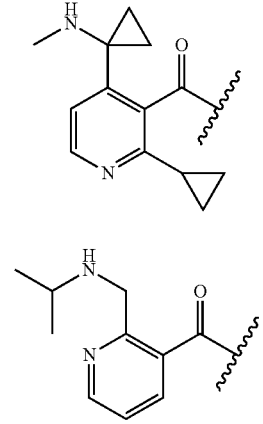 |
| III-18 | 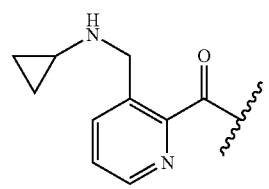 [SMILES: *C(=O)c1ncccc1CNC1CC1] |
| III-19 | 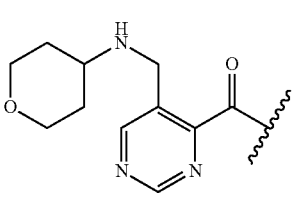 [SMILES: *C(=O)c1ncncc1CNC1CCOCC1] |

TABLE 3A-continued
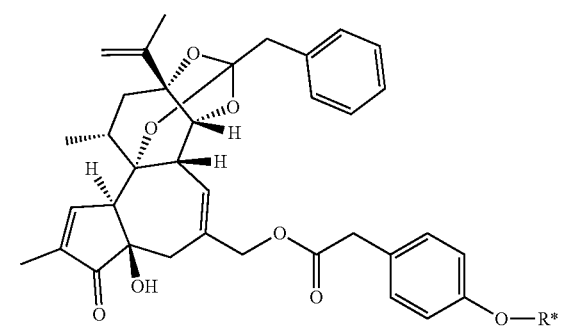
| No. | R* |
|---|---|
| III-20 | 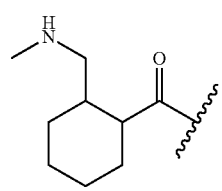 [SMILES: *C(=O)C1CCCCC1CNC] |
| III-21 | 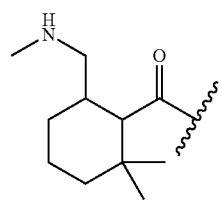 [SMILES: *C(=O)C1C(CNC)CCCC1(C)C] |
| III-22 | 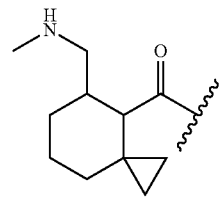 [SMILES: *C(=O)C1C(CNC)CCCC12CC2] |
| III-23 | 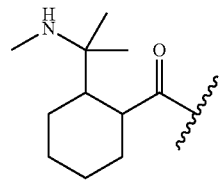 [SMILES: *C(=O)C1CCCCC1C(C)(C)NC] |
| III-24 | 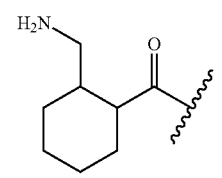 |
| III-25 | 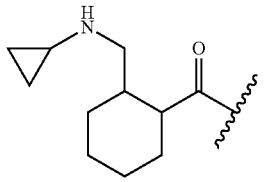 [SMILES: *C(=O)C1CCCCC1CNC1CC1] |
TABLE 3A-continued
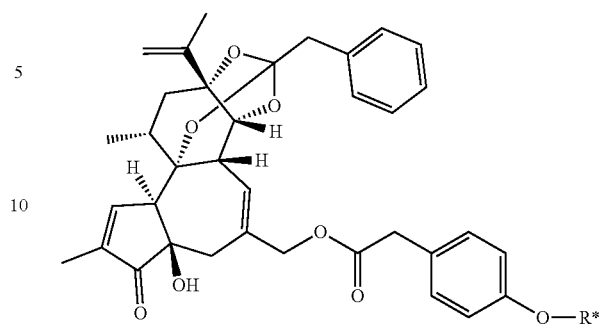
| No. | R* |
|---|---|
| III-26 | 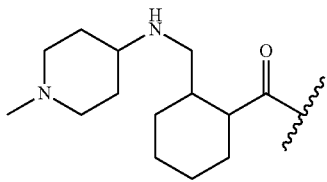 |
| III-27 | 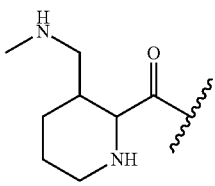 [SMILES: *C(=O)C1NCCCC1CNC] |
| III-28 | 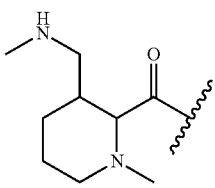 [SMILES: *C(=O)C1C(CNC)CCCN1C] |
| III-29 | 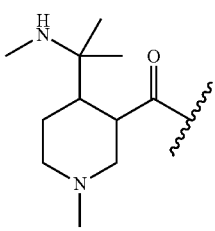 [SMILES: *C(=O)C1CN(C)CCC1C(C)(C)NC] |
| III-30 | 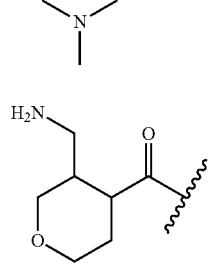 |
| III-31 | 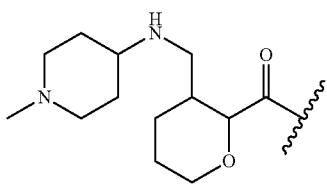 [SMILES: *C(=O)C1OCCCC1CNC1CCN(C)CC1] |

TABLE 3A-continued
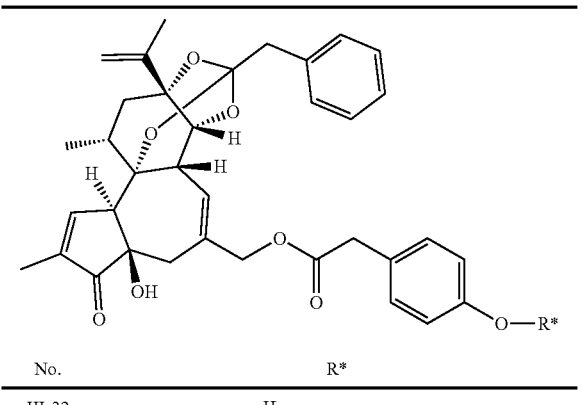
| No. | R* |
|---|---|
| III-32 | 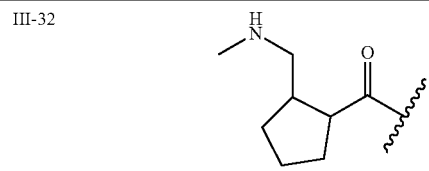 |
| III-33 | 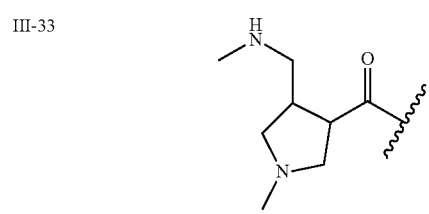 |
| III-34 | 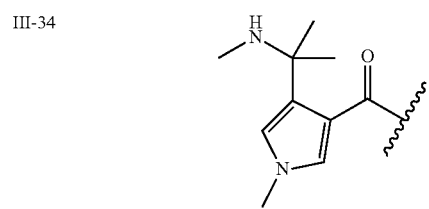 |
| III-35 | 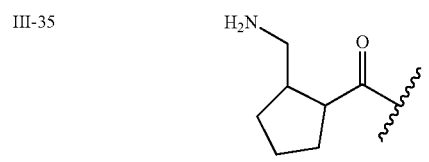 |
| III-36 | 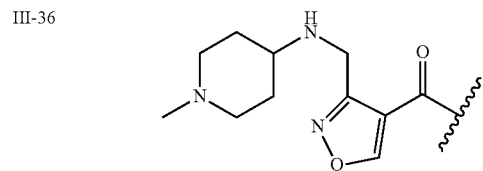 |
| III-37 | 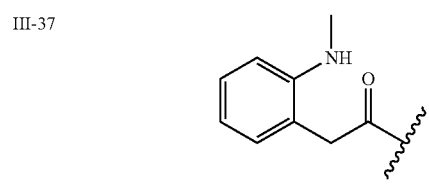 |
| III-38 | 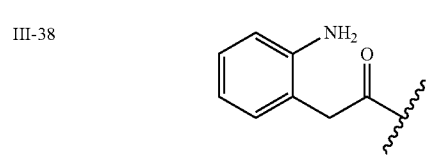 |
TABLE 3A-continued
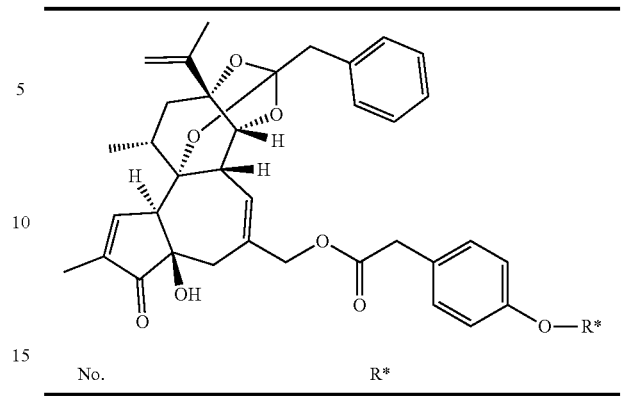
| No. | R* |
|---|---|
| III-39 | 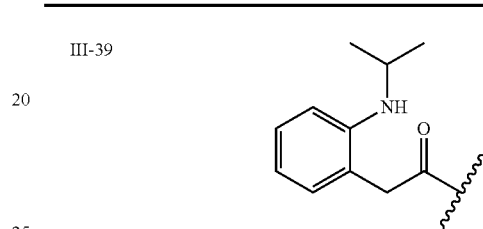 |
| III-40 | 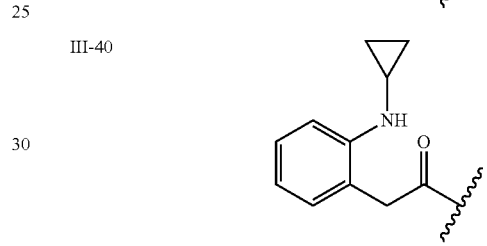 |
| III-41 | 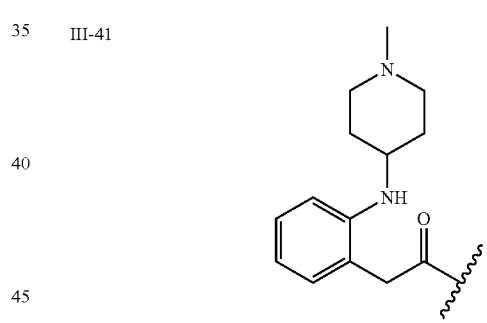 |
| III-42 | 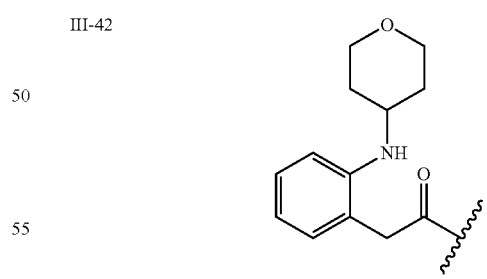 |
| III-43 | 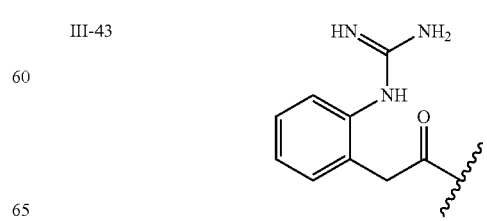 |

TABLE 3A-continued
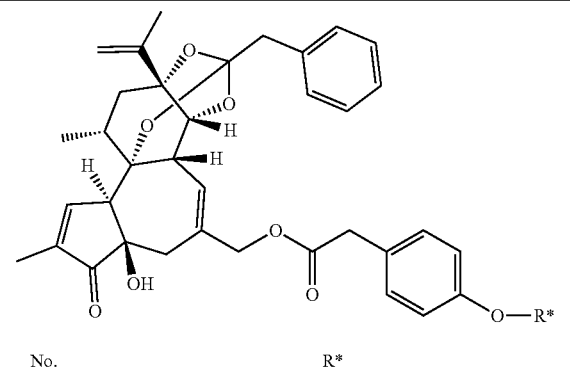
| No. | R* |
|---|---|
| III-44 | 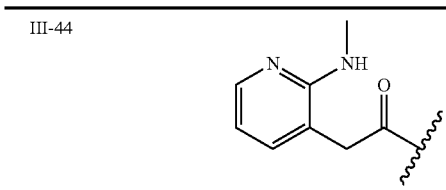 |
| III-45 | 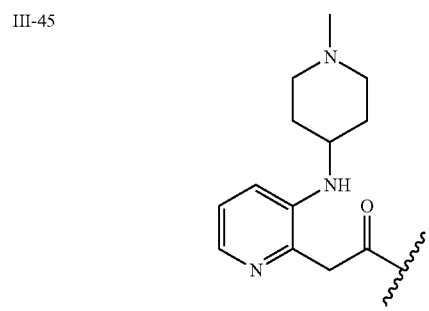 |
| III-46 | 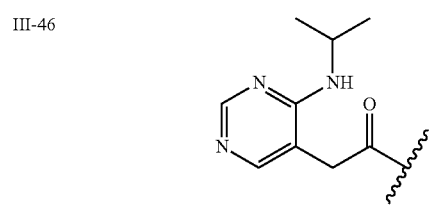 |
| III-47 | 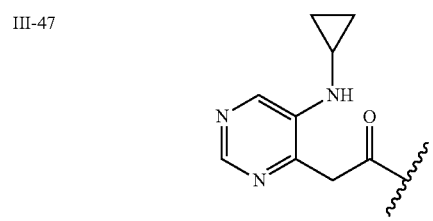 |
| III-48 | 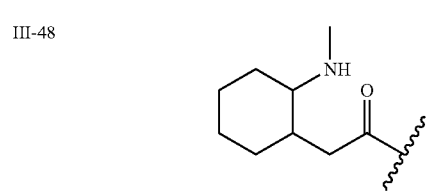 |
| III-49 | 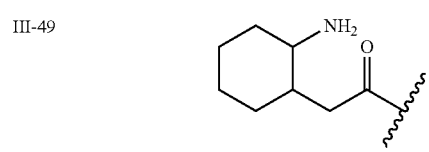 |
TABLE 3A-continued
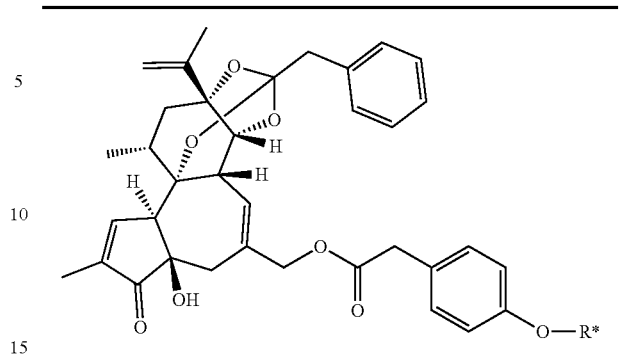
| No. | R* |
|---|---|
| III-50 | 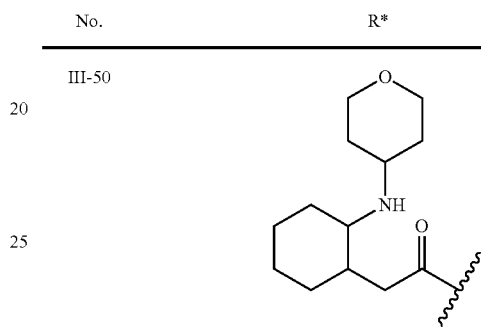 |
| III-51 | 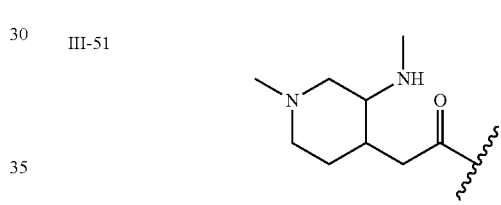 |
| III-52 | 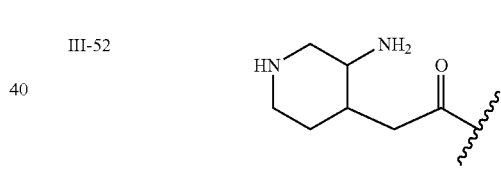 |
| III-53 | 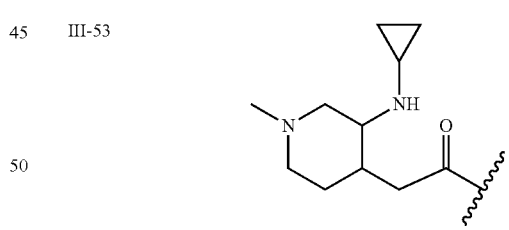 |
| III-54 |  |
| | 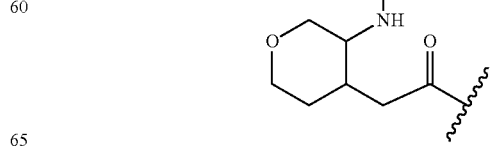 |

TABLE 3A-continued

| No. | R* |
|---|---|
| III-55 | (2-aminocyclopentyl-methyl ketone fragment with NHMe) |
| III-56 | (2-aminocyclopentyl-methyl ketone fragment with NH₂) |
| III-57 | (1-methyl-4-(cyclopropylamino)pyrrolidin-3-yl fragment) |
| III-58 | (1-methylpiperidin-4-yl-amino-cyclopentyl ketone fragment) |
| III-59 | (2-guanidinocyclopentyl ketone fragment) |
| III-60 | (1-methyl-4-(methylamino)pyrrol-3-yl ketone fragment) |
| III-61 | (4-((tetrahydro-2H-pyran-4-yl)amino)-1-methylpyrrol-3-yl ketone fragment) |
| III-62 | (4-(methylamino)isoxazol-3-yl ketone fragment) |

TABLE 4

| No. | R* |
|---|---|
| IV-1 | (2-(methylamino)phenyl ester fragment) |
| IV-2 | (2-aminophenyl ester fragment) |

TABLE 4-continued
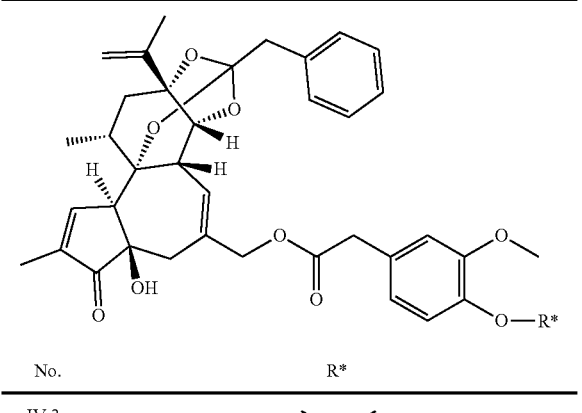
| No. | R* |
|---|---|
| IV-3 | 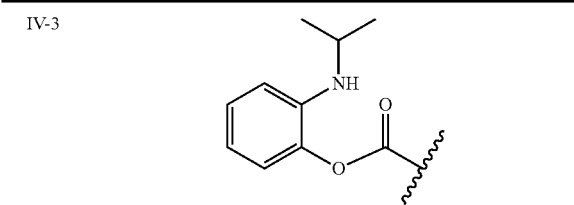 |
| IV-4 | 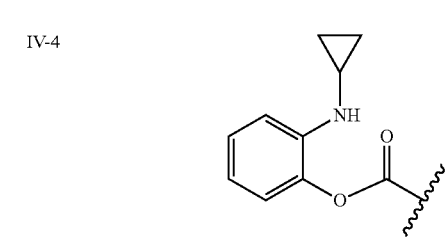 |
| IV-5 | 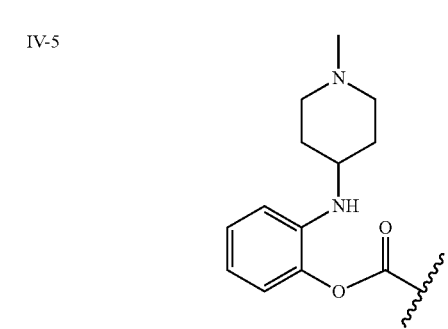 |
| IV-6 | 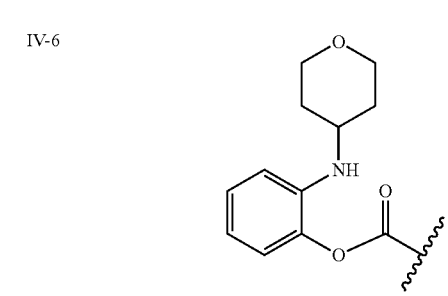 |
| IV-7 | 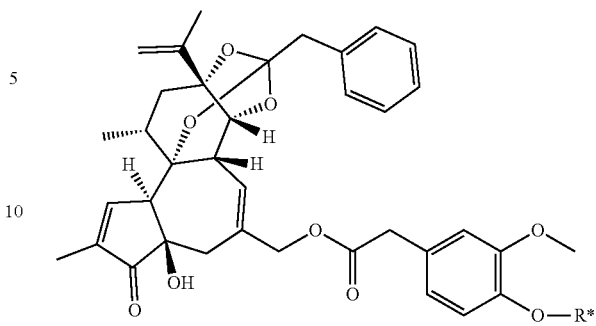 |
TABLE 4-continued
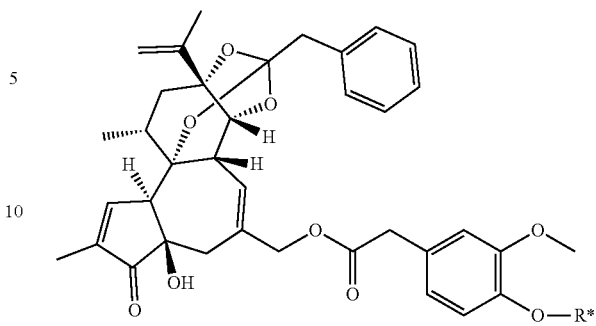
| No. | R* |
|---|---|
| IV-8 | 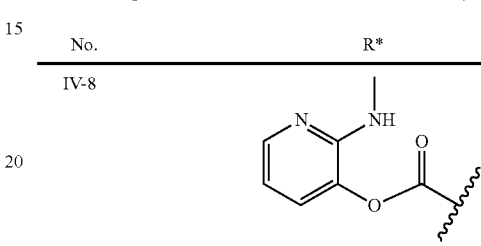 |
| IV-9 | 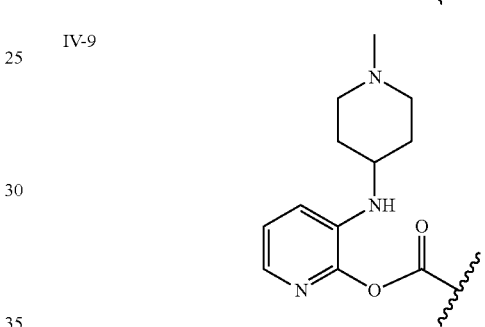 |
| IV-10 | 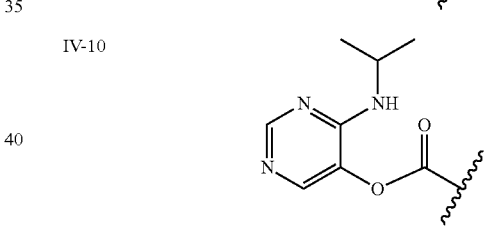 |
| IV-11 | 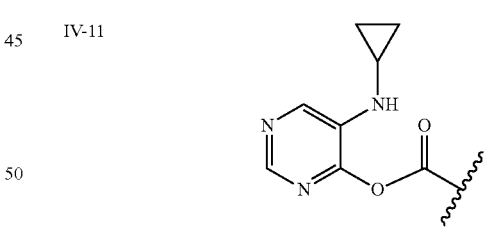 |
| IV-12 | 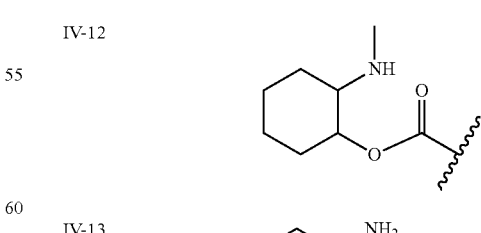 |
| IV-13 | |

TABLE 4-continued
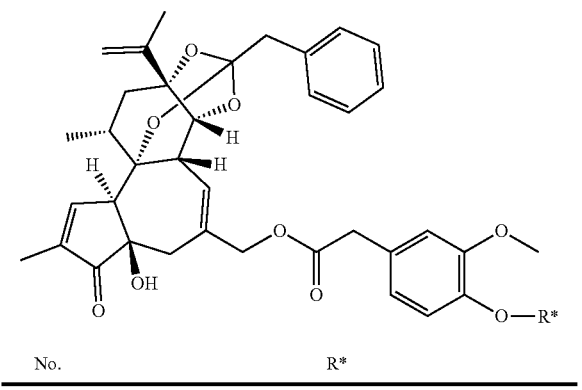
| No. | R* |
|---|---|
| IV-14 | 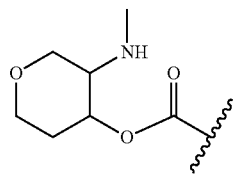 [SMILES: *C(=O)OC1CCOCC1NC] |
| IV-15 | 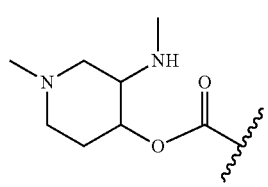 [SMILES: *C(=O)OC1CCN(C)CC1NC] |
| IV-16 | 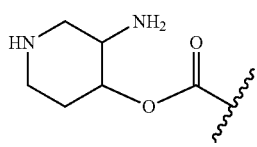 [SMILES: *C(=O)OC1CCNCC1N] |
| IV-17 | 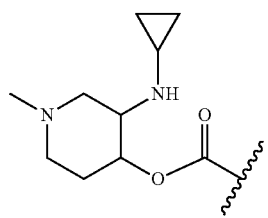 [SMILES: *C(=O)OC1CCN(C)CC1NC1CC1] |
| IV-18 | 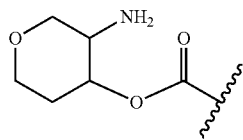 [SMILES: *C(=O)OC1CCOCC1N] |
| IV-19 | 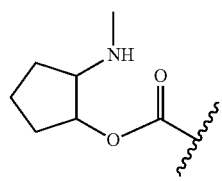 [SMILES: *C(=O)OC1CCCC1NC] |
| IV-20 | 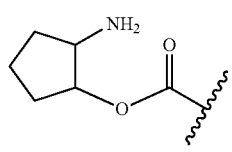 [SMILES: *C(=O)OC1CCCC1N] |
TABLE 4-continued
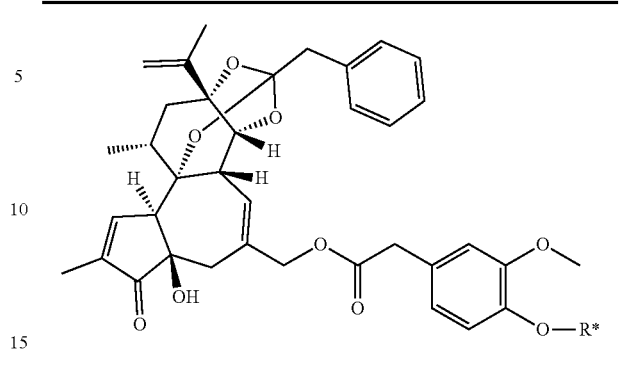
| No. | R* |
|---|---|
| IV-21 | 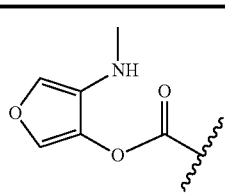 |
| IV-22 | 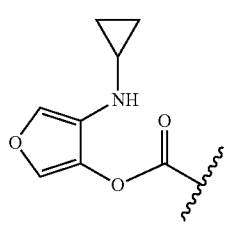 [SMILES: *C(=O)Oc1cocc1NC1CC1] |
| IV-23 | 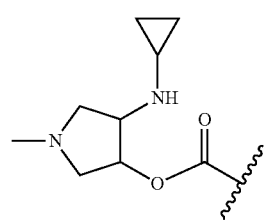 |
| IV-24 | 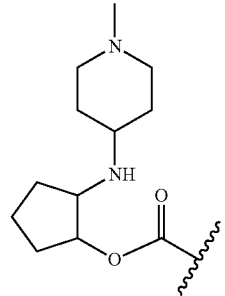 [SMILES: *C(=O)OC1CCCC1NC1CCN(C)CC1] |
| IV-25 | 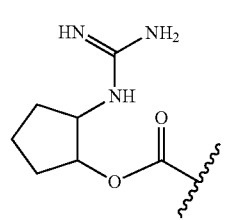 [SMILES: *C(=O)OC1CCCC1NC(=N)N] |

TABLE 4-continued
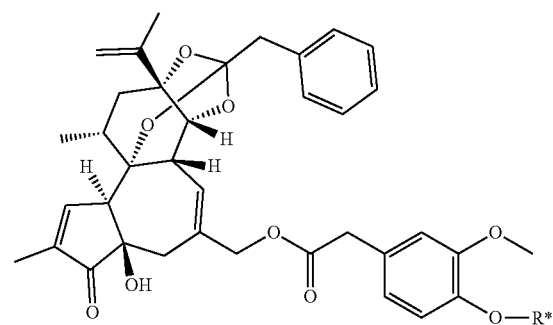
| No. | R* |
|---|---|
| IV-26 |  |
| IV-27 | 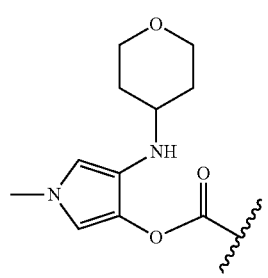 [SMILES: *C(=O)Oc1cn(C)cc1NC1CCOCC1] |
| IV-28 | |
| IV-29 | 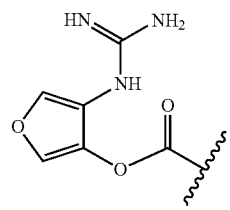 [SMILES: *C(=O)Oc1cocc1NC(=N)N] |
| IV-30 | |
TABLE 4A
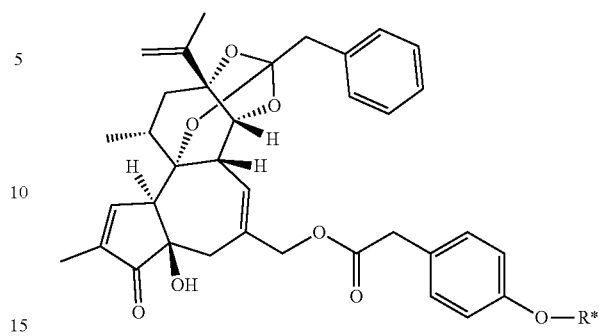
| No. | R* |
|---|---|
| IV-1 | |
| IV-2 | 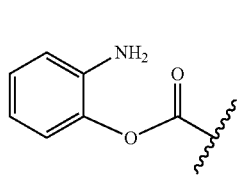 [SMILES: *C(=O)Oc1ccccc1N] |
| IV-3 | 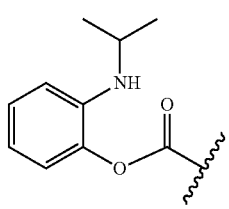 [SMILES: *C(=O)Oc1ccccc1NC(C)C] |
| IV-4 | |
| IV-5 | 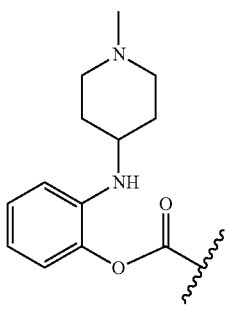 [SMILES: *C(=O)Oc1ccccc1NC1CCN(C)CC1] |

TABLE 4A-continued
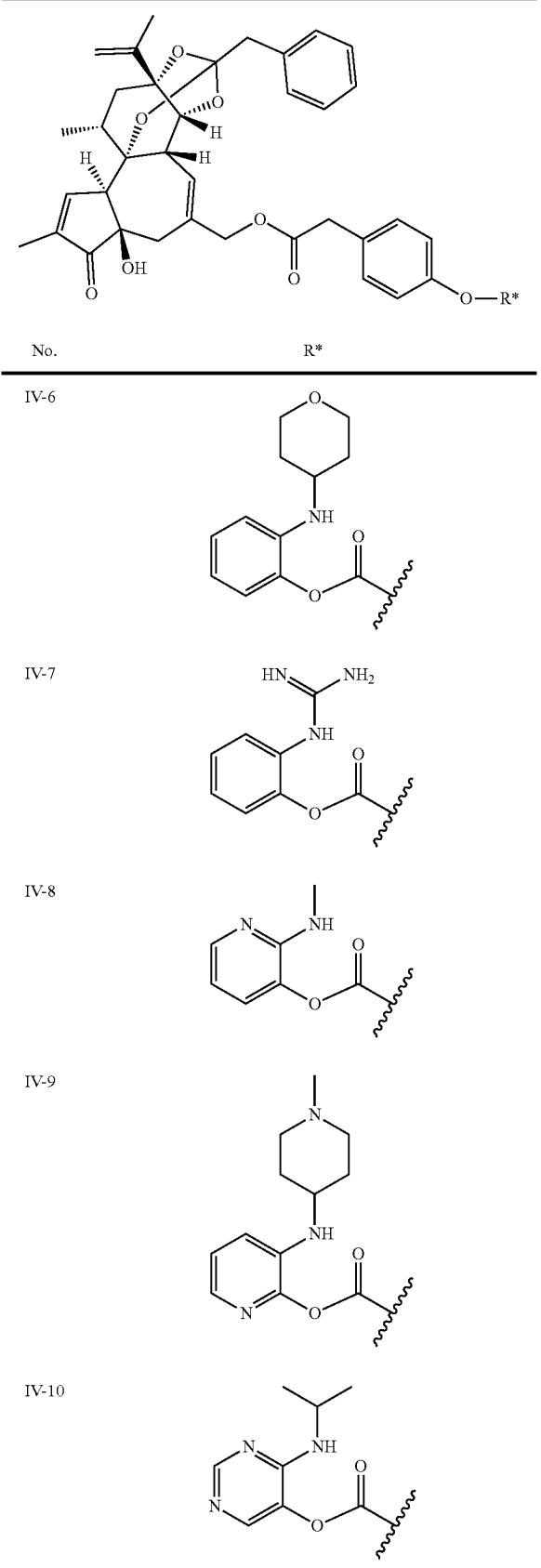
| No. | R* |
|---|---|
| IV-6 | |
| IV-7 | |
| IV-8 | |
| IV-9 | |
| IV-10 | |
TABLE 4A-continued
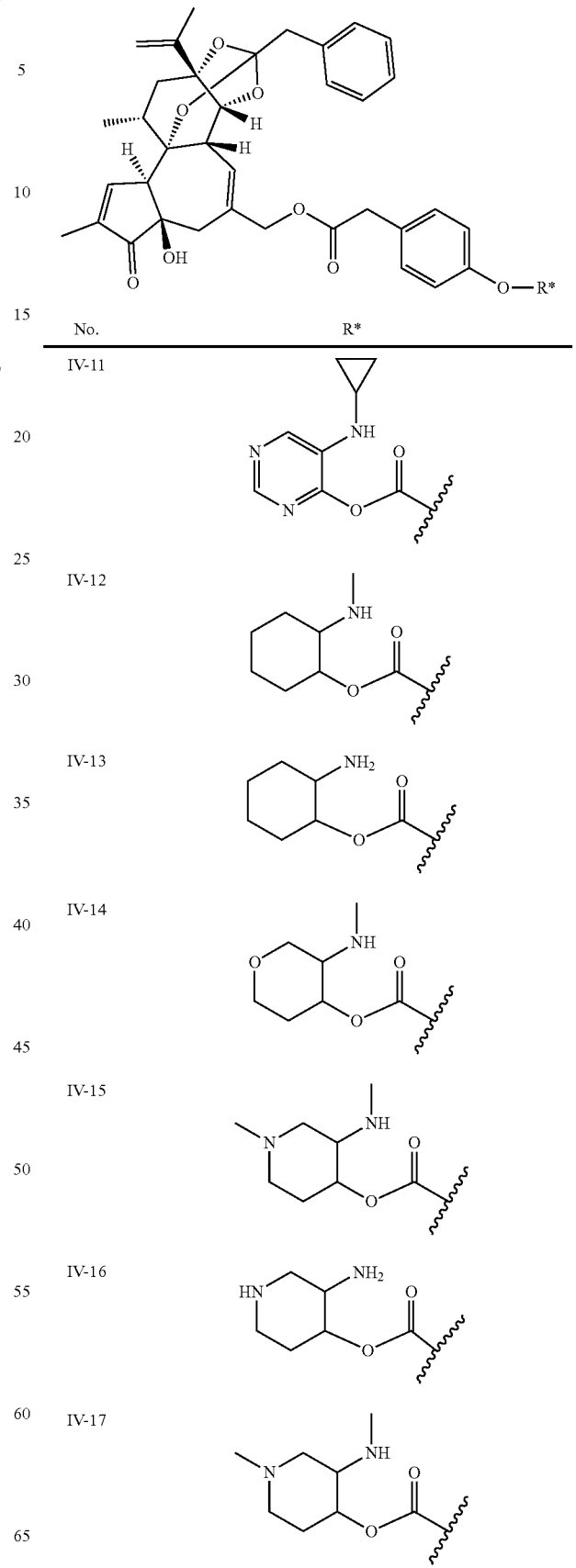
| No. | R* |
|---|---|
| IV-11 | |
| IV-12 | |
| IV-13 | |
| IV-14 | |
| IV-15 | |
| IV-16 | |
| IV-17 | |

101
TABLE 4A-continued
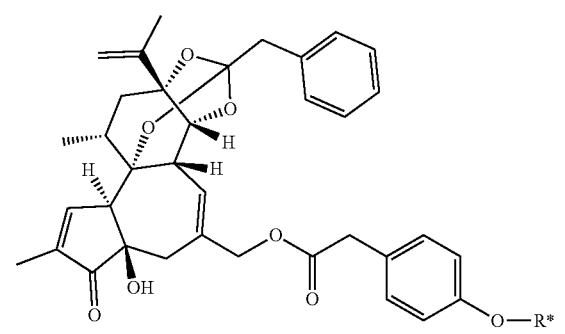
| No. | R* |
|---|---|
| IV-18 | 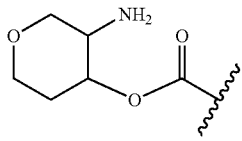 [SMILES: *C(=O)OC1CCOCC1N] |
| IV-19 | 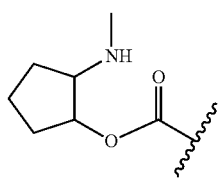 [SMILES: *C(=O)OC1CCCC1NC] |
| IV-20 | 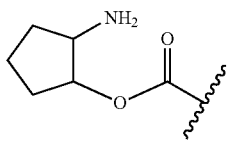 [SMILES: *C(=O)OC1CCCC1N] |
| IV-21 | 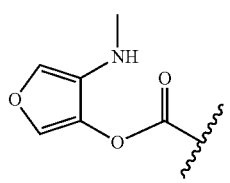 [SMILES: *C(=O)Oc1cocc1NC] |
| IV-22 | 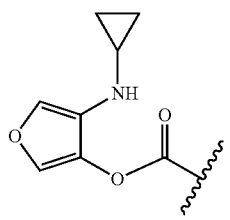 [SMILES: *C(=O)Oc1cocc1NC1CC1] |
| IV-23 | 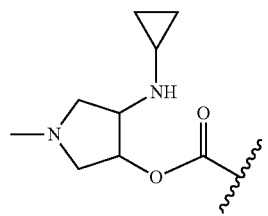 [SMILES: *C(=O)OC1CN(C)CC1NC1CC1] |
102
TABLE 4A-continued
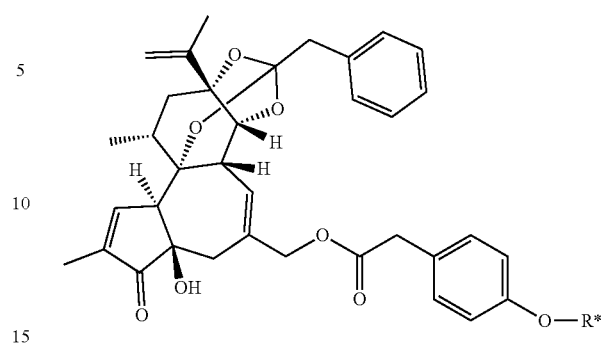
| No. | R* |
|---|---|
| IV-24 | 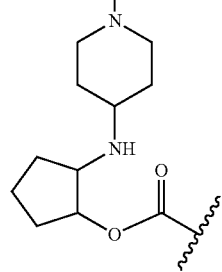 |
| IV-25 | 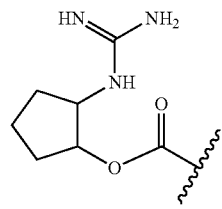 [SMILES: *C(=O)OC1CCCC1NC(=N)N] |
| IV-26 | 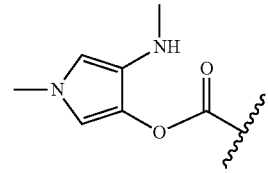 [SMILES: *C(=O)Oc1cn(C)cc1NC] |
| IV-27 | 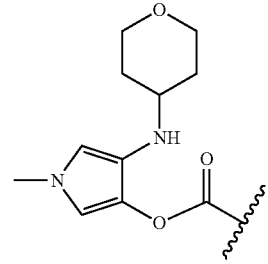 |
| IV-28 | 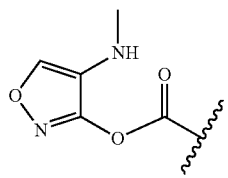 [SMILES: *C(=O)Oc1nocc1NC] |

TABLE 4A-continued
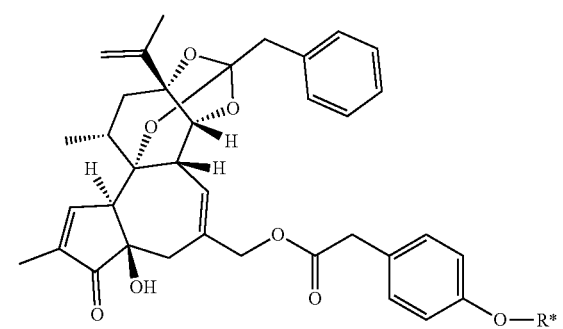
| No. | R* |
|---|---|
| IV-29 |  |
| IV-30 | 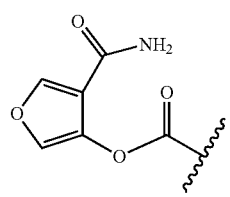 [SMILES: *C(=O)Oc1cocc1C(N)=O] |
TABLE 5
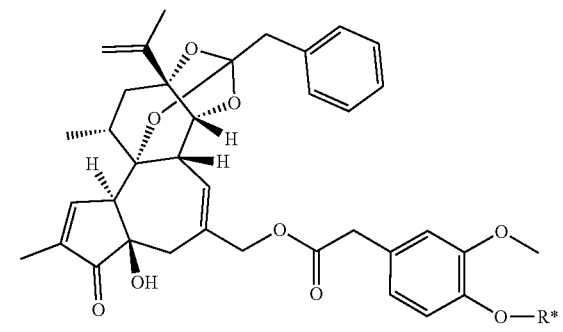
| No. | R* |
|---|---|
| V-1 | 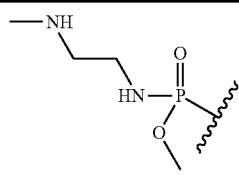 |
| V-2 | 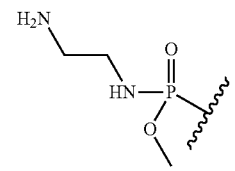 [SMILES: *P(=O)(NCCN)OC] |
TABLE 5-continued
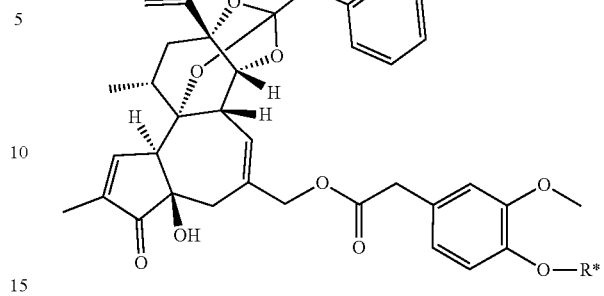
| No. | R* |
|---|---|
| V-3 | 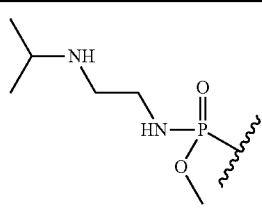 |
| V-4 | 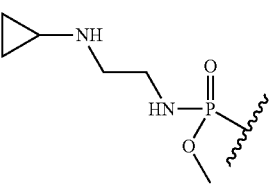 [SMILES: *P(=O)(NCCNC1CC1)OC] |
| V-5 | 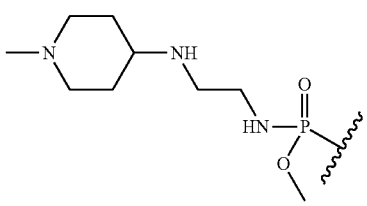 [SMILES: *P(=O)(NCCNC1CCN(C)CC1)OC] |
| V-6 | 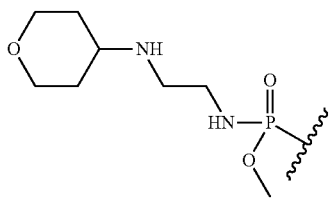 [SMILES: *P(=O)(NCCNC1CCOCC1)OC] |
| V-7 | 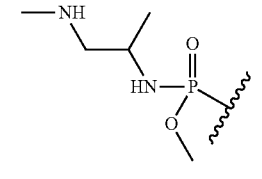 [SMILES: *P(=O)(NC(C)CNC)OC] |
| V-8 | 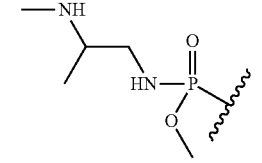 [SMILES: *P(=O)(NCC(C)NC)OC] |

TABLE 5-continued

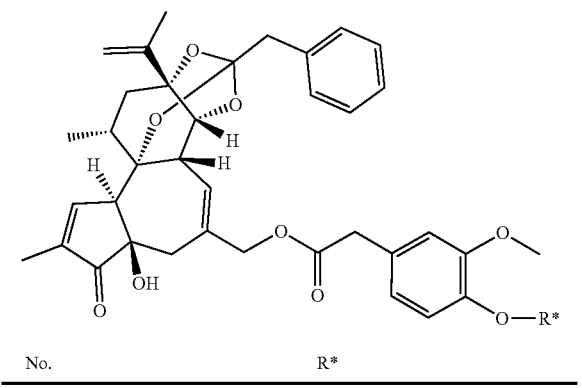

| No. | R* |
|---|---|
| V-9 | —NH–CH(CH₃)–CH(CH₃)–NH–P(=O)(OCH₃)– |
| V-10 | —NH–C(CH₃)₂–CH₂–NH–P(=O)(OCH₃)– |
| V-11 | —NH–CH₂–C(CH₃)₂–NH–P(=O)(OCH₃)– |
| V-12 | —NH–C(cyclopropyl)(CH₂–NH–P(=O)(OCH₃)–) |
| V-13 | —NH–CH₂–C(cyclopropyl)–NH–P(=O)(OCH₃)– |
| V-14 | —NH–CH(cyclopropyl)–CH₂–NH–P(=O)(OCH₃)– |
| V-15 | —NH–CH(1-methylpiperidin-4-yl)–CH₂–NH–P(=O)(OCH₃)– |

TABLE 5-continued

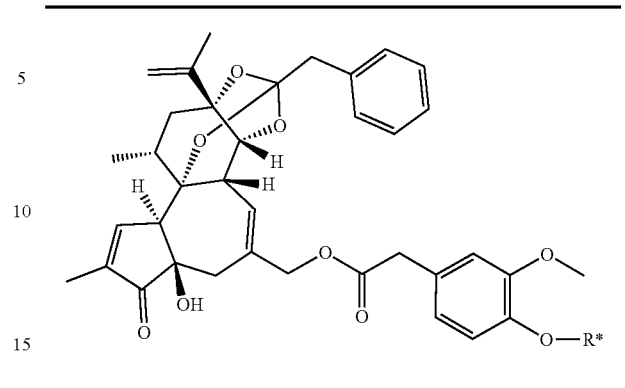

| No. | R* |
|---|---|
| V-16 | —NH–CH(t-Bu)–CH₂–NH–P(=O)(OCH₃)– |
| V-17 | —NH–CH₂CH₂–NH–P(=O)(OCH₃)– |
| V-18 | —NH–CH₂CH₂–NH–P(=O)(OEt)– |
| V-19 | —NH–CH₂CH₂–NH–P(=O)(O-iPr)– |
| V-20 | —NH–CH₂CH₂–NH–P(=O)(O-cyclopropyl)– |

TABLE 5-continued
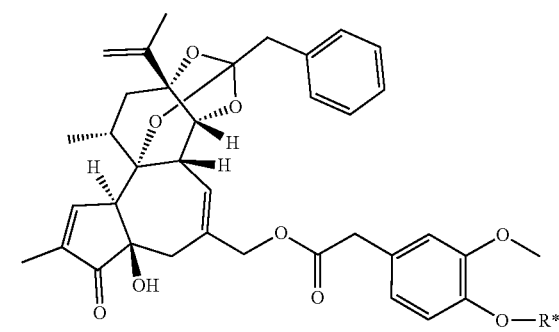
| No. | R* |
|---|---|
| V-21 | 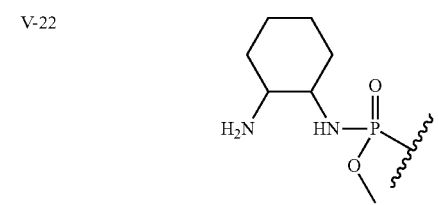 |
| V-22 | 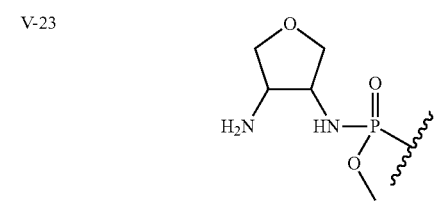 |
| V-23 | 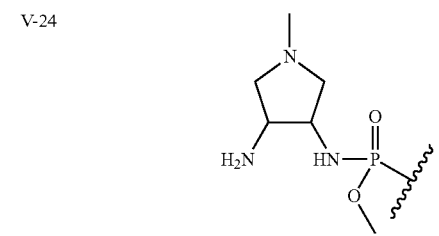 |
| V-24 | 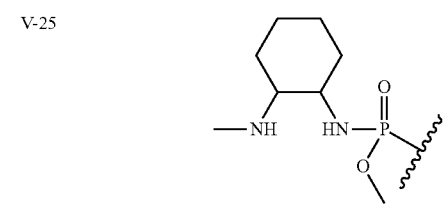 |
| V-25 | |
TABLE 5-continued
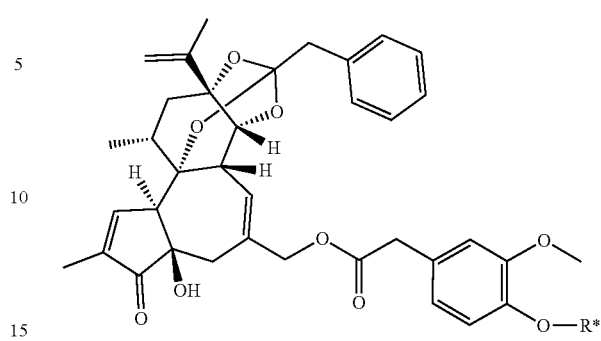
| No. | R* |
|---|---|
| V-26 | |
| V-27 | |
| V-28 | |
| V-29 | |
| V-30 | |

TABLE 5A
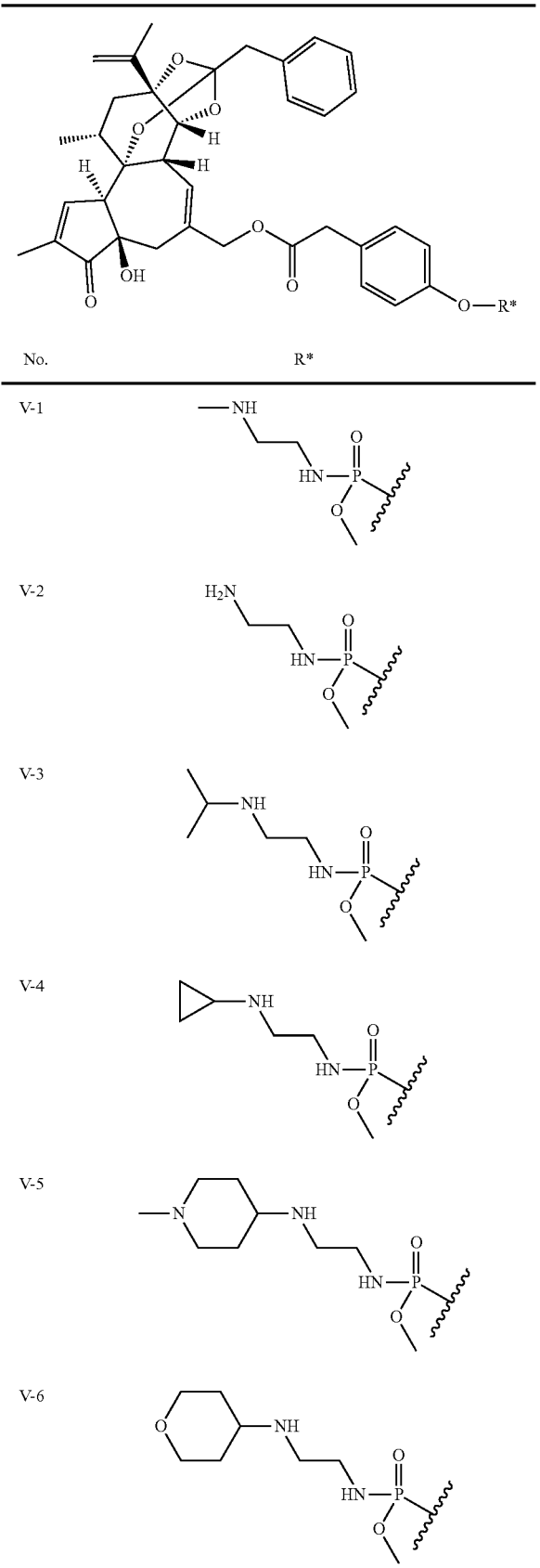
TABLE 5A-continued
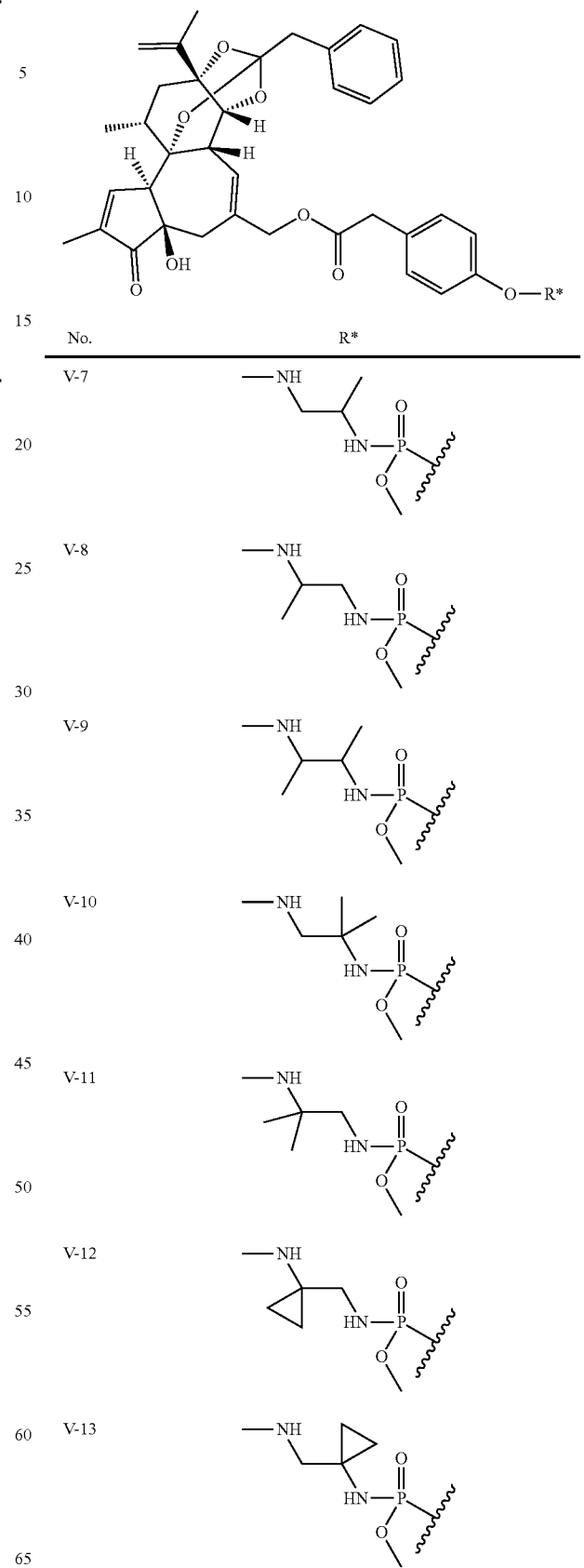

TABLE 5A-continued
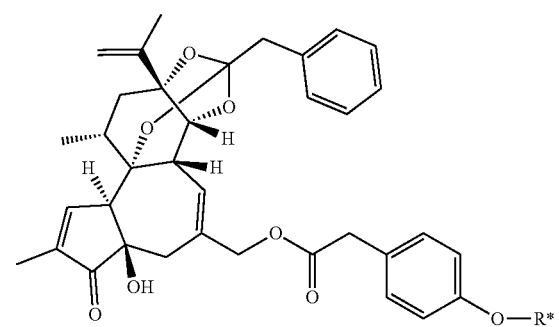
| No. | R* |
|---|---|
| V-14 | 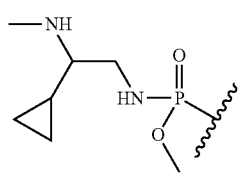 |
| V-15 | 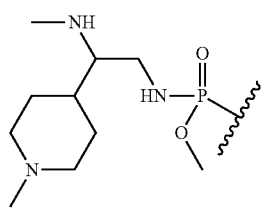 [SMILES: *P(=O)(NCC(NC)C1CCN(C)CC1)OC] |
| V-16 | 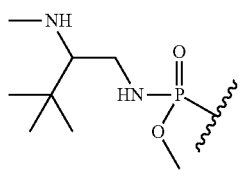 [SMILES: *P(=O)(NCC(NC)C(C)(C)C)OC] |
| V-17 | 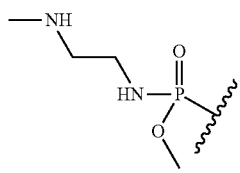 [SMILES: *P(=O)(NCCNC)OC] |
| V-18 | 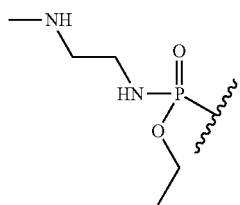 [SMILES: *P(=O)(NCCNC)OCC] |
| V-19 | 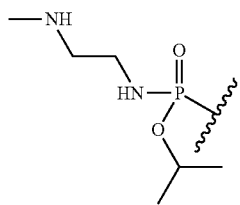 [SMILES: *P(=O)(NCCNC)OC(C)C] |
TABLE 5A-continued
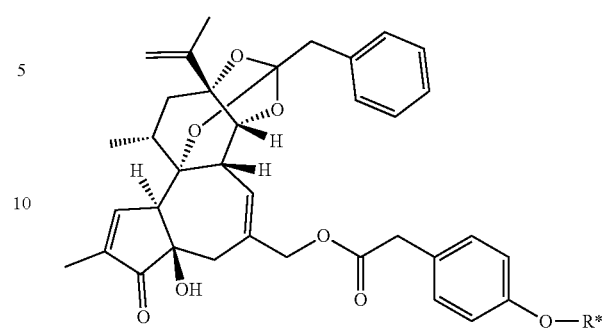
| No. | R* |
|---|---|
| V-20 | 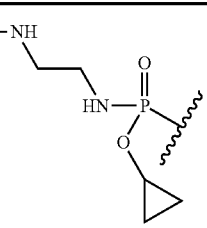 |
| V-21 | 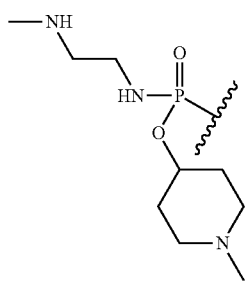 |
| V-22 | 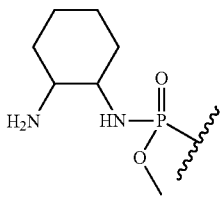 [SMILES: *P(=O)(NC1CCCCC1N)OC] |
| V-23 | 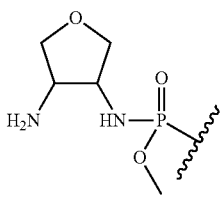 [SMILES: *P(=O)(NC1COCC1N)OC] |
| V-24 | 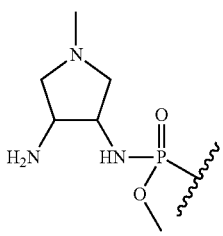 [SMILES: *P(=O)(NC1CN(C)CC1N)OC] |

TABLE 5A-continued

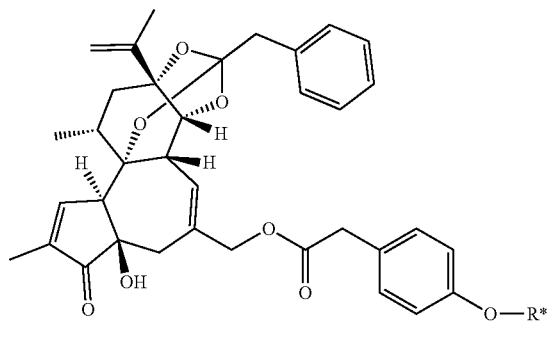

| No. | R* |
|---|---|
| V-25 | 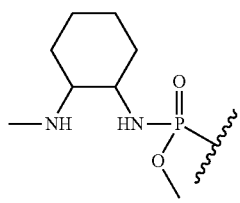 [SMILES: *P(=O)(NC1CCCCC1NC)OC] |
| V-26 | 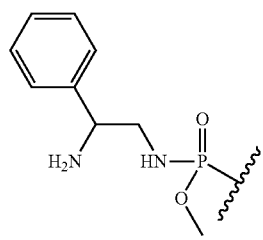 [SMILES: *P(=O)(NCC(N)c1ccccc1)OC] |
| V-27 | 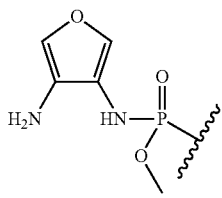 [SMILES: *P(=O)(Nc1cocc1N)OC] |
| V-28 | 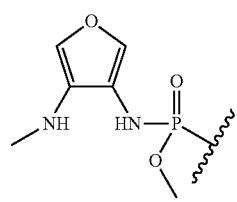 [SMILES: *P(=O)(Nc1cocc1NC)OC] |

TABLE 5A-continued

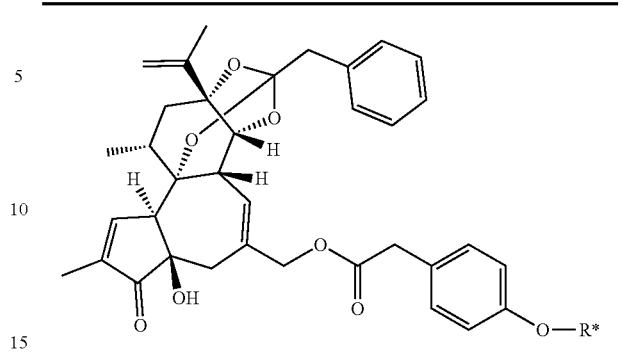

| No. | R* |
|---|---|
| V-29 | 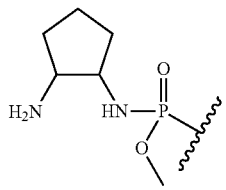 |
| V-30 | 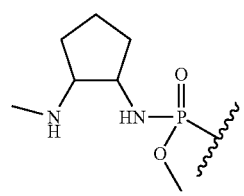 [SMILES: *P(=O)(NC1CCCC1NC)OC] |

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

Scheme 1 illustrates a general method of forming carbamate compounds C and E, such as those defined by Formula I and Formula II and those depicted in Table 1. Resiniferatoxin or a related compound A and secondary amine B can be coupled to form a carbamate under a variety of known conditions, for example, with 4-nitrophenylchloroformate and a base, for example Hunig's base or potassium t-butoxide, in a solvent, such as dichloromethane. Removal of the amine protecting group (PG) under suitable conditions affords carbamate C. For example, when PG is Boc, it can be removed, for example, by treatment with an acid, such as trifluoroacetic acid. When PG is Bn, it can be removed, for example, by hydrogenolysis (for example, catalyzed by palladium on carbon with hydrogen gas or ammonium formate) or dissolving metal reduction (for example, with sodium metal in liquid ammonia). According to similar methods, resiniferatoxin or a related compound A and primary or secondary amine D can be coupled and deprotected to afford carbamate E. Variables $R^1$, $R^2$, $R^3$, $R^4$, A, and n may be, for example, as defined above in connection with Formulae I and II.

SCHEME 1

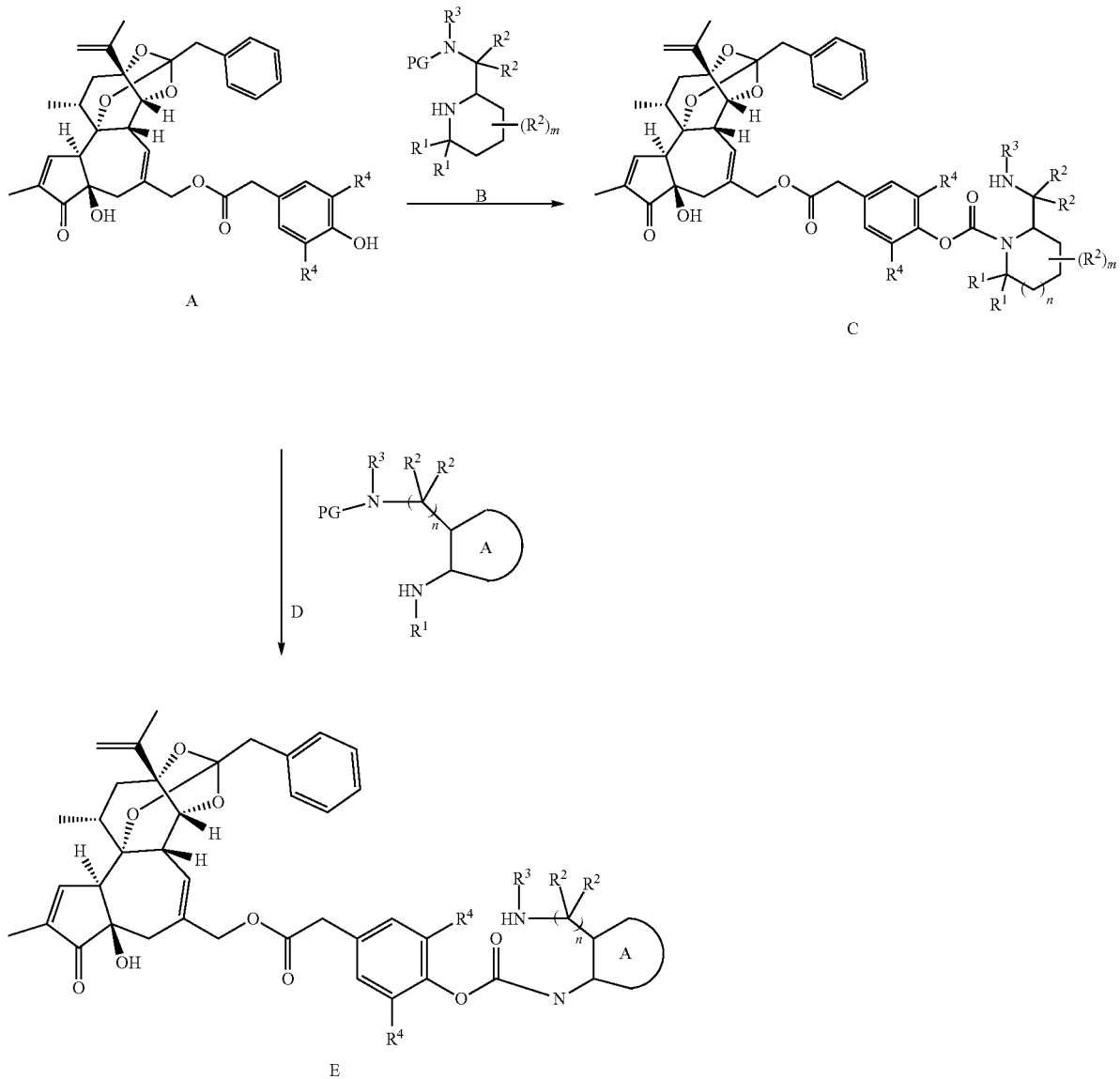

Scheme 2 illustrates a general method of forming aminooxoacetate compounds C, such as those defined by Formula IV and those depicted in Table 2. Resiniferatoxin or a related compound A and primary or secondary amine B can be coupled to form an aminooxoacetate under a variety of known conditions, for example, with oxalyl chloride and a base, for example Hunig's base or potassium t-butoxide, in a solvent, such as dichloromethane. Removal of the amine protecting group (PG) under suitable conditions affords aminooxoacetate C. For example, when PG is Boc, it can be removed, for example, by treatment with an acid, such as trifluoroacetic acid. When PG is Bn, it can be removed, for example, by hydrogenolysis (for example, catalyzed by palladium on carbon with hydrogen gas or ammonium formate) or dissolving metal reduction (for example, with sodium metal in liquid ammonia). Variables $R^1$, $R^{2A}$, $R^{2B}$, $R^3$, $R^4$, and n may be, for example, as defined above in connection with Formula IV.

SCHEME 2

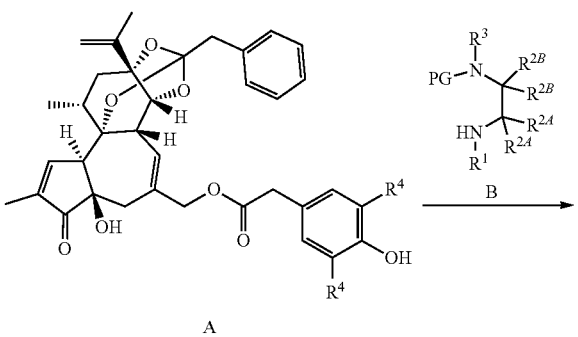

-continued

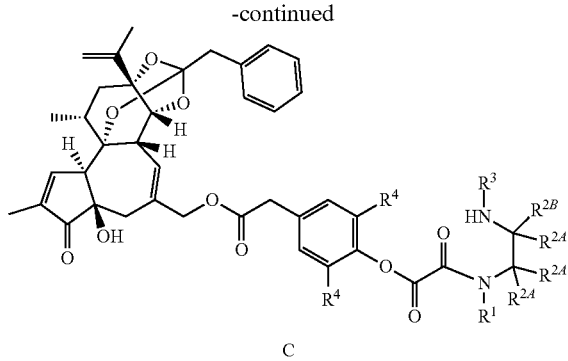

C

Scheme 3 illustrates a general method of forming ester compounds C, such as those defined by Formula III (when X is —C(R')$_2$— or a bond) and those depicted in Table 3. Resiniferatoxin or a related compound A and carboxylic acid B can be coupled to form an ester under a variety of known conditions, for example, with a coupling reagent, such as CDI or EDCI/HOBt, and a base, for example Hunig's base or potassium t-butoxide, in a solvent, such as dichloromethane or DMF. Removal of the amine protecting group (PG) under suitable conditions affords ester C. For example, when PG is Boc, it can be removed, for example, by treatment with an acid, such as trifluoroacetic acid. When PG is Bn, it can be removed, for example, by hydrogenolysis (for example, catalyzed by palladium on carbon with hydrogen gas or ammonium formate) or dissolving metal reduction (for example, with sodium metal in liquid ammonia). Variables R$^1$, R$^3$, R$^4$, Y, A, and n may be, for example, as defined above in connection with Formula III.

Scheme 4 illustrates a general method of forming carbonate compounds C, such as those defined by Formula III (when X is —O—) and those depicted in Table 4. Resiniferatoxin or a related compound A and hydroxylated cyclic compound B can be coupled to form a carbonate under a variety of known conditions, for example, with a coupling reagent (for example, CDI, 4-nitrophenylchloroformate, or triphosgene), and a base, for example Hunig's base or potassium t-butoxide, in a solvent, such as dichloromethane. Removal of the amine protecting group (PG) under suitable conditions affords carbonate C. For example, when PG is Boc, it can be removed, for example, by treatment with an acid, such as trifluoroacetic acid. When PG is Bn, it can be removed, for example, by hydrogenolysis (for example, catalyzed by palladium on carbon with hydrogen gas or ammonium formate) or dissolving metal reduction (for example, with sodium metal in liquid ammonia). Variables R$^3$, R$^4$, Y, A, and n may be, for example, as defined above in connection with Formula III.

SCHEME 4

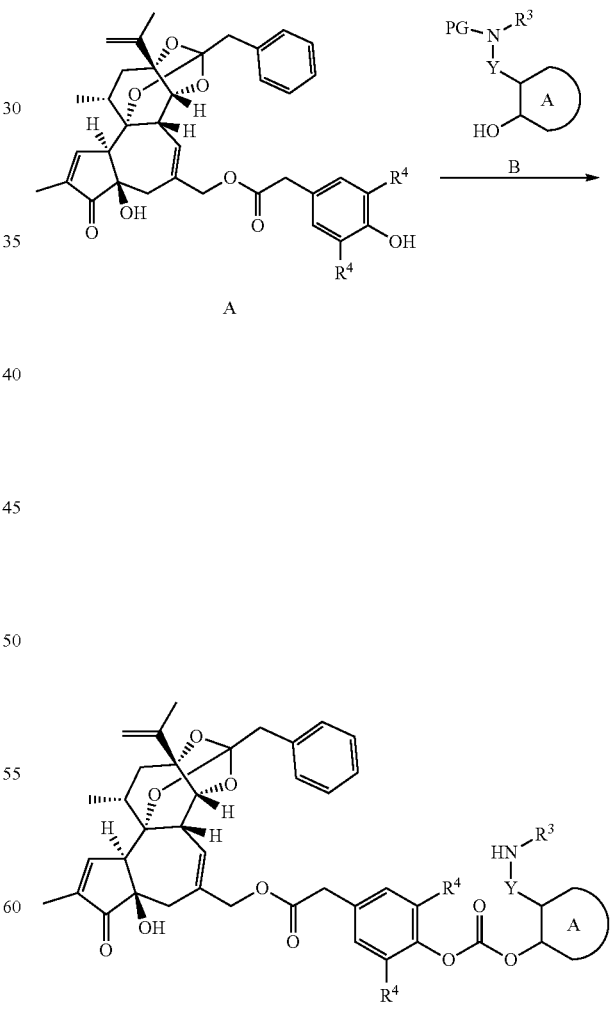

SCHEME 3

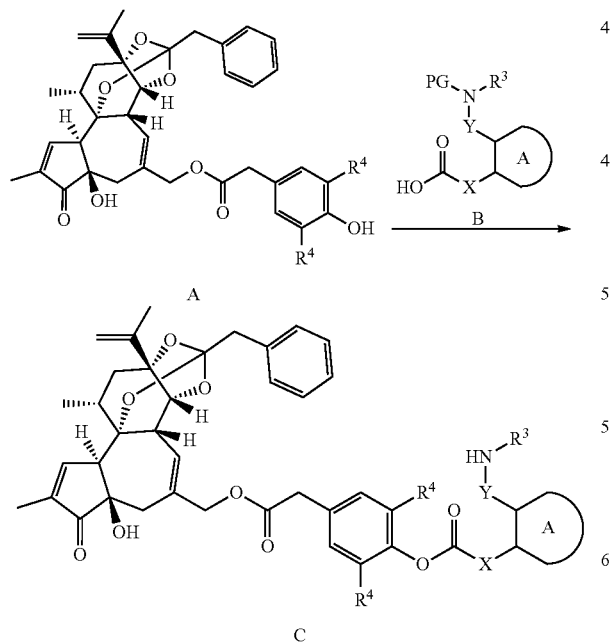

X is -C(R$^1$)$_2$- or a bond

Scheme 5 illustrates a general method of forming phosphoramidite compounds D, such as those defined by Formula V and those depicted in Table 5. Resiniferatoxin or a related compound A can be condensed with dichlorophosphate B then primary or secondary amine C to form a phosphoramidite, for example, in the presence of a base, for example Hunig's base, pyridine, or potassium t-butoxide, in a solvent, such as dichloromethane or DMF. Removal of the amine protecting group (PG) under suitable conditions affords phosphoramidite D. For example, when PG is Boc, it can be removed, for example, by treatment with an acid, such as trifluoroacetic acid. When PG is Bn, it can be removed, for example, by hydrogenolysis (for example, catalyzed by palladium on carbon with hydrogen gas or ammonium formate) or dissolving metal reduction (for example, with sodium metal in liquid ammonia). Variables $R^1$, $R^{2A}$, $R^{2B}$, $R^3$, $R^4$, $R^5$, and n may be, for example, as defined above in connection with Formula V.

Exemplary procedures for preparing exemplary starting materials described in the preceeding synthetic schemes are provided below.

Scheme 6 illustrates a general method for preparing substituted piperidine derivatives, such as the secondary amine B in Schemes 1 and 2 (when $R^1$ and one instance of $R^{2A}$ form a heterocyclic ring). Treating the starting nitrile A1 with a suitable organometallic reagent (for example, an alkyllithium, Grignard reagent, or hydride) results in a metalloiminium intermediate, which can then be reacted with the same organometallic reagent or a different organometallic reagent to afford the primary amine B1. Optional functionalization of the primary amine (for example, by nucleophilic addition of the amine to $R^3X$; or reductive amination of the amine with an aldehyde or ketone, for example, formaldehyde when $R^3$=Me), followed by benzyl protection (for example, with BnBr and a base, such as Hunig's base), provides benzyl-protected amine C1.

Alternatively, addition of a single equivalent of an organometallic agent to nitrile A1, followed by aqueous workup, affords a ketone or aldehyde, which is condensed with a suitable amine ($R^3NH_2$), for example, with catalytic acid and dehydration via azeotrope or molecular sieves, to afford imine B1'. Nucleophilic addition of an organometallic agent, followed by benzyl protection, provides benzyl-protected amine C1.

Radical bromination of the alkene in C1 (for example, with HBr and UV light or hydrogen peroxide), followed by nucleophilic displacement of the resulting primary bromide with triphenylphosphine, provides a Wittig reagent. Deprotonation of the Wittig reagent, for example, with a base such as BuLi, followed by condensation with an appropriate ketone or aldehyde ($R^1C(O)R^1$) provides alkene D1. Acid-catalyzed Boc-deprotection and carbocationic cyclization, for example, with trifluoroacetic acid, provides the piperidine E1 (PG=Bn).

Alternatively, olefin cross-metathesis of C1 with a vinyl ketone ($R^1C(O)$—CH=$CH_2$), for example, using a ruthenium carbene catalyst, followed by chemoselective reduction of the alkene, for example, with Stryker's reagent or $NaBH_4$, provides ketone D1'. Acid-catalyzed Boc-deprotection and dehydration, for example, with trifluoroacetic acid, provides a cyclic imine, which undergoes nucleophilic addition of an organometallic agent to afford piperidine E1 (PG=Bn). Piperidines with other protecting groups (e.g., PG=Boc) can be prepared by protecting the piperidine nitrogen with an orthogonal protecting group (e.g. trifluoroacetamide, for example, by treating with trifluoroacetic acid anhydride), deprotecting the benzyl amine (e.g., via hydrogenolysis or dissolving metal reduction), reprotecting the liberated nitrogen (e.g., as PG=Boc), and deprotecting the orthogonal protecting group (e.g., trifluoroacetamide deprotection with, for example, $K_2CO_3$ in methanol).

SCHEME 5

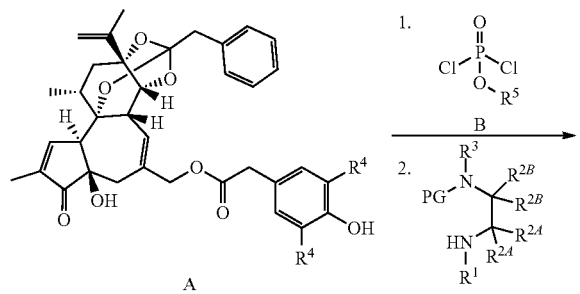

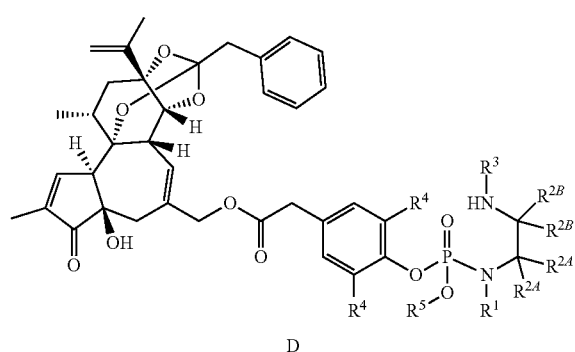

A

D

SCHEME 6

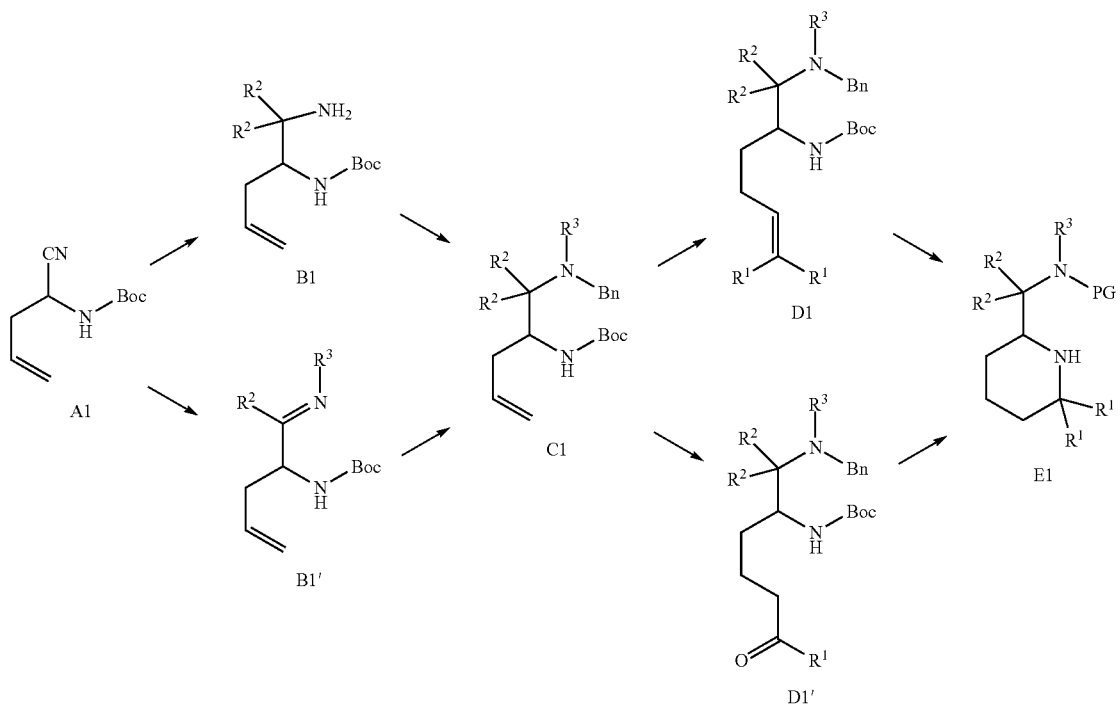

Scheme 7 illustrates a general method for preparing aminomethyl-substituted benzoic acids and heteroaromatic carboxylic acids, such as carboxylic acid B in Scheme 3 (when X is a bond, Y is —C($R^2$)$_2$—, and A is a carbocyclic aromatic or heteroaromatic ring). Treating the starting nitrile A1 with a suitable organometallic reagent (for example, a Grignard reagent or hydride) results in a metalloiminium intermediate, which can then be reacted with the same organometallic reagent or a different organometallic reagent to afford the primary amine B1. Optional functionalization of the primary amine (for example, by nucleophilic addition of the amine to $R^3X$; or reductive amination of the amine with an aldehyde or ketone, for example, formaldehyde when $R^3$=Me), followed by benzyl protection (for example, with BnBr and a base, such as Hunig's base), provides benzyl-protected amine C1.

Alternatively, addition of a single equivalent of an organometallic agent to nitrile A1, followed by aqueous workup, affords a ketone or aldehyde, which is condensed with a suitable amine ($R^3NH_2$), for example, with catalytic acid and dehydration via azeotrope or molecular sieves, to afford imine B1'. Nucleophilic addition of an organometallic agent, followed by benzyl protection, provides benzyl-protected amine C1.

Starting from C1, a carboxylic acid moiety is introduced by lithiation, for example, with BuLi, and trapping the resulting aryl or heteroaryl lithium species with carbon dioxide to provide carboxylic acid D1 (PG=Bn). Carboxylic acids with other amine protecting groups (e.g., PG=Boc) can be prepared by deprotecting the benzyl amine (e.g., via hydrogenolysis or dissolving metal reduction) and reprotecting the liberated nitrogen (e.g., as PG=Boc).

SCHEME 7

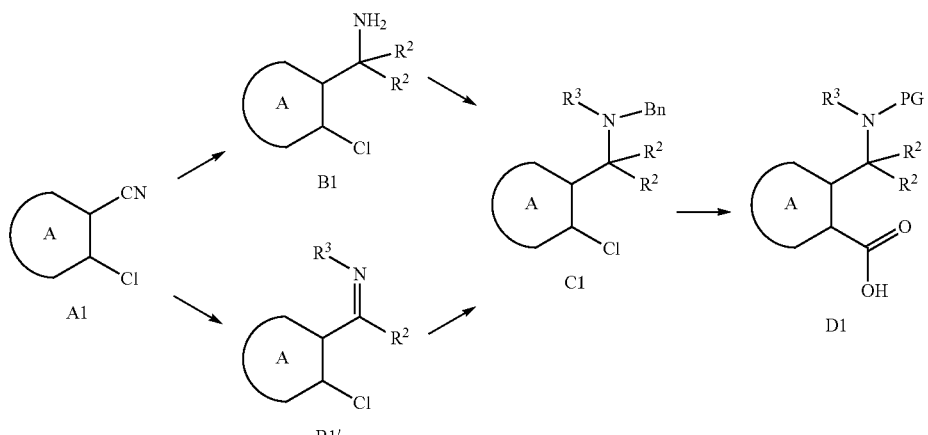

Ring A is a carbocyclic aromatic or heteroaromatic ring

Scheme 8 illustrates general procedures for preparation of a variety of phosphoramidate analogs (9B, 9D, 9F, 9H) from commercially available phosphorochloridates (9A, 9C, 9E, 9G). Three of the analogs are prepared from benzyl methyl phosphorochloridate. The chlorine is displaced with the requisite amine followed by reductive removal of the benzyl protecting group to afford the desired phosphoramidate. Preparation of 9F begins with benzyl phosphorodichloridate. Successive treatment with tert-butyl (2-aminoethyl)(methyl) carbamate then cyclopropyl alcohol, followed by reductive removal of the benzyl protecting group, affords 9F.

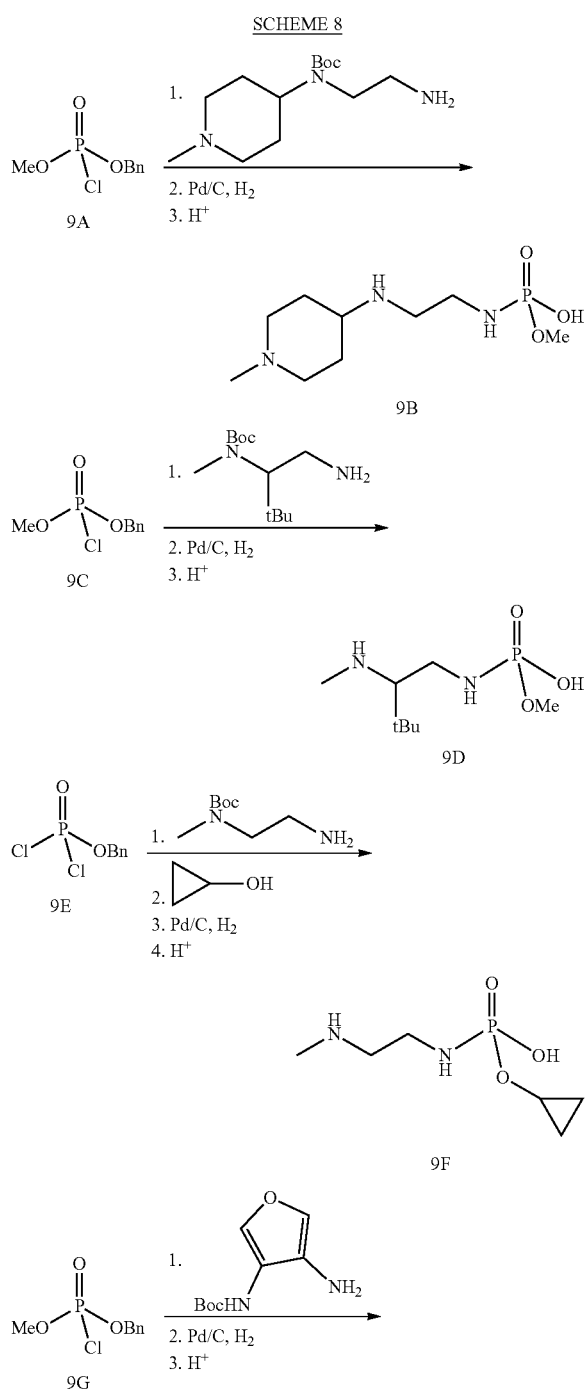

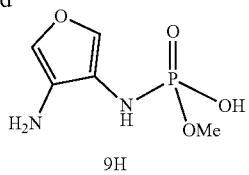

II. Therapeutic Applications of Prodrug Compounds

Prodrug compounds described herein, such as a compound of Formula I, II, III, IV, or V, or other compound in Section I, may be used to treat subjects suffering from pain. The prodrug compounds may also be used to treat subjects suffering from itch.

Treatment and Prevention of Pain

One aspect of the invention provides a method of treating or preventing pain in a subject. The method comprises administering a therapeutically effective amount of a prodrug compound described herein, such as a compound of Formula I, II, III, IV, or V, or other compound in Section I, to a subject in need thereof to treat or prevent the pain. In certain embodiments, the particular compound of Formula I, II, III, IV, or V, is a compound defined by one of the embodiments described above.

In certain embodiments, the method is for treating pain. In certain embodiments, the method is for preventing pain.

In certain embodiments, the pain is post-operative pain. In certain embodiments, the post-operative pain is due to surgery on the subject's shoulder, elbow, wrist, hand, spine, hip, knee, ankle, foot, abdomen, neck, or head. In certain embodiments, the post-operative pain is due to a bunionectomy, dental extraction, flank incision, hip replacement, knee replacement, laparoscopy, laparotomy, repair of a broken bone, repair of a torn ligament, repair of bone fracture, rotator cuff repair, surgery on a knee ligament, a thoracoabdominal incision, thoracotomy, or abdominoplasty. In certain embodiments, the post-operative pain is due to knee replacement. In certain embodiments, the post-operative pain is due to endoscopic surgery.

In certain embodiments, the post-operative pain is due to surgery on the subject's spine. In certain embodiments, the post-operative pain is due to surgery on the subject's lumbar spine, thoracic spine, or cervical spine. In certain embodiments, the post-operative pain is due to surgery on the subject's spine, and the method comprises administering the prodrug compound intrathecally to the subject.

In certain embodiments, the post-operative pain is due to surgery on the subject's foot. In certain embodiments, the post-operative pain is due to surgery on the subject's foot due to plantar fasciitis.

In certain embodiments, the post-operative pain is due to surgery to address pain due to a damaged nerve. In certain embodiments, the post-operative pain is due to surgery to address pain due to a neuroma. In certain embodiments, the post-operative pain is due to surgery to address pain from a nerve, and the method comprises administering the prodrug compound to the nerve. In certain embodiments, the post-operative pain is due to surgery to address pain from a nerve, and the method comprises administering the prodrug compound to dorsal root ganglia, or trigeminal ganglion.

In certain embodiments, the pain is chronic pain. In certain embodiments, the chronic pain is arthritic pain, trauma pain, musculoskeletal pain, pain due to an inflammatory disease, or pain due to a non-inflammatory disease. In certain embodiments, the chronic pain is arthritic pain. In certain embodiments, the arthritic pain is osteoarthritis pain.

In certain embodiments, the arthritic pain is rheumatoid arthritis pain. In certain embodiments, the chronic pain is due to a neuroma.

In certain embodiments, the chronic pain is nociceptive pain, neuropathic pain, pain due to nerve injury, pain from a neuralgia, pain from a neuroma, pain from a myalgia, pain due to cancer, pain due to bursitis, pain due to tendonitis, or pain associated with an orthopedic disorder.

In certain embodiments, the chronic pain is located in the subject's shoulder, elbow, wrist, hand, spine, hip, knee, ankle, foot, abdomen, neck, or head. In certain embodiments, the chronic pain is located in a joint of the subject. In certain embodiments, the joint is a knee joint, hip joint, shoulder joint, elbow joint, ankle joint, carpal joint, tarsal joint, or metatarsal joint. In certain embodiments, the joint is a knee joint. In certain embodiments, the compound is administered to the intra-articular space of the joint.

In certain embodiments, the chronic pain is located in the subject's spine. In certain embodiments, the chronic pain is located in the subject's lumbar spine, thoracic spine, or cervical spine.

In certain embodiments, the chronic pain is located in a joint of the subject and the prodrug compound is administered to the intra-articular space of the joint. In certain embodiments, the chronic pain is located in the spine of the subject, and the prodrug compound is administered intrathecally.

In certain other embodiments, the chronic pain is back pain, fibromyalgia, craniofacial pain, trigeminal neuralgia, obturator neuralgia, femoral neuralgia, sciatica neuralgia, post-herniorrhaphy pain, Morton's neuroma, pain due to a mastectomy, stump pain, pain associated with median sternotomy, psoriatic arthritis pain, pain due to ankylosing spondylitis, pain due to a heel spur, pain associated with a laparoscopic cholecystectomy, pain due to diabetic neuropathy, or pain due to multiple sclerosis.

In certain other embodiments, the chronic pain is:
chronic pain associated with myofascial pain syndrome, a trigger point, a tender point, thoracic outlet syndrome, complex regional pain syndrome, reflex sympathetic dystrophy (RSD), or sympathetically maintained pain (SMP);
chronic pain associated with traumatic injury to the peripheral nervous system, herpes zoster (also known as shingles, or post-herpetic neuropathy) or similar infections that attack and damage nerve fibers or endings;
pain associated with a sarcoma or carcinoma;
neuropathic pain associated with chemotherapy treatment;
plantar fasciitis;
pain associated with an autoimmune disease;
focal pain in the skin due to tumor;
pain associated with oral mucositis due to radiation therapy;
pain associated with radiation dermatitis;
idiopathic pain;
central nervous system pain, including pain due to spinal cord or brain stem damage;
chronic pain due to low back pain, sciatica, headache (including migraine, chronic tension headache, and cluster headache), temporomandibular disorder (TMJ) pain, maxillary sinus pain, or complex regional pain syndrome; or
chronic pain associated with hyperesthesia, allodynia, hyperalgesia, deafferentation pain, or non-nociceptive chronic pain.

In yet other embodiments, the chronic pain is chronic pain resulting from:
a musculoskeletal disorder such as osteoarthritis/degenerative joint disease/spondylosis, rheumatoid arthritis, lyme disease, reiter syndrome, disk herniation/facet osteoarthropathy, fracture/compression fracture of lumbar vertebrae, faulty or poor posture, fibromyalgia, polymyalgia rheumatica, mechanical low back pain, chronic coccygeal pain, muscular strains and sprains, pelvic floor myalgia (levator ani spasm), piriformis syndrome, rectus tendon strain, hernias (e.g., obturator, sciatic, inguinal, femoral, spigelian, perineal, umbilical), abdominal wall myofascial pain (trigger points), or chronic overuse syndromes (e.g., tendinitis, bursitis); or
a neurological disorder such as brachial plexus traction injury, cervical radiculopathy, thoracic outlet syndrome, spinal stenosis, arachnoiditis syndrome, metabolic deficiency myalgias, polymyositis, neoplasia of spinal cord or sacral nerve, cutaneous nerve entrapment in surgical scar, postherpetic neuralgia (shingles), neuralgia (e.g., iliohypogastric, ilioinguinal, or genitofemoral nerves), polyneuropathies, polyradiculoneuropathies, mononeuritis multiplex, chronic daily headaches, muscle tension headaches, migraine headaches, temporomandibular joint dysfunction, temporalis tendonitis, sinusitis, atypical facial pain, trigeminal neuralgia, glossopharyngeal neuralgia, nervus intermedius neuralgia, sphenopalatine neuralgia, referred dental or temporomandibular joint pain, abdominal epilepsy, abdominal migraine, urologic disorders, bladder neoplasm, chronic urinary tract infection, interstitial cystitis, radiation cystitis, recurrent cystitis, recurrent urethritis, urolithiasis, uninhibited bladder contractions (detrusor-sphincter dyssynergia), urethral diverticulum, chronic urethral syndrome, urethral carbuncle, prostatitis, urethral stricture, testicular torsion, or peyronie disease.

In a more specific embodiment, the pain is one or more of the following:
nociceptive pain;
neuropathic pain;
pain from neuralgia;
pain from myalgias;
pain associated with a painful trigger point;
pain from a tumor in soft tissue;
pain associated with a neurotransmitter-dysregulation syndrome;
pain associated with an orthopedic disorder such as a condition of the foot, knee, hip, spine, shoulders, elbow, hand, head and neck that require surgery;
a neuropathy selected from
a syndrome of acute ascending motor paralysis with variable disturbance of sensory function (e.g., idiopathic polyneuritis, Landry-Guillain-Barre Syndrome, acute immune-mediated polyneuritis, infectious mononucleosis polyneuritis, hepatitis polyneuritis; diptheric polyneuropathy; porphyric polyneuropathy; toxic polyneuropathy (e.g., thallium); acute axonal polyneuropathy; acute panautonomic neuropathy; vaccinogenic, serogenic, paraneoplastic, polyareteric and lupus polyneuropathy; syndromes of subacute sensorimotor paralysis; syndromes of acquired forms of chronic sensorimotor polyneuropathy; syndromes of determined forms of genetic chronic polyneuropathy);

a syndrome of recurrent or relapsing polyneuropathy; and a syndrome of mononeuropathy or multiple neuropathies;

a syndrome of subacute sensorimotor paralysis selected from the group consisting of deficiency states (e.g., beriberi, pellagra, vitamin B 12); heavy metal/industrial solvent poisonings (e.g., arsenic, lead); drug overdose (e.g., isoniazid, disulfuram, vincristine, taxol, chloramphenicol); uremic polyneuropathy; diabetes; sarcoidosis; ischemic neuropathy and peripheral vascular disease; AIDS; and radiation (radiotherapy);

a syndrome of chronic sensorimotor neuropathy selected from the group consisting of carcinoma, myeloma and other malignancies; paraproteinemias; uremia; beriberi (usually subacute), diabetes, hypo/hyperthyroidism; connective tissue disease; amyloidosis; leprosy and sepsis;

a genetic chronic polyneuropathy selected from the group consisting of dominant mutilating sensory neuropathy (adult); recessive mutilating sensory neuropathy (childhood); congenital insensitivity to pain; spinocerebellar degenerations, Riley Day Syndrome; Universal Anesthesia Syndrome; polyneuropathies with metabolic disorder; and mixed sensorimotor-autonomic type polyneuropathies;

a recurrent/relapsing polyneuropathy selected from the group consisting of idiopathic polyneuritis; porphyria; chronic inflammatory polyradiculoneuropathy; mononeuritis multiplex; beriberi/drug overdose; refsum disease and tangier disease;

a mono/multiple neuropathy selected from the group consisting of pressure palsies; traumatic neuropathies (e.g., irradiation or electrical injury); serum, vaccinogenic (e.g., rabies, smallpox); herpes zoster; neoplastic infiltration; leprosy; diptheretic wound infections; migrant sensory neuropathy; shingles and post herpetic neuralgia;

chronic post-herniorrhaphy pain;

bone pain;

length dependent neuropathy, such as small fiber neuropathy;

pain associated with Morton's Neuroma;

pain associated with mastectomy;

pain associated with median sternotomy;

pain associated with arthritis;

pain associated with bursitis, tendonitis, osteoarthritis, or rheumatoid arthritis; or back pain, heel spur pain, or pain associated with laparoscopic cholecystectomy.

Duration of and Magnitude of Relief from Pain

The methods may be further characterized by the duration of relief from pain. For example, in certain embodiments, the method ameliorates post-operative pain for a duration of at least 3 days after administration of the prodrug compound, such as a compound of Formula I. In certain embodiments, the method ameliorates pain for a duration of at least 5 days after administration of the prodrug compound. In certain embodiments, the method ameliorates pain for a duration of at least 7 days after administration of the prodrug compound. In certain embodiments, the method ameliorates pain for a duration of at least 2 weeks, at least 4 weeks, at least 8 week, or at least 12 weeks after administration of the prodrug compound. In certain embodiments, the method ameliorates pain for a duration of at least 4, 5, 6, 7, 8, 9, 10, 11, or 12 months after administration of the prodrug compound.

The methods may be further characterized by the magnitude of relief from pain. For example, in certain embodiments, the method provides a reduction in maximal daily post-operative pain by at least 20%, 30%, 40%, 50%, 60%, 70%, 80% or 90%. The magnitude of daily pain experienced by the subject may be evaluated using procedures described in the literature for evaluating the magnitude of pain, such as Numerical Pain Rating Scale (where 0 is no pain, and 10 is worst imaginable pain).

Use of a Cooling Article

The methods may be further characterized by the use of a cooling article. For example, in certain embodiments, a cooling article is applied to the subject's skin in proximity to the site of pain in proximity to the time in which the prodrug compound (e.g., a compound of Formula I) is administered to the subject. In certain embodiments, a cooling article is applied to the subject's skin in proximity to the site of pain prior to administering a prodrug compound (e.g., a compound of Formula I), in order to reduce the temperature of tissue in proximity to the site of pain.

In certain other embodiments, a cooling article is applied to the subject's skin in proximity to the site of pain after administering a prodrug compound (e.g., a compound of Formula I), in order to reduce the temperature of tissue in proximity to the site of pain or to maintain a reduced temperature for such tissue for a certain duration of time.

Cooling Article Applied to Subject Prior to Administering Prodrug Compound

In certain embodiments, a cooling article is applied to the subject's skin in proximity to the site of pain prior to administering a prodrug compound (e.g., a compound of Formula I), in order to reduce the temperature of tissue in proximity to the site of pain. This can improve the efficacy of resiniferatoxin or a related compound in denerveating tissue in proximity to a site of pain. Additionally, reducing the temperature of tissue in proximity to the site of pain prior to administration of the prodrug compound can reduce the amount and/or duration of temporary pain experienced by the subject due to resiniferatoxin or a related compound produced by the prodrug compound.

In an embodiment, the methods may be further characterized according to the temperature achieved for tissue in proximity to the site of pain when the prodrug compound, such as a compound of Formula I, is administered to the subject, due to application of the cooling article. In certain embodiments, the temperature achieved for tissue in proximity to the site of pain ranges of from about 20° C. to about 30° C., about 20° C. to about 22° C., about 22° C. to about 24° C., about 24° C. to about 26° C., about 26° C. to about 28° C., or about 28° C. to about 30° C. In a more specific embodiment, the cooling article is applied to the subject's skin in proximity to the site of pain prior to administering the prodrug compound, in order to achieve a temperature of about 20, 21, 22, 23, 24, 25, 26, 27, 28, 29, or 30° C. for tissue in proximity to the site of pain.

The methods may be further characterized according to the duration of time for which the cooling article is applied to the subject prior to administering the prodrug compound, such as a compound of Formula I. For example, in certain embodiments, the cooling article is applied to the subject's skin in proximity to the site of pain for a duration of at least 10 minutes. In certain embodiments, the cooling article is applied to the subject's skin in proximity to the site of pain for a duration of at least 15 minutes. In certain embodiments, the cooling article is applied to the subject's skin in proximity to the site of pain for a duration of at least 20 minutes. In certain embodiments, the cooling article is applied to the subject's skin in proximity to the site of pain for a duration of at least 30 minutes. In certain embodiments, the cooling article is applied to the subject's skin in proximity to the site of pain for a duration of from about 5 minutes to about 10 minutes, about 10 minutes to about 15 minutes, about 15 minutes to about 20 minutes, about 20 minutes to about 25 minutes, or about 25 minutes to about 30 minutes. In certain embodiments, the cooling article is applied to the subject's skin in proximity to the site of pain for a duration of about 5, 6, 7, 8, 9, 10, 11, 12, 13, 14, 15, 16, 17, 18, 19, 20, 21, 22, 23, 24, 25, 26, 27, 28, 29, or 30 minutes.

The methods may be further characterized according to the duration of time for which the skin in proximity to the site of pain is held below a certain temperature prior to administering the prodrug compound, such as a compound of Formula I. For example, in certain embodiments, the method is characterized by the feature that the cooling article is applied to the subject's skin in proximity to the site of pain to achieve a temperature of less than 30° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature of less than 28° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature of less than 26° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature of less than 24° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature of less than 22° C. for at least 10 minutes, 15 minutes, 20 minutes, or 30 minutes for the subject's skin in contact with the cooling article.

In certain embodiments, the method is characterized by the feature that the cooling article is applied to the subject's skin in proximity to the site of pain to achieve a temperature in the range of about 30° C. to about 27° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature in the range of about 29° C. to about 26° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature in the range of about 28° C. to about 25° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature in the range of about 27° C. to about 24° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature in the range of about 26° C. to about 23° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature in the range of about 25° C. to about 22° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature in the range of about 24° C. to about 21° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature in the range of about 23° C. to about 20° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature in the range of about 22° C. to about 19° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature in the range of about 20° C. to about 17° C. for at least 10 minutes, 15 minutes, 20 minutes, or 30 minutes for the subject's skin in contact with the cooling article.

Cooling Article Applied to Subject after Administering a Prodrug Compound

A cooling article may be applied to the subject after administering a prodrug compound, such as a compound of Formula I. To illustrate, in certain embodiments, a method described herein further comprises applying a cooling article to the subject's skin in proximity to the site of pain after administering the prodrug compound.

The methods may be further characterized according to the duration of time for which the cooling article is applied to the subject after administering the prodrug compound, such as a compound of Formula I. For example, in certain embodiments, after administering the prodrug compound, the cooling article is applied to the subject's skin in proximity to the site of pain for a duration of at least 10 minutes. In certain embodiments, after administering the prodrug compound, the cooling article is applied to the subject's skin in proximity to the site of pain for a duration of at least 15 minutes. In certain embodiments, after administering the prodrug compound, the cooling article is applied to the subject's skin in proximity to the site of pain for a duration of at least 20 minutes. In certain embodiments, after administering the prodrug compound, the cooling article is applied to the subject's skin in proximity to the site of pain for a duration of at least 30 minutes. In certain embodiments, after administering the prodrug compound, the cooling article is applied to the subject's skin in proximity to the site of pain for a duration of from about 5 minutes to about 10 minutes, about 10 minutes to about 15 minutes, about 15 minutes to about 20 minutes, about 20 minutes to about 25 minutes, or about 25 minutes to about 30 minutes. In certain embodiments, after administering the prodrug compound, the cooling article is applied to the subject's skin in proximity to the site of pain for a duration of about 5, 6, 7, 8, 9, 10, 11, 12, 13, 14, 15, 16, 17, 18, 19, 20, 21, 22, 23, 24, 25, 26, 27, 28, 29, or 30 minutes.

The methods may be further characterized according to the duration of time for which the skin in proximity to the site of pain is held below a certain temperature after administering the prodrug compound, such as a compound of Formula I. For example, in certain embodiments, the method is characterized by the feature that the cooling article is applied to the subject's skin in proximity to the site of pain to achieve a temperature of less than 30° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature of less than 28° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature of less than 26° C. for at least 10 minutes, 15 minutes, 20 minutes, or 30 minutes for the subject's skin in contact with the cooling article. In certain embodiments, the method is characterized by the feature that the cooling article is applied to the subject's skin in proximity to the site of pain to achieve a temperature of less than 24° C. for at least 10 minutes, 15 minutes, 20 minutes, or 30 minutes for the subject's skin in contact with the cooling article.

Temperature of Exterior Surface of the Cooling Article

The cooling article and methods that employ the cooling article may be further characterized according to the temperature of the exterior surface of the cooling article that may be applied to the subject's skin. For example, in certain embodiments, the cooling article has an exterior surface temperature in the range of from about 1° C. to about 15° C. for application to the subject's skin. In certain embodiments, the cooling article has an exterior surface temperature in the range of from about 1° C. to about 5° C. for application to the subject's skin. In certain embodiments, the cooling article has an exterior surface temperature in the range of from about 5° C. to about 7° C. for application to the subject's skin. In certain embodiments, the cooling article has an exterior surface temperature in the range of from about 7° C. to about 9° C. for application to the subject's skin. In certain embodiments, the cooling article has an exterior surface temperature in the range of from about 9° C. to about 11° C. for application to the subject's skin. In certain embodiments, the cooling article has an exterior surface temperature in the range of from about 11° C. to about 13° C. for application to the subject's skin. In certain embodiments, the cooling article has an exterior surface temperature in the range of from about 13° C. to about 15° C. for application to the subject's skin. In certain embodiments, the cooling article has an exterior surface temperature of about 1, 2, 3, 4, 5, 6, 7, 8, 9, 10, 11, 12, 13, 14, or 15° C. for application to the subject's skin.

Treating Itch

One aspect of the invention provides a method of treating or preventing topical itch in a subject, wherein the method comprises administering to a site of topical itch in a subject in need thereof an effective amount of a prodrug compound described herein, such as a compound of Formula I. Desirably, the method provides for treatment or prevention of topical itch for a duration of at least two, four, six, eight, ten, twelve, or fourteen days using a dose of prodrug compound having minimal systemic distribution of the prodrug compound and minimal systemic distribution of resiniferatoxin or a related compound produced from the prodrug compound In certain embodiments, the method is for treating topical itch. In certain embodiments, the method is for preventing topical itch.

The method may be further characterized by additional features, such as the identity of the prodrug compound and/or use of an agent that facilitates conversion of the prodrug compound to resiniferatoxin or a related compound.

Providing the Prodrug Compound in the Form of a Solution

The methods may be further characterized by the form in which the prodrug compound is provided. In certain embodiments, the prodrug compound is provided in the form of a solution. Desirably the solution is an aqueous solution formulated for injection to a subject. Exemplary solutions may be further characterized according to, for example, the pH of the solution and/or the temperature of the solution.

In certain embodiments, the prodrug compound is administered in the form of an aqueous solution having a pH in the range of from about 4 to about 10. In certain embodiments, the aqueous solution has a pH in the range of from about 4 to about 5. In certain embodiments, the aqueous solution has a pH in the range of from about 5 to about 6. In certain embodiments, the aqueous solution has a pH in the range of from about 6 to about 7. In certain embodiments, the aqueous solution has a pH in the range of from about 7 to about 8. In certain embodiments, the aqueous solution has a pH in the range of from about 8 to about 9. In certain embodiments, the aqueous solution has a pH in the range of from about 9 to about 10. In certain other embodiments, the aqueous solution has a pH in the range of from about 6.5 to about 7.5. In certain other embodiments, the aqueous solution has a pH of about 4, 5, 6, 7, 8, 9, or 10.

In certain embodiments, the solution has a temperature in the range of from about 5° C. to about 30° C. In certain embodiments, the solution has a temperature in the range of from about 5° C. to about 10° C. In certain embodiments, the solution has a temperature in the range of from about 10° C. to about 15° C. In certain embodiments, the solution has a temperature in the range of from about 15° C. to about 20° C. In certain embodiments, the solution has a temperature in the range of from about 20° C. to about 22° C. In certain embodiments, the solution has a temperature in the range of from about 22° C. to about 24° C. In certain embodiments, the solution has a temperature in the range of from about 24° C. to about 26° C. In certain embodiments, the solution has a temperature in the range of from about 26° C. to about 28° C. In certain embodiments, the solution has a temperature in the range of from about 28° C. to about 30° C. In certain embodiments, the solution has a temperature of about 5, 6, 7, 8, 9, 10, 11, 12, 13, 14, 15, 16, 17, 18, 19, 20, 21, 22, 23, 24, 25, 26, 27, 28, 29, or 30° C.

The solution containing a prodrug compound may be further characterized by the amount of any resiniferatoxin or a related compound in the solution. For example, for prodrug with a relatively short half-life in water, an aqueous solution containing a prodrug compound described herein may generate some resiniferatoxin or a related compound due to degradation of the prodrug compound. Accordingly, in certain embodiments, the solution containing a prodrug compound contains less than about 0.01% w/w, 0.1% w/w, 0.5% w/w, 1% w/w, 2% w/w, 5% w/w, 10% w/w, or 15% w/w resiniferatoxin or a related compound. In certain embodiments, the mole ratio of prodrug compound to resiniferatoxin (or related compound produced by degradation of the prodrug compound) in the solution is at least 20:1, 18:1, 16:1, 14:1, 12:1, 10:1, 8:1, 6:1, 5:1, 4:1, 3:1, 2:1, or 1:1.

The methods may be further characterized according to the volume of solution administered to the subject. The volume of the solution administered to the subject may be selected according to, for example, the size of the area effected by chronic pain. For instance, administering a solution to a finger joint will generally utilize a smaller volume of solution than when administering solution to a knee joint. In certain embodiments, the volume of solution administered to the subject is in the range of 0.1 mL to 25 mL. In certain embodiments, the volume of solution administered to the subject is in the range of 0.1 mL to 1 mL. In certain embodiments, the volume of solution administered to the subject is in the range of 1 mL to 5 mL. In certain embodiments, the volume of solution administered to the subject is in the range of 5 mL to 10 mL. In certain embodiments, the volume of solution administered to the subject is in the range of 10 mL to 15 mL. In certain embodiments, the volume of solution administered to the subject is in the range of 15 mL to 20 mL. In certain embodiments, the volume of solution administered to the subject is in the range of 20 mL to 25 mL. In certain embodiments, the volume of solution administered to the subject is in the range of about 0.1 to 0.5 mL, 0.5 to 1 mL, 1 to 2 mL, 2 to 3 mL, 3 to 4 mL, 4 to 5 mL, 5 to 6 mL, 6 to 7 mL, 7 to 8 mL, 8 to 9 mL, 9 to 10 mL, 10 to 11 mL, 11 to 12 mL, 12 to 13 mL, 13 to 14 mL, 14 to 15 mL, 15 to 16 mL, 16 to 17 mL, 17 to 18 mL, 18 to 19 mL, 19 to 20 mL, 20 to 21 mL, 21 to 22 mL, 22 to 23 mL, 23 to 24 mL, or 24 to 25 mL.

Exemplary volumes of solution for administration to a particular site of pain are provided in Table 6 below.

TABLE 6

| Site of Pain | Exemplary Volume of Solution Administered |
|---|---|
| subject's shoulder | about 2 mL to about 25 mL, about 5 mL to about 25 mL, about 10 mL to about 25 mL, about 15 mL to about 25 mL, about 20 mL to about 25 mL, about 13 mL to about 15 mL, about 8 mL to about 12 mL, about 9 mL to about 11 mL, or about 14 mL to about 16 mL. |
| subject's elbow | about 1 mL to about 15 mL, about 1 mL to about 2 mL, about 2 mL to about 3 mL, about 3 mL to about 4 mL, about 5 mL to about 8 mL, about 8 mL to about 10 mL, about 10 mL to about 15 mL, about 12 mL to about 15 mL, or about 13 mL to about 15 mL. |
| subject's wrist | about 1 mL to about 15 mL, about 1 mL to about 2 mL, about 2 mL to about 3 mL, about 3 mL to about 4 mL, about 5 mL to about 8 mL, about 8 mL to about 10 mL, about 10 mL to about 15 mL, about 12 mL to about 15 mL, or about 13 mL to about 15 mL. |
| subject's hand (e.g., a finger joint) | about 1 mL to about 15 mL, about 1 mL to about 2 mL, about 2 mL to about 3 mL, about 3 mL to about 4 mL, about 5 mL to about 8 mL, about 8 mL to about 10 mL, about 10 mL to about 15 mL, about 12 mL to about 15 mL, or about 13 mL to about 15 mL. |
| subject's spine | about 1 mL to about 15 mL, about 1 mL to about 2 mL, about 2 mL to about 3 mL, about 3 mL to about 4 mL, about 5 mL to about 8 mL, about 8 mL to about 10 mL, about 10 mL to about 15 mL, about 12 mL to about 15 mL, or about 13 mL to about 15 mL. |
| subject's hip | about 2 mL to about 25 mL, about 5 mL to about 25 mL, about 10 mL to about 25 mL, about 15 mL to about 25 mL, about 20 mL to about 25 mL, about 13 mL to about 15 mL, about 8 mL to about 12 mL, about 9 mL to about 11 mL, or about 14 mL to about 16 mL. |
| subject's knee | about 2 mL to about 25 mL, about 5 mL to about 25 mL, about 10 mL to about 25 mL, about 15 mL to about 25 mL, about 20 mL to about 25 mL, about 13 mL to about 15 mL, about 8 mL to about 12 mL, about 9 mL to about 11 mL, or about 14 mL to about 16 mL. |
| subject's ankle | about 1 mL to about 15 mL, about 1 mL to about 2 mL, about 2 mL to about 3 mL, about 3 mL to about 4 mL, about 5 mL to about 8 mL, about 8 mL to about 10 mL, about 10 mL to about 15 mL, about 12 mL to about 15 mL, or about 13 mL to about 15 mL. |
| subject's foot (e.g., a metatarsal joint) | about 1 mL to about 15 mL, about 1 mL to about 2 mL, about 2 mL to about 3 mL, about 3 mL to about 4 mL, about 5 mL to about 8 mL, about 8 mL to about 10 mL, about 10 mL to about 15 mL, about 12 mL to about 15 mL, or about 13 mL to about 15 mL. |

In a more specific embodiment, the prodrug compound is provided in the form of a solution, such as a solution characterized by one or more of the features described herein.

Administering a Vasoconstricting Agent

The methods may be further characterized by administration of a vasoconstricting agent to the subject. For example, in certain embodiments, the method further comprises administering to the subject a vasoconstricting agent. In certain embodiments, the vasoconstricting agent is administered prior to or concurrently with the prodrug compound.

In certain embodiments, the vasoconstricting agent is epinephrine or phenylephrine. In certain embodiments, the vasoconstricting agent is epinephrine. In certain embodiments, the vasoconstricting agent is phenylephrine. The dose of vasoconstricting agent may be adjusted to achieve the desired effect, such as limiting systemic distribution of the prodrug compound and any resiniferatoxin or a related compound produced therefrom. In certain embodiments, the dose of vasoconstricting agent is in the range from about 1 µg to about 300 µg. In certain embodiments, the dose is in the range of from about 1 µg to about 150 µg. In certain embodiments, the dose is in the range of from about 10 µg to about 100 µg. In certain embodiments, the dose is from about 1 µg to about 25 µg, about 25 µg to about 50 µg, about 50 µg to about 75 µg, about 75 µg to about 100 µg, about 100 µg to about 125 µg, or about 125 µg to about 150 µg.

In a more specific embodiment, the vasoconstricting agent is administered prior to or concurrently with the prodrug compound.

Use of a Calcium Salt

The methods may be further characterized by the administration and identity of a calcium salt. Accordingly, in certain embodiments, a calcium salt is administered to the site to receive the prodrug compound of, prior to, or after administering to the subject the prodrug compound.

The methods may be further characterized according to the identity of the calcium salt. For example, in certain embodiments, the calcium salt is a calcium halide salt. In certain embodiments, the calcium salt is calcium chloride. In certain other embodiments, the calcium salt is a calcium organic carboxylate salt. In certain embodiments, the calcium salt is calcium acetate. In certain other embodiments, the calcium salt is calcium chloride, calcium phosphate, calcium acetate, calcium citrate, calcium lactate, or calcium gluconate. In certain embodiments, the calcium salt is calcium phosphate.

Use of an Agent that Facilitates Conversion of the Prodrug Compound to Resiniferatoxin or a Related Compound The methods may be further characterized by the use of an agent that facilitates conversion of the prodrug compound to resiniferatoxin or a related compound. For instance, in certain embodiments, in proximity to the time in which the prodrug compound is administered to the subject, the prodrug compound is exposed to an agent that facilitates conversion of the prodrug compound to resiniferatoxin or a related compound.

The time at which the prodrug compound is exposed to an agent that facilitates conversation of the prodrug compound to resiniferatoxin or a related compound can be further specified. For instance, in certain embodiments, within about 1 hour, 30 minutes, 15 minutes, 10 minutes, or 5 minutes prior to the time in which the prodrug compound is administered to the subject, the prodrug compound is exposed to an agent that facilitates conversion of the prodrug compound to resiniferatoxin or a related compound.

The methods may be further characterized according to the identity of the agent that facilitates conversion of the prodrug compound to resiniferatoxin or a related compound. For example, in certain embodiments, the agent that facilitates conversion of the prodrug compound is water, a protic organic solvent, or a mixture thereof. In certain embodiments, the agent that facilitates conversion of the prodrug compound to resiniferatoxin or a related compound is water. In certain embodiments, the agent that facilitates conversion of the prodrug compound to resiniferatoxin or a related compound is a mixture of water and a protic organic solvent. In certain embodiments, the agent that facilitates conversion of the prodrug compound to resiniferatoxin or a related compound is a protic organic solvent. In certain embodiments, the agent that facilitates conversion of the prodrug compound to resiniferatoxin or a related compound is a mixture of water and a polar aprotic solvent (e.g., DMSO).

The methods may be further characterized according to preservation conditions of the prodrug compound, prior to exposing it to an agent that facilitates its conversion to resiniferatoxin or a related compound. For example, in certain embodiments, prior to exposing the prodrug compound to an agent that facilitates conversion of the prodrug compound to resiniferatoxin or a related compound, the prodrug compound is preserved in a substantially aprotic environment. In certain other embodiments, prior to exposing the prodrug compound to an agent that facilitates conversion of the prodrug compound to resiniferatoxin or a related compound, the prodrug is preserved in an aprotic environment. In certain other embodiments, prior to exposing the prodrug compound to an agent that facilitates conversion of the prodrug compound to resiniferatoxin or a related compound, the prodrug compound is preserved in an environment containing less than 5% w/w, 2% w/w, 1% w/w, 0.5% w/w, or 0.1% w/w water. In certain other embodiments, prior to exposing the prodrug compound to an agent that facilitates conversion of the prodrug compound to resiniferatoxin or a related compound, the prodrug compound is preserved in an environment containing less than 5% w/w, 2% w/w, 1% w/w, 0.5% w/w, or 0.1% w/w of a protic compound.

Alternatively, in proximity to the time in which the prodrug compound is administered to the subject, the prodrug compound is not exposed to an agent that facilitates conversion of the prodrug compound to resiniferatoxin or a related compound.

Subjects

In certain embodiments, the subject is a human. In certain embodiments, the subject is an adult human. In certain embodiments, the subject is a geriatric human. In certain embodiments, the subject is a mammal. In certain embodiments, the subject is a canine, feline, or equine.

Administering a Local Anesthetic Agent

The methods may be further characterized by administration of a local anesthetic agent to the subject. For example, in certain embodiments, the method further comprises administering to the subject a local anesthetic agent. In certain embodiments, the local anesthetic agent is administered prior to or concurrently with the prodrug compound.

The methods may be further characterized according to the identity of the local anesthetic agent. For example, in certain embodiments, the local anesthetic agent is a caine analgesic. In certain embodiments, the local anesthetic agent is bupivacaine, butacaine, chloroprocaine, cyclomethycaine, dibucaine, falicaine, hexylcaine, levobupivacaine, lidocaine, mepivacaine, phenacaine, prilocaine, procaine, proparacaine, propoxycaine, ropivacaine, tetracaine, or a pharmaceutically acceptable salt thereof. In certain embodiments, the local anesthetic agent is lidocaine or a pharmaceutically acceptable salt thereof. In certain embodiments, the local anesthetic agent is lidocaine hydrochloride salt. In certain embodiments, the local anesthetic agent is bupivacaine.

The methods may be further characterized according to the dose of the local anesthetic agent. For example, in certain embodiments, the local anesthetic agent is administered at a dose ranging from about 0.1 g to about 2 g. In certain embodiments, the local anesthetic agent is administered at a dose ranging from about 0.1 g to about 1 g. In certain embodiments, the local anesthetic agent is administered at a dose ranging from about 0.1 g to about 0.5 g. In certain embodiments, the local anesthetic agent is administered at a dose of about 0.1 to 0.5 mg, 0.5 to 1 mg, 1 to 2 mg, 2 to 3 mg, 3 to 4 mg, 4 to 5 mg, 5 to 6 mg, 6 to 7 mg, 7 to 8 mg, 8 to 9 mg, 9 to 10 mg, 10 to 11 mg, 11 to 12 mg, 12 to 13 mg, 13 to 14 mg, or 14 to 15 mg.

In a more specific embodiment, a local anesthetic agent is administered prior to or concurrently with the prodrug compound.

Additional Features

The methods may be further characterized according to the route of administration. For example, in certain embodiments, the prodrug compound is administered to the patient by injection, such as intra-articular injection or subcutaneous injection. In certain embodiments, the prodrug compound is administered to the patient by topical administration, such as transdermal administration.

Another aspect of the invention provides for the use of a compound described herein (such as a compound of Formula I, II, III, IV, or V, or other compound in Section I) in the manufacture of a medicament. In certain embodiments, the medicament is for treating or preventing a disorder described herein, such as pain.

Another aspect of the invention provides for the use of a compound described herein (such as a compound of Formula I, II, III, IV, or V, or other compound in Section I) for treating or preventing a medical disorder, such as a medical disorder described herein (e.g., pain).

Further, it is contemplated that the prodrug compounds described herein, such as a compound of Formula I, II, III, IV, or V, or other compound in Section I, can agonize the activity of TRPV1. Accordingly, another aspect of the invention provides a method of agonizing the activity of TRPV1. The method comprises exposing a TRPV1 to an effective amount of a prodrug compound described herein, such as a compound of Formula I, II, III, IV, or V, or other compound in Section I, to agonize TRPV1 activity. In certain embodiments, the particular compound of Formula I, II, III, IV, or V is the compound defined by one of the embodiments described above.

III. Pharmaceutical Compositions and Dosing Considerations

One aspect of the invention provides pharmaceutical compositions, which comprise one or more of the compounds described above, formulated together with one or more pharmaceutically acceptable carriers. The pharmaceutical compositions may be specially formulated for administration in liquid form, including those adapted for injection to a subject as a sterile solution. Accordingly, one aspect of the invention provides a pharmaceutical composition comprising a compound of Formula I, II, III, IV, or V, or other compounds in Section I, and a pharmaceutically acceptable carrier.

More specifically with regards to injectable formulations, various injectable formulations are described in the literature and known to those of skill in the art. The injectable formulation may typically contain water and one or more additional components to render the formulation optimally suited for injection into a subject.

When administering a prodrug compound (e.g., a compound of Formula I, II, III, IV, or V, or other compound in Section I) according to methods described herein, the prodrug compound is desirably administered in the form of a pharmaceutical composition formulated for injection. In certain embodiments, the pharmaceutical composition formulated for injection is an aqueous pharmaceutical composition.

The prodrug compound (e.g., a compound of Formula I, II, III, IV, or V, or other compound in Section I) may be dissolved in oils, polyethylene glycol (PEG), propylene glycol (PG), and/or other solvents commonly used to prepare injectable or implantable solutions. Suitable pharmaceutically acceptable vehicles include aqueous vehicles, nonaqueous vehicles, antimicrobial agents, isotonic agents, buffers, antioxidants, suspending and dispersing agents, emulsifying agents, sequestering or chelating agents, and combinations or mixtures thereof. It is appreciated that when one or more solvents are used in the formulations of the invention, they may be combined, e.g., with a pharmaceutically acceptable buffer and may be present in the final formulation, e.g., in an amount ranging from about 10% to about 100%, more preferably from about 20% to about 100%.

Exemplary aqueous vehicles include Sodium Chloride Injection, Bacteriostatic Sodium Chloride Injection, Ringers Injection, Isotonic Dextrose Injection, Sterile Water Injection, Bacteriostatic Sterile Water Injection, Dextrose Lactated Ringers Injection and any combinations or mixtures thereof.

Exemplary nonaqueous parenteral vehicles include fixed oils of vegetable origin, cottonseed oil, corn oil, sesame oil, peanut oil, and combinations or mixtures thereof.

Exemplary antimicrobial agents in bacteriostatic or fungistatic concentrations include phenols, cresols, mercurials, benzyl alcohol, chlorobutanol, ethyl and propyl p-hydroxybenzoic acid esters, thimerosal, benzalkonium chloride, benzethonium chloride, and mixtures thereof.

Exemplary isotonic agents include sodium chloride, dextrose, and combinations or mixtures thereof.

Exemplary antioxidants include ascorbic acid, sodium bisulfate, and combinations or mixtures thereof.

Exemplary suspending and dispersing agents include sodium carboxymethylcelluose, hydroxypropyl methylcellulose, polyvinylpyrrolidone, any combinations or mixtures thereof.

Exemplary emulsifying agents include anionic emulsifying agents (e.g., sodium lauryl sulfate, sodium stearate, calcium oleate, and combinations or mixtures thereof), cationic emulsifying agents (e.g., cetrimide), and non-ionic emulsifying agents (e.g., Polysorbate 80 (Tween 80)).

Exemplary sequestering or chelating agents of metal ions include ethylenediaminetetraacetic acid (EDTA), citric acid, sorbitol, tartaric acid, phosphoric acid, and the like.

Suitable surfactants include, but are not limited to, sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80), sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations thereof. When one or more surfactants are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%. In certain other embodiments, a surfactant can preferably be combined with one or more of the pharmaceutically acceptable vehicles previously described herein so that the surfactant and vehicle(s) prevent the initial stinging or burning discomfort associated with administration of resiniferatoxin or a related compound.

Buffering agents may also be used to provide drug stability; to control the therapeutic activity of the drug substance (Ansel, Howard C., "Introduction to Pharmaceutical Dosage Forms," $4^{th}$ Ed., 1985); and/or to prevent the initial stinging or burning discomfort associated with administration of resiniferatoxin or a related compound. Suitable buffers include, but are not limited to, sodium bicarbonate, sodium citrate, citric acid, sodium phosphate, pharmaceutically acceptable salts thereof, and combinations thereof. When one or more buffers are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%. In certain embodiments, the buffer is an acetate salt, phosphate salt, citrate salt; corresponding acids of the foregoing; and combinations or mixtures thereof.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the salt thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent, the effective amount may be less than when the agent is used alone.

IV. Medical Kits

Another aspect of the invention provides a medical kit comprising, for example, (i) a therapeutic agent described herein (e.g., a prodrug compound, such as a compound of Formula I, II, III, IV, or V, or other compound in Section I), and (ii) instructions for use according to methods described herein.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A compound of Formula I or Formula II, wherein Formula I is represented by:

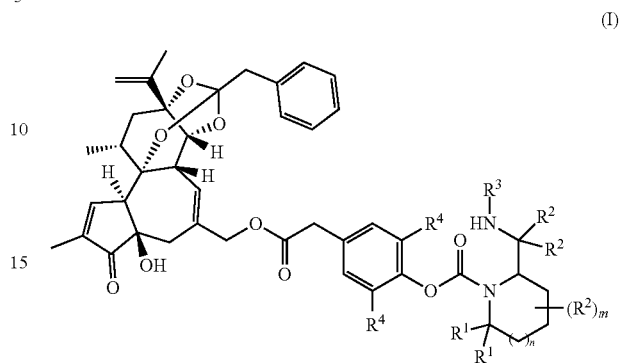

or a pharmaceutically acceptable salt thereof; wherein:

$R_1$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl; or two occurrences of $R_1$ are taken together with the carbon atom to which they are attached to form a 3-6 membered saturated carbocyclic or heterocyclic ring;

$R^2$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl; or two occurrences of $R^2$ attached to the same carbon atom are taken together to represent an oxo group; or two occurrences of $R^2$ attached to the same carbon atom are taken together with the carbon atom to which they are attached to form a 3-6 membered saturated carbocyclic or heterocyclic ring;

$R^3$ is hydrogen, $C_{1-6}$ alkyl, $C_{1-6}$ haloalkyl, $C_{3-7}$ cycloalkyl, 4-8 membered heterocycloalkyl, or —C(=NH)—NH$_2$; wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl; provided that if $R^3$ is hydrogen, methyl, or ethyl, then at least one of $R^1$ and $R^2$ is not hydrogen; and $R^4$ represents independently for each occurrence hydrogen, halogen, $C_{1-4}$ alkyl, $C_{1-4}$ haloalkyl, $C_{1-4}$ alkoxyl, or $C_{1-4}$ haloalkoxyl;

m is 0, 1, 2, or 3; and n is 0, 1, or 2; and

Formula II is represented by:

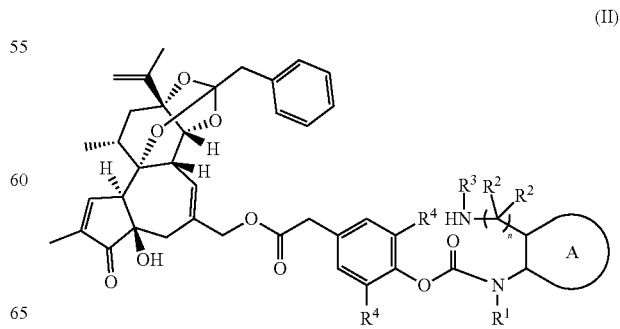

or a pharmaceutically acceptable salt thereof; wherein:

$R^1$ is hydrogen, $C_{1-6}$ alkyl, $C_{1-6}$ haloalkyl, $C_{3-7}$ cycloalkyl, $C_6$ aryl, or 4-8 membered heterocycloalkyl;

$R^2$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl; or two occurrences of $R^2$ are taken together to represent an oxo group; or two occurrences of $R^2$ are taken together with the carbon atom to which they are attached to form a 3-6 membered saturated carbocyclic or heterocyclic ring;

$R^3$ is hydrogen, $C_{1-6}$ alkyl, $C_{1-6}$ haloalkyl, $C_{3-7}$ cycloalkyl, 4-8 membered heterocycloalkyl, or —C(=NH)—NH$_2$; wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

$R^4$ represents independently for each occurrence hydrogen, halogen, $C_{1-4}$ alkyl, $C_{1-4}$ haloalkyl, $C_{1-4}$ alkoxyl, or $C_{1-4}$ haloalkoxyl;

Ring A is one of the following:
- a 3-8 membered heterocyclic ring or a $C_{3-8}$ saturated or partially unsaturated carbocyclic ring, each of which is optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl; or
- a 6-membered carbocyclic aromatic ring substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl; and n is 0 or 1.

2. The compound of claim 1, wherein the compound is a compound of Formula I or a pharmaceutically acceptable salt thereof.

3. The compound of claim 2, wherein at least one $R^1$ represents $C_{1-6}$ alkyl, $C_{1-6}$ haloalkyl, $C_{3-7}$ cycloalkyl, $C_6$ aryl, or 3-8 membered heterocycloalkyl; or two occurrences of $R^1$ are taken together with the carbon atom to which they are attached to form a 3-6 membered saturated carbocyclic or heterocyclic ring.

4. The compound of claim 2, wherein $R^1$ represents independently for each occurrence $C_{1-6}$ alkyl or $C_{3-7}$ cycloalkyl.

5. The compound of claim 2, wherein two occurrences of $R^1$ are taken together with the carbon atom to which they are attached to form a 3-6 membered saturated carbocyclic or heterocyclic ring.

6. The compound of claim 2, wherein at least one $R^2$ represents $C_{1-6}$ alkyl, $C_{1-6}$ haloalkyl, $C_{3-7}$ cycloalkyl, $C_6$ aryl, or 3-8 membered heterocycloalkyl; or two occurrences of $R^2$ attached to the same carbon atom are taken together to represent an oxo group; or two occurrences of $R^2$ attached to the same carbon atom are taken together with the carbon atom to which they are attached to form a 3-6 membered saturated carbocyclic or heterocyclic ring.

7. The compound of claim 2, wherein two occurrences of $R^2$ attached to the same carbon atom are taken together with the carbon atom to which they are attached to form a 3-6 membered saturated carbocyclic or heterocyclic ring.

8. The compound of claim 1, wherein the compound is a compound of Formula II or a pharmaceutically acceptable salt thereof.

9. The compound of claim 8, wherein $R^2$ is hydrogen.

10. The compound of claim 8, wherein at least one $R^2$ represents independently for each occurrence $C_{1-6}$ alkyl or $C_{3-7}$ cycloalkyl; or two occurrences of $R^2$ are taken together with the carbon atom to which they are attached to form a 3-6 membered saturated carbocyclic or heterocyclic ring.

11. The compound of claim 8, wherein Ring A is a 3-8 membered heterocyclic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl.

12. The compound of claim 8, wherein Ring A is a 5-6 membered heteroaromatic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl.

13. The compound of claim 8, wherein Ring A is a $C_{3-8}$ saturated or partially unsaturated carbocyclic ring optionally substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, oxo, and $C_{1-4}$ haloalkoxyl.

14. The compound of claim 8, wherein Ring A is a 6-membered carbocyclic aromatic ring substituted with 1, 2, or 3 substituents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl.

15. The compound of claim 8, wherein n is 1.

16. A compound represented by Formula III:

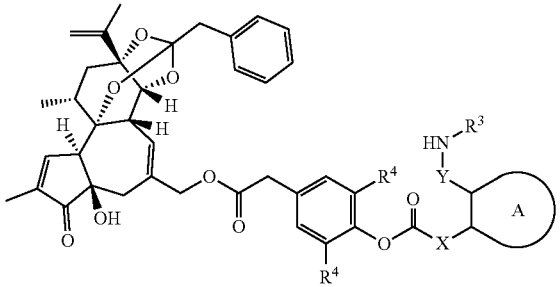

(III)

or a pharmaceutically acceptable salt thereof; wherein:

X is —C($R^1$)$_2$—, a bond, or —O—;

Y is —C($R^2$)$_2$— or a bond; provided X and Y are not both a bond;

$R^1$ represents independently for each occurrence hydrogen, halogen, $C_{1-6}$ alkyl, $C_{1-6}$ haloalkyl, $C_{3-7}$ cycloalkyl, $C_6$ aryl, or 3-8 membered heterocycloalkyl; or two occurrences of $R^1$ are taken together with the carbon atom to which they are attached to form a 3-6 membered saturated carbocyclic or heterocyclic ring;

$R^2$ represents independently for each occurrence hydrogen, $C_{1-6}$ alkyl, $C_{1-6}$ haloalkyl, $C_{3-7}$ cycloalkyl, $C_6$ aryl, or 3-8 membered heterocycloalkyl; or two occurrences of $R^2$ are taken together to represent an oxo group; or two occurrences of $R^2$ are taken together with the carbon atom to which they are attached to form a 3-6 membered saturated carbocyclic or heterocyclic ring;

$R^3$ is hydrogen, $C_{1-6}$ alkyl, $C_{1-6}$ haloalkyl, $C_{3-7}$ cycloalkyl, 4-8 membered heterocycloalkyl, or —C(=NH)—NH$_2$; wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

$R^4$ represents independently for each occurrence hydrogen, halogen, $C_{1-4}$ alkyl, $C_{1-4}$ haloalkyl, $C_{1-4}$ alkoxyl, or $C_{1-4}$ haloalkoxyl; and Ring A is one of the following:
- a 6-membered carbocyclic aromatic ring or a 5-6 membered heteroaromatic ring, each of which is optionally substituted with 1, 2, or 3 substitutents independently selected from the group consisting of halogen, hydroxyl, $C_{1-6}$ alkyl, $C_{1-6}$ haloalkyl, $C_{3-7}$ cycloalkyl, $C_{1-4}$ alkoxyl, and $C_{1-4}$ haloalkoxyl; or
- a $C_{3-8}$ saturated or partially unsaturated carbocyclic ring or a 3-8 membered saturated or partially unsaturated heterocylic ring, each of which is optionally substituted with 1, 2, or 3 substitutents independently selected from the group consisting of halogen, hydroxyl, oxo, $C_{1-6}$ alkyl, $C_{1-6}$ haloalkyl, $C_{3-7}$ cycloalkyl, $C_{1-4}$ alkoxyl, and $C_{1-4}$ haloalkoxyl.

17. A compound of Formula IV or V, wherein Formula IV is represented by:

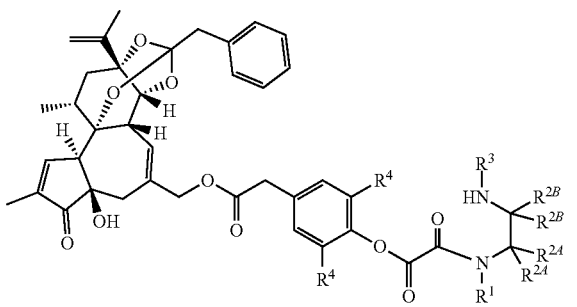

(IV)

or a pharmaceutically acceptable salt thereof; wherein:

$R^1$ is hydrogen, $C_{1-6}$ alkyl, $C_{1-6}$ haloalkyl, $C_{3-7}$ cycloalkyl, $C_6$ aryl, or 4-8 membered heterocycloalkyl; or $R^1$ and an occurrence of $R^{2A}$ are taken together with the atoms to which they are attached to form a 3-8 membered saturated heterocyclic ring optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

$R^{2A}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl; or two occurrences of $R^{2A}$ are taken together to represent an oxo group; or two occurrences of $R^{2A}$ are taken together with the carbon atom to which they are attached to form a 3-6 membered saturated carbocyclic or heterocyclic ring; or an occurrence of $R^{2A}$ and an occurrence of $R^{2B}$ are taken together with the carbon atoms to which they are attached to form a 3-6 membered saturated carbocyclic or heterocyclic ring;

$R^{2B}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl; or two occurrences of $R^{2B}$ are taken together to represent an oxo group; or two occurrences of $R^{2B}$ are taken together with the carbon atom to which they are attached to form a 3-6 membered saturated carbocyclic or heterocyclic ring;

$R^3$ is hydrogen, $C_{1-6}$ alkyl, $C_{1-6}$ haloalkyl, $C_{3-7}$ cycloalkyl, 4-8 membered heterocycloalkyl, or —C(=NH)—NH$_2$;

wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl; and $R^4$ represents independently for each occurrence hydrogen, halogen, $C_{1-4}$ alkyl, $C_{1-4}$ haloalkyl, $C_{1-4}$ alkoxyl, or $C_{1-4}$ haloalkoxyl; and Formula V is represented by:

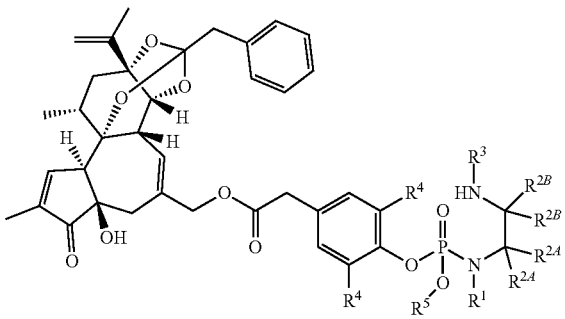

(V)

or a pharmaceutically acceptable salt thereof; wherein:

$R^1$ is hydrogen, $C_{1-6}$ alkyl, $C_{1-6}$ haloalkyl, $C_{3-7}$ cycloalkyl, $C_6$ aryl, or 4-8 membered heterocycloalkyl; or $R^1$ and an occurrence of $R^{2A}$ are taken together with the atoms to which they are attached to form a 3-8 membered saturated heterocyclic ring optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

$R^{2A}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl; or two occurrences of $R^{2A}$ are taken together to represent an oxo group; or two occurrences of $R^{2A}$ are taken together with the carbon atom to which they are attached to form a 3-6 membered saturated carbocyclic or heterocyclic ring; or an occurrence of $R^{2A}$ and an occurrence of $R^{2B}$ are taken together with the carbon atoms to which they are attached to form a 3-6 membered saturated carbocyclic or heterocyclic ring;

$R^{2B}$ represents independently for each occurrence hydrogen, $C_{1-6}$ alkyl, $C_{1-6}$ haloalkyl, $C_{3-7}$ cycloalkyl, $C_6$ aryl, or 3-8 membered heterocyclyl; or two occurrences of $R^{2B}$ are taken together to represent an oxo group; or two occurrences of $R^{2B}$ are taken together with the carbon atom to which they are attached to form a 3-6 membered saturated carbocyclic or heterocyclic ring:

$R^3$ is hydrogen, $C_{1-6}$ alkyl, $C_{1-6}$ haloalkyl, $C_{3-7}$ cycloalkyl, 4-8 membered heterocycloalkyl, or —C(=NH)—NH$_2$; wherein $C_{1-6}$ alkyl, $C_{3-7}$ cycloalkyl, and 4-8 membered heterocycloalkyl are each optionally substituted with 1, 2, or 3 substituents independently selected from the group consisting of halogen, hydroxyl, oxo, $C_{1-4}$ alkyl, $C_{1-4}$ haloalkyl, $C_{3-7}$ cycloalkyl, and $C_{1-4}$ alkoxyl;

$R^4$ represents independently for each occurrence hydrogen, halogen, $C_{1-4}$ alkyl, $C_{1-4}$ haloalkyl, $C_{1-4}$ alkoxyl, or $C_{1-4}$ haloalkoxyl; and $R^5$ is hydrogen, $C_{1-6}$ alkyl, $C_{1-6}$ haloalkyl, $C_{3-7}$ cycloalkyl, $C_6$ aryl, or 3-8 membered heterocyclyl.

18. A pharmaceutical composition comprising a compound of claim 1 and a pharmaceutically acceptable carrier.

19. A method of treating pain in a subject, comprising administering a therapeutically effective amount of a compound of claim 1 to a subject in need thereof to treat the pain.

20. A method of agonizing the activity of TRPV1, comprising exposing a TRPV1 to an effective amount of a compound of claim 1 to agonize the activity of said TRPV1.

\* \* \* \* \*